(12) United States Patent
Barrow et al.

(10) Patent No.: US 6,339,090 B1
(45) Date of Patent: Jan. 15, 2002

(54) ALPHA 1A ADRENERGIC RECEPTOR ANTAGONISTS

(75) Inventors: James C. Barrow, Harleysville; Harold G. Selnick, Ambler; Philippe G. Nantermet, Lansdale, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/363,631

(22) Filed: Jul. 29, 1999

Related U.S. Application Data

(60) Provisional application No. 60/094,600, filed on Jul. 30, 1998.

(30) Foreign Application Priority Data

Oct. 13, 1998 (GB) .............................................. 9822364

(51) Int. Cl.⁷ ............................................... A01N 43/54
(52) U.S. Cl. ....................................... 514/274; 544/316
(58) Field of Search ........................... 514/274; 544/316

(56) References Cited

U.S. PATENT DOCUMENTS

| | | | |
|---|---|---|---|
| 4,661,491 A | 4/1987 | Regnier ...................... | 514/260 |
| 4,769,371 A | 9/1988 | Atwal ......................... | 514/275 |
| 4,847,379 A | 7/1989 | Atwal ......................... | 544/316 |
| 4,855,301 A | 8/1989 | Atwal et al. ................. | 514/269 |
| 5,942,517 A | 8/1999 | Nagarathnam et al. ..... | 544/331 |

FOREIGN PATENT DOCUMENTS

| | | |
|---|---|---|
| EP | 204597 | 5/1986 |
| WO | WO 92/00073 | 1/1992 |
| WO | WOI 92/16213 | 10/1992 |
| WO | WO 94/08040 | 4/1994 |
| WO | WO 94/10989 | 5/1994 |
| WO | WO 96/14846 | 5/1996 |
| WO | WO 97/17969 | 5/1997 |
| WO | WO 97/42956 | 11/1997 |
| WO | WO 98/57632 | 12/1998 |
| WO | WO 98/57638 | 12/1998 |
| WO | WO 98/57639 | 12/1998 |
| WO | WO 98/57640 | 12/1998 |
| WO | WO 98/57641 | 12/1998 |
| WO | WO 98/57642 | 12/1998 |

OTHER PUBLICATIONS

Wong et al, Chemical Abstracts, vol. 128, entry 61520c (1998).*

G. C. Rovnyak et al., "Dihydropyrimidine Calcium Channel Blockers . . . ", J. Med. Chem., 35 (17), 3254–63 (1992).

K. S. Atwal et al., "Substituted 1,4–Dihydropyrimidines. 3. Synthesis of Selectively Functionalized 2–Hetero–1,4–dihydropyrimidines", J. Org. Chem., 54(25), 5898–907 (1989).

K. S. Atwal et al., "Dihydropyrimidine Calcium Channel Blockers . . . ", J. Med. Chem., 33(9), 2629–35 (1990).

* cited by examiner

*Primary Examiner*—John M. Ford
(74) *Attorney, Agent, or Firm*—Baerbel R. Brown; Catherine D. Fitch; Kenneth R. Walton

(57) ABSTRACT

This invention relates to certain novel compounds and derivatives thereof, their synthesis, and their use as alpha 1a adrenergic receptor antagonists. One application of these compounds is in the treatment of benign prostatic hyperplasia. These compounds are selective in their ability to relax smooth muscle tissue enriched in the alpha 1a receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia are achieved.

22 Claims, No Drawings

ALPHA 1A ADRENERGIC RECEPTOR ANTAGONISTS

This application claims the benefit of U.S. Provisional Application No. 60/094,600, filed Jul. 30, 1998.

FIELD OF THE INVENTION

This invention relates to certain novel compounds and derivatives thereof, their synthesis, and their use as alpha 1a adrenoceptor antagonists. More particularly, the compounds of the present invention are useful for treating benign prostatic hyperplasia (BPH).

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were farther subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., Adrenoreceptors: Molecular Biology. Biochemistry and Pharmacology, (Progress in Basic and Clinical Pharmacology series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Martin C. Michel, et al., *Naunyn-Schmiedeberg's Arch. Pharmacol.* (1995) 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra.

In benign prostatic hyperplasia, the male hormone 5-alpha-dihydrotestosterone has been identified as the principal culprit. The continual production of 5a-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.s' product PROSCAR® (finasteride). The effect of this compound is to inhibit the enzyme testosterone 5-a reductase, which converts testosterone into 5a-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/00073, the selective ability of the R(+) enantiomer of terazosin to bind to adrenergic receptors of the $alpha_1$ subtype was reported. In addition, in WO 92/16213, combinations of Sa-reductase inhibitory compounds and alpha1-adrenergic receptor blockers (terazosin, doxazosin, prazosin, bunazosin, indoramin, alfulzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The recent cloning of the human alpha 1a adrenergic receptor (ATCC CRL 11140) and the use of a screening assay utilizing the cloned human alpha 1a receptor enables identification of compounds which specifically interact with the human alpha 1a adrenergic receptor. [PCT International Application Publication Nos. WO94/08040, published Apr. 14, 1994 and WO94/10989, published May 26, 1994] As disclosed in the instant patent disclosure, a cloned human alpha 1a adrenergic receptor and a method for identifying compounds which bind the human alpha 1a receptor has now made possible the identification of selective human alpha 1a adrenergic receptor antagonists useful for treating BPH.

WO 96/14846, published May 23, 1996, discloses a broad genus of dihydropyrimidine compounds and proposes their use as selective antagonists for human alpha 1a receptors. Compounds were assayed using cloned human alpha adrenergic receptors, and certain of the compounds so assayed were disclosed to be selective alpha 1a antagonists.

The instant application presents novel dihydropyrimidine compounds (generally referred to herein as "reverse dihydropyrimidinones" as described below) which are useful as selective alpha 1a antagonists and which typically exhibit high potency and high selectivity in screening assays for alpha 1a receptor binding and in assays for determining selective binding to alpha 1a receptors over alpha 1b and 1d receptors. These compounds are further tested for binding to other human alpha 1 receptor subtypes, as well as counter-screened against other types of receptors (e.g., alpha 2), thereby further defining the specificity of the compounds of the present invention for the human alpha 1a adrenergic receptor.

The compounds of the present invention are useful as agents for treating BPH in animals, preferably mammals, especially humans. The alpha 1a adrenergic receptor antagonist compounds of the invention are also useful for relaxing lower urinary tract tissue in animals, preferably mammals, especially humans.

SUMMARY OF THE INVENTION

The present invention provides compounds for the treatment of urinary obstruction caused by benign prostatic hyperplasia (BPH). The compounds antagonize the human alpha 1a adrenergic receptor at nanomolar and subnanomolar concentrations while typically exhibiting at least ten fold lower affinity for the alpha 1d and alpha 1b human adrenergic receptors and many other G-protein coupled receptors. This invention has the advantage over non-selective alpha 1 adrenoceptor antagonists of reduced side effects related to peripheral adrenergic blockade. Such side effects include hypotension, syncope, lethargy, etc.

The present invention is a compound of formula (I):

(I)

wherein $R^1$ is selected from phenyl, substituted phenyl, pyridyl, and substituted pyridyl, wherein the substituents on the phenyl or the pyridyl are independently selected from F, Cl, Br, I, $(CH_2)_{0-4}CF_3$, CN, $NO_2$, $R^a$, and $OR^a$;

$R^{10}$ is selected from H, OH, CN, $R^b$, $OR^b$, $(CH_2)_{1-4}OR^b$ and $(CH_2)_{0-4}CF_3$;

m is an integer of from 0 to 2;

L is selected from $(CH_2)_k$, $(CHR^2)_k$, $CR^8R^9(CH_2)_{k-1}$, $(CH_2)_{k-1}CR^8R^9$, $CH_2CR^8R^9CH_2$, $CH_2CH_2CR^8R^9CH_2$, and $CH_2CR^8R^9CH_2CH_2$;

$R^2$ is selected from RC and $(CH_2)_{0-4}CF_3$;

k is an integer of from 2 to 4;

$R^4$ is selected from H, Rd and $(CH_2)_{0-4}CF_3$;

$R^5$ is selected from H, $R^e$, $(CH_2)_{1-4}OR^e$, and $(CH_2)_{1-4}CF_3$;

$R^6$ is selected from H and $R^f$;

$R^7$ is selected from H, $R^g$, $(CH_2)_{1-4}OR^g$, $C(=O)OR^g$, $C(=O)R^g$ and $(CH_2)_{0-4}CF_3$;

$R^8$ and $R^9$ are each independently selected from $R^c$ and $(CH_2)_{0-4}CF_3$;

each X is independently selected from F, Cl, Br, I, CN and $R^h$;

$R^a$, $R^d$, $R^e$, $R^f$, $R^g$ and $R^h$ are each independently selected from $C_1$ to $C_6$ alkyl;

$R^b$ and $R^c$ are independently selected from $C_1$ to $C_6$ alkyl and $C_3$ to $C_7$ cyclic alkyl;

and q is an integer of from 0 to 4, provided that when R7 is $COR^g$ or $COOR^g$, $R^1$ is not phenyl; or a pharmaceutically acceptable salt thereof.

A first embodiment of the invention is a compound of formula (I), wherein $R^1$ is selected from phenyl, mono-, di- or tri-substituted phenyl, pyridyl, and mono-, di-, or tri-substituted pyridyl, wherein the substituents on the phenyl or the pyridyl are independently selected from F, Cl, Br, I, CN and $R^a$;

$R^{10}$ is selected from H, OH, CN, $R^b$ and $OR^b$;

$R^2$ is selected from H and $R^c$;

$R^4$ is selected from H and $R^d$;

$R^5$ is selected from H, $R^e$ and $(CH_2)_{1-4}OR^e$;

$R^7$ is selected from H, $R^g$, $(CH_2)_{1-4}OR^g$, $C(=O)OR^g$ and $C(=O)R^g$;

$R^8$ and $R^9$ are each $R^c$;

$R^a$, $R^b$, $R^c$, $R^d$, $R^e$, $R^f$, $R^g$ and $R^h$ are each independently selected from $C_1$ to $C_4$ alkyl;

q is an integer of from 0 to 3, provided that when $R^7$ is $COR^g$ or $COOR^g$, $R^1$ is not phenyl;

all other variables are as previously defined; or a pharmaceutically acceptable salt thereof.

A second embodiment of the invention is a compound of formula (I), wherein $R^7$ is selected from H, $R^g$ and $(CH_2)_{1-4}OR^g$;

q is an integer of from 0 to 3; and all other variables are as defined in the first embodiment; or a pharmaceutically acceptable salt thereof.

A third embodiment of the invention is a compound of formula (I), wherein $R^1$ is selected from phenyl, mono-, di- or tri-substituted phenyl and pyridyl, wherein the substituents on the phenyl are independently selected from F, Cl, Br, I, CN and $R^a$; and all other variables are as defined in the first embodiment; or a pharmaceutically acceptable salt thereof.

A fourth embodiment of the invention is a compound of formula (I), wherein $R^1$ is selected from phenyl, mono-, di- or tri-substituted phenyl and pyridyl, wherein the substituents on the phenyl are independently selected from F, CN and $R^a$; and all other variables are as defined in the first embodiment; or a pharmaceutically acceptable salt thereof.

A fifth embodiment of the invention is a compound of formula (I), wherein $R^1$ is selected from phenyl, mono-, di- or tri-substituted phenyl and pyridyl, wherein the substituents on the phenyl are independently selected from F, CN and $R^a$;

m is an integer from 0 to 1;

L is selected from $(CHR^2)_k$, $CR^8C^9(CH_2)_{k-1}$, $(CH_2)_{k-1}CR^8R^9$, and $CH_2CR^8R^9CH_2$;

k is 2 or 3;

each X is independently selected from F, CN and $R^h$; and all other variables are as defined in the first embodiment; or a pharmaceutically acceptable salt thereof A first class of the invention is a compound of Formula (II):

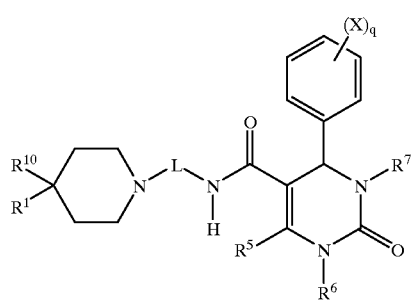

(II)

wherein $R^1$ is selected from phenyl, mono-, di- or tri-substituted phenyl, pyridyl, and mono-, di-, or tri-substituted pyridyl, wherein the substituents on the phenyl or the pyridyl are independently selected from F, Cl, Br, I, CN, $CF_3$ and $R^a$;

$R^{10}$ is selected from H, OH, CN, $R^b$ and $OR^b$;

L is selected from $(CH_2)_k$, $(CHR^2)_k$, $CR^8R^9(CH_2)_{k-1}$, $(CH_2)_{k-1}CR^8R^9$, $CH_2CR^8R^9CH_2$, $CH_2CH_2CR^8R^9CH_2$, and $CH_2CR^8R^9CH_2CH_2$;

$R^2$ is $R^c$;

k is an integer of from 2 to 4;

$R^5$ is selected from H, $R^e$, and $(CH_2)_{1-4}OR^e$;

$R^6$ is selected from H and $R^f$;

$R^7$ is selected from H, $R^g$, $(CH_2)_{1-4}OR^g$, $C(=O)OR^g$ and $C(=O)R^g$;

$R^8$ and $R^9$ are each independently $R^c$;

each X is independently selected from F, Cl, Br, I, CN and $R^h$;

$R^a$, $R^c$, $R^e$, $R^f$, $R^g$ and $R^h$ are each independently selected from $C_1$ to $C_4$ alkyl;

$R^b$ is selected from $C_1$ to $C_6$ alkyl and $C_3$ to $C_7$ cyclic alkyl;

and q is an integer of from 0 to 3, provided that when $R^7$ is $COR^g$ or $COOR^g$, $R^1$ is not phenyl; or a pharmaceutically acceptable salt thereof.

A second class of the invention is a compound of Formula (II) wherein $R^1$ is selected from phenyl, mono-, di- or tri-substituted phenyl and pyridyl, wherein the substituents on the phenyl are independently selected from F, Cl, Br, I, CN, $CF_3$ and $R^a$;

$R^5$ is selected from H and $R^e$; and all other variables are as defined in the first class; or a pharmaceutically acceptable salt thereof.

A third class of the invention is a compound of Formula (III):

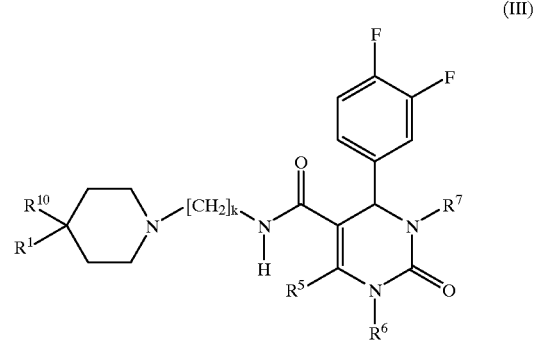

wherein $R^1$ is

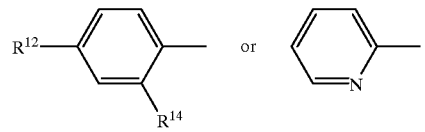

wherein $R^{12}$ and $R^{14}$ are each independently selected from H, F, Cl, Br, I, CN, $CF_3$ and $C_1$ to $C_4$ alkyl;

$R^{10}$ is selected from H, OH, and $R^b$;

k is an integer of from 2 to 4;

$R^5$ is selected from H, $R^e$ and $(CH_2)_{1-4}OR^e$;

$R^6$ is selected from H, methyl and ethyl;

$R^7$ is selected from H, $R^g$, $(CH_2)_qOR^9$, $C(=O)OR^g$ and $C(=O)R^g$; provided that when $R^{12}$ and $R^{14}$ are both H, $R^7$ is neither $C(=O)OR^g$ nor $C(=O)R^g$;

$R^b$, $R^e$ and $R^g$ are each independently selected from $C_1$ to $C_4$ alkyl; or a pharmaceutically acceptable salt thereof.

Illustrative of the invention is a compound of Formula (III) wherein $R^{12}$ and $R^{14}$ are each independently selected from H, F, CN and $C_1$ to $C_4$ alkyl;

k is an integer of from 2 to 3;

$R^5$ is selected from H, methyl, ethyl, and $CH_2OCH_3$;

$R^7$ is selected from H, methyl, ethyl, C(=O)OCH₃, and C(=O)CH₃; provided that when $R^{12}$ and $R^{14}$ are both H, $R^7$ is neither C(=O)OCH₃ nor C(=O)CH₃; and all other variables are as defined in the third class; or a pharmaceutically acceptable salt thereof.

Also illustrative of the invention is a compound of Formula (III) wherein $R^7$ is selected from H, methyl and ethyl; and all other variables are as defined in the immediately preceding paragraph; or a pharmaceutically acceptable salt thereof.

Exemplifying the invention is a compound selected from:

(4R)-4-(3,4-Difluorophenyl)-6methoxymethyl-2-oxo-1,2,3,4-tetrahydro-pyrimidine-5-carboxylic acid {3-[4(2-cyano-4-fluorophenyl)-piperidin-1-yl]-propyl}-amide;

(4R)-4-(3,4-Difluorophenyl)-6-methyl-2-oxo-1,2,3,4-tetrahydro-pyrimidine-5-carboxylic acid {3-[4-(2-cyano-4-fluorophenyl)-piperidin-1-yl]-propyl}-amide;

(4R)-4-(3,4-Difluorophenyl)-6-methoxymethyl-2-oxo-1,2,3,4-tetrahydro-pyrirmidine-5-carboxylic acid {3-[4-(2-cyanophenyl)-piperidin-1-yl]-propyl}-amide Hydrochloride.

(4R)-4-(3,4-Difluorophenyl)-6-methyl-2-oxo-1,2,3,4-tetrahydro-pyrimidine-5-carboxylic acid {3-[4-(2-cyanophenyl)-piperidin-1-yl]-propyl}-amide;

(4R)-4-(3,4-Difluorophenyl)-6methoxymethyl-2-oxo-1,2,3,4-tetrahydro-pyrimidine-5-carboxylic acid {3-[4-(4-fluorophenyl)-4-hydroxy-piperidin-1-yl]-propyl}-amide.

(4R)-4-(3,4-Difluorophenyl)-6-methyl-2-oxo-1,2,3,4-tetrahydro-pyrimidine-5-carboxylic acid {3-[4-(4-fluorophenyl)-4-hydroxy-piperidin-1-yl]-propyl}-amide;

(4R)-4-(3,4-Difluorophenyl)-6methoxymethyl-2-oxo-1,2,3,4-tetrahydro-pyrimidine-5-carboxylic acid [3-(3',4',5',6'-tetrahydro-2'H-[2,4']bipyridinyl-1'-yl)-propyl]-amide dihydrochloride.

(4R)-4-(3,4-Difluorophenyl)-6-methyl-2-oxo-1,2,3,4-tetrahydro-pyrimidine-5-carboxylic acid [3-(3',4',5',6'-tetrahydro-2'H-[2,4']bipyridinyl-1'-yl)-propyl]-amide;

(–)-4-(3,4-Difluorophenyl)-2-oxo-1,2,3,4-tetrahydro-pyrimidine-5-carboxylic acid {3-[4-(2-cyanophenyl)piperidin-1-yl]-propyl}-amide;

(–)-4-(3,4-Difluorophenyl)-2-oxo-1,2,3,4-tetrahydro-pyrimidine-5-carboxylic acid {3-[4-(4-fluorophenyl)-piperidin-1-yl]-propyl}-amide;

(–)-4-(3,4-Difluorophenyl)-6-methyl-2-oxo-1,2,3,4-tetrahydro-pyrimidine-5-carboxylic acid [3-[4-(4-fluorophenyl)-piperidin-1-yl]-propyl]-amide;

(–)-4-(3,4-Difluorophenyl)-6-methoxymethyl-2-oxo-1,2,3,4-tetrahydro-pyrimidine-5-carboxylic acid {3-[4-(4-fluorophenyl)-pipexidin-1-yl]-propyl}-amide;

(–)-4-(3,4-Difluorophenyl)-2-oxo-1,2,3,4-tetrahydro-pyrimidine-5-carboxylic acid {3-[4-(4-fluorophenyl)-4-hydroxy-piperidin-1-yl]-propyl}-amide;

(–)-4-(3,4-Difluorophenyl)-2-oxo-1,2,3,4-tetrahydro-pyrimidine-5-carboxylic acid {3-[4-(2-cyano-4-fluorophenyl)-piperidin-1-yl]-propyl}-amide;

(–)-4-(3,4-Difluorophenyl)-2-oxo-1,2,3,4-tetrahydro-pyrimidine-5-carboxylic acid [3-(3',4',5',6'-tetrahydro-2'H-[2,4']bipyridinyl-1'-yl)-propyl]-amide;

(–)-4-(3,4-Difluorophenyl )-2-oxo-1,2,3,4-tetrahydro-pyrimidine-5-carboxylic acid {3-[4-cyano-4-(fluorophenyl)-piperidin-1-yl]-propyl}-amide;

(–)-4-(3,4-Difluorophenyl)-6-methyl-2-oxo-1,2,3,4-tetrahydro-pyrimidine-5-carboxylic acid {3-[4-cyano-4-(4-fluorophenyl)-piperidin-1-yl]-propyl}-amide;

(–)-4-(3,4-Difluorophenyl)-2-oxo-1,2,3,4-tetrahydropyrimidine-5-carboxylic acid {3-[4-cyano-4-(2-cyanophenyl)-piperidin-1-yl]-propyl}-amide;

4-(3,4-Difluorophenyl)-6-methyl-2-oxo-1,2,3,4-tetrahydropyrimidine-5-carboxylic acid {3-[4-cyano-4-(2-cyanophenyl)-piperidin-1-yl]-propy}-amide;

4-(3,4-Difluorophenyl)-1-methyl-2-oxo-1,2,3,4-tetrahydropyrimidine-5-carboxylic acid {3-[4-cyano-4-(2,4-difluorophenyl)-piperidin-1-yl]-propyl}-amide;

(+)-4-(3,4-Difluorophenyl)-1-methyl-2-oxo-1,2,3,4-tetrahydro-pyrimidine-5-carboxylic acid {3-[4-cyano-4-(4-fluorophenyl)-piperidin-1-yl]-propyl}-amide;

4-(3,4-Difluorophenyl)-1-methyl-2-oxo-1,2,3,4-tetrahydropyrimidine-5-carboxylic acid {3-[4-(4-fluorophenyl)-piperidin-1-yl]-propyl}-amide;

4-(3,4-Difluorophenyl)-1,3-dimethyl-2-oxo-1,2,3,4-tetrahydro-pyrimidine-5-carboxylic acid {3-[4-cyano-4-(4-fluorophenyl)-piperidin-1-yl]-propyl}-amide;

4-(3,4-Difluorophenyl)-1,3-dimethyl-2-oxo-1,2,3,4-tetrahydro-pyrimidine-5-carboxylic acid {3-[4-(2-cyano-4-fluorophenyl)-piperidin-1-yl]-propyl}-amide;

4-(3,4-Difluorophenyl)-1,3-dimethyl-2-oxo-1,2,3,4-tetrahydro-pyrimidine-5-carboxylic acid {3-[4-(4-fluorophenyl)-piperidin-1-yl]-propyl}-amide;

4-(3,4-Difluorophenyl)-1,3-dimethyl-2-oxo-1,2,3,4-tetrahydro-pyrimidine-5-carboxylic acid {3-[4-cyano-4-(2,4-difluorophenyl)-piperidin-1-yl]-propyl}-amide;

4-(3,4-Difluorophenyl)-1-methyl-2-oxo-1,2,3,4-tetrahydro-pyrimidine-5-carboxylic acid {3-[4-(4-fluorophenyl)-4-hydroxy-piperidin-1-yl]-propyl}-amide;

4-(3,4-Difluorophenyl)-1-methyl-2-oxo-1,2,3,4-tetrahydro-pyrimidine-5-carboxylic acid {3-[4-(2-cyanr4-fluorophenyl)piperidin-1-yl]-propyl}-amide;

(–)-4-(3,4-Difluorophenyl)-1-methyl-2-oxo-1,2,3,4-tetrahydro-pyrimidine-5-carboxylic acid {3-[4-cyano-4-(4-fluorophenyl)pipendin-1-yl]-propyl}-amide;

4-(3,4-Difluorophenyl)-1-methyl-2-oxo -1,2,3,4-tetrahydro-pyrimidine-5-carboxylic acid {3-[2-cyano-4-fluorophenyl)-4-cyano-piperidin-1-yl]-propyl}amine;

4-(3,4-Difluorophenyl)-1,3-dimethyl-2-oxo-1,2,3,4-tetrahydro-pyrimidine-5- carboxylic acid {3-[2-cyano-4-fluorophenyl)-4-cyanopiperidin-1-yl]-propyl}amine;

4-(3,4-Difluorophenyl)-1,6-dimethyl-2-oxo -1,2,3,4-tetrahydro-pyrimidine-5-carboxylic acid {3-[2-cyano-4-fluorophenyl)-piperidin-1-yl]-propyl}amine;

4-(3,4-Difluorophenyl)-1,6-dimethyl-2-oxo-1,2,3,4-tetrahydro-pyrimidine-5-carboxylic acid {3-[4-(4-fluorophenyl)-piperidine-1-yl]-propyl}-amide;

(4R)-4-(3,4-Difluorophenyl)-1,6-dimethyl-2-oxo-1,2,3,4-tetrahydro-pyrimidine-5-carboxylic acid {3-[4-(4-fluorophenyl)-4-cyano-piperidine-1-yl]-propyl}-amide;

(4R)-4-(3,4-Difluorophenyl)-1,6-dimethyl-2-oxo-1,2,3,4-tetrahydro-pyrimidine-5-carboxylic acid {3-[4-(2,4-difluorophenyl)-4-cyano-piperidine-1-yl]-propyl}-amide;

4-(3,4-Difluorophenyl)-1,3,6-tzimethyl-2-oxo-1,2,3,4-tetrahydro-pyrimidine-5-carboxylic acid-{3-[4-(4-fluorophenyl)-piperidin-1-yl]-propyl}-amide;

(4R)-4-(3,4-Difluorophenyl)-1,3,6-trimethyl-2-oxo-1,2,3,
4-tetrahydro-pyrimidine-5-carboxylic acid {3-[4-(4-
fluorophenyl)-4-cyano-piperidin-1-yl]-propyl}-amide;

(4R)-4-(3,4-Difluorophenyl)-1,3,6-trimethyl-2-oxo-1,2,3,
4-tetrahydro-pyrimidine-5-carboxylic acid {3-[4-(2,4-
difluorophenyl)-4-cyano-piperidine-1-yl]-propyl}-
amide;

4-(3,4-Difluorophenyl)-1,6-dimethyl-3-acetyl-2-oxo-1,2,
3,4-tetrahydro-pyrimidine-5-carboxylic acid {3-[4-(4-
fluorophenyl)-piperidin-1-yl]-propyl}-amide;

4-(3,4-Difluorophenyl)-1,6-dimethyl-3-carbomethoxy-2-
oxo-1,2,3,4-tetrahydro-pyrimidine-5-carboxylic acid
{3-[4-(4-fluorophenyl)-piperidine-1-yl]-propyl}amide;

(−)-4-(3,4-Difluorophenyl)-3,6-dimethyl-2-oxo-1,2,3,4-
tetrahydro-pyrimidine-5-carboxylic acid {3-[4-(2-
cyano-4-fluorophenyl)-piperidin-1-yl]-propyl}-amide;

(−)-4-(3,4-Difluorophenyl)-3,6-dimethyl-2-oxo-1,2,3,4-
tetrahydro-pyrimidine-5-carboxylic acid {3-[4-cyano-
4-(4-fluorophenyl)-piperidin-1-yl]-propyl}-amide;

(−)-4-(3,4-Difluorophenyl)-3,6-dimethyl-2-oxo-1,2,3,4-
tetrahydro-pyrimidine-5-carboxylic acid {3-[4-cyano-
4-(2,4-difluorophenyl)-piperidin-1-yl]-propyl}-amide;

(−)-4-(3,4-Difluorophenyl)-3,6-dimethyl-2-oxo-1,2,3,4-
tetrahydro-pyrimidine-5-carboxylic acid {3-[4-(4-
fluorophenyl)-piperidin-1-yl]-propyl}-amide;

(−)-4-(3,4-Difluorophenyl)-1,6-dtimethyl-2-oxo-1,2,3,4-
tetrahydro-pyrimidine-5-carboxylic acid {3-[4-(2-
cyano-4-fluorophenyl)-piperidin-1-yl]-propyl}-amide;

(±)-4-(3,4-Difluorophenyl)-1,3,6-trimethyl-2-oxo-1,2,3,
4-tetrahydro-pyrimidine-5-carboxylic acid {3-[4-(2-cyano-
4-fluorophenyl)-piperidin-1-yl]-propyl}-amide;

(−)-4-(3,4-Difluorophenyl)-1,3,6-trimethyl-2-oxo-1,2,3,
4-tetrahydro-pyrimidine-5-carboxylic acid {3-[4-(2-
cyano-4-fluorophenyl)-piperidin-1-yl]-propyl}-amide;

(+)-4-(3,4-Difluorophenyl)-1,3,6-trimethyl-2-oxo-1,2,3,
4-tetrahydro-pyrimidine-5-carboxylic acid {3-[4-(2-
cyano-4-fluorophenyl)-piperidin-1-yl]-propyl}-amide;

(4R)-4-(3,4-Difluorophenyl)-6methoxymethyl-2-oxo-1,
2,3,4-tetrahydro-pyrimidine-5-carboxylic acid {3-[4-
cyano-4-(4-fluorophenyl)-piperidin-1-yl]-propyl}-
amide;

(4R)-4-(3,4-Difluorophenyl)-6methoxymethyl-2-oxo-1,
2,3,4-tetrahydro-pyrimidine-5-carboxylic acid {3-[4-
cyano-4-(2,4-difluorophenyl)-piperidin-1-yl]-propyl}-
amide;

(4R)-4-(3,4-Difluorophenyl)-6-methoxymethyl-1-
methyl-2-oxo-1,2,3,4-tetrahydro-pyzimidine-5-
carboxylic acid {3-[4-cyano-4-(4-fluorophenyl)-
piperidin-1-yl]-propyl}-amide;

4-(3,4-Difluorophenyl)-6-methoxymethyl-1-methyl-2-
oxo-1,2,3,4-tetrahydro-pyrimidine-5-carboxylic acid
{3-[4-(4-fluorophenyl)-piperidin-1-yl]-propyl}-amide;

and pharmaceutically acceptable salts thereof.

In a preferred embodiment of the invention, the compound is Compound A, which is

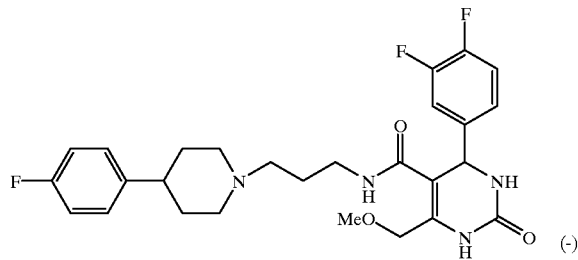

or a pharmaceutically acceptable salt thereof.

Another aspect of the invention is a pharmaceutical composition comprising a therapeutically effective amount of any of the compounds described above and a pharmaceutically acceptable carrier. One embodiment is a pharmaceutical composition made by combining any of the compounds described above and a pharmaceutically acceptable carrier. Another embodiment is a process for making a pharmaceutical composition comprising combining any of the compounds described above and a pharmaceutically acceptable carrier.

Still another aspect of the invention is the pharmaceutical composition described in the preceding paragraph further comprising a therapeutically effective amount of a testosterone 5-alpha reductase inhibitor. In a preferred embodiment, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor) or a dual type 1 and type 2 testosterone 5-alpha reductase inhibitor. In a more preferred embodiment, the testosterone 5-alpha reductase inhibitor is a type 2 testosterone 5-alpha reductase inhibitor. Most preferably, the testosterone 5-alpha reductase inhibitor is finasteride.

A further aspect of the invention is a method of treating benign prostatic hyperplasia in a subject in need thereof which comprises administering to the subject a therapeutically effective amount of any of the compounds (or any of the compositions) described above. In one embodiment of the method of treating BPH, the compound (or composition) additionally does not cause a fall in blood pressure at dosages effective to alleviate BPH. In another embodiment of the method of treating BPH, the compound is administered in combination with a testosterone 5-alpha reductase inhibitor. A preferred testosterone 5-alpha reductase inhibitor for use in the method is finasteride.

Yet another aspect of the invention is a method of inhibiting contraction of prostate tissue or relaxing lower urinary tract tissue in a subject in need thereof which comprises administering to the subject a therapeutically effective amount of any of the compounds (or any of the compositions) described above. In one embodiment of the method of inhibiting contraction of prostate tissue or relaxing lower urinary tract tissue, the compound (or composition) additionally does not cause a fall in blood pressures at dosages effective to inhibit contraction of prostate tissue. In another embodiment, the compound (or composition) is administered in combination with a testosterone 5-alpha reductase inhibitor; preferably, the testosterone 5-alpha reductase inhibitor is finasteride.

A further aspect of the invention is a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see K.A. Vatz, *Headache*, Vol. 37, 107–108 (1997)) and cardiac arrhythmia.

An additional aspect of the invention is the use of any of the compounds described above in the preparation of a medicament for: a) treating benign prostatic hyperplasia; b) relaxing lower urinary tract tissue; or c) inhibiting contraction of prostate tissue; in a subject in need thereof.

A further aspect of the invention is the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

These and other embodiments, aspects and features of the present invention are either further described in or will be apparent from the ensuing description, examples and appended claims.

DETAILED DESCRIPTION OF THE INVENTION

The compounds of the invention are 5-carboxamide substituted dihydropyrimidin-2-ones in which the carboxamide substituent contains a saturated, nitrogen-containing heterocyclic ring. These may be generally referred to as "reverse dihydropyrimidinones" to distinguish them from dihydropyrimidin-2-ones having analogous carboxamide substituents on one of the pyrimidinone nitrogens instead of the ring-5 carbon atom. The compound of the present invention is a compound of Formula (I) as set forth above. In Formula (I), $R^1$ is suitably selected from phenyl, substituted phenyl, pyridyl and substituted pyridyl. $R^1$ is typically selected from phenyl, mono-, di-, or tri-substituted phenyl, pyridyl and mono-, di- or tri-substituted pyridyl. In other embodiments, $R^1$ is selected from phenyl, mono-, di or tri-substituted phenyl, and pyridyl; or from phenyl, mono- or di-substituted phenyl, and pyridyl. It is understood that when $R^7$ is either $C(=O)OR^g$ or $C(=O)R^g$, $R^1$ is not phenyl. In other words, when $R^7$ is either $C(=O)OR^g$ or $C(=O)OR^g$, $R^1$ is selected from substituted phenyl, pyridyl, and substituted pyridyl.

The substituents on the substituted phenyl or substituted pyridyl are each independently selected from F, Cl, Br, I, $(CH_2)_{0-4}CF_3$, CN, $NO_2$, $R^a$ and $OR^a$. More typically the substituents are independently selected from F, Cl, Br, I, CN, $R^a$, $OR^a$, and $(CH_2)0-2CF_3$. In other embodiments, the substituents are selected from F, CN, $R^a$, $OR^a$, and $(C_{112})0-2CF_3$; or from F, CN, $R^a$, and $CF_3$; or from F and CN.

In a preferred embodiment, $R^1$ is

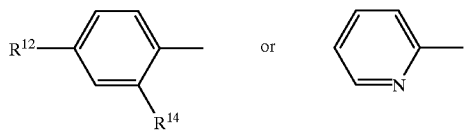

wherein $R^{12}$ and $R^{14}$ are each independently selected from H, F, Cl, Br, C, CN, $C_1$ to $C_4$ alkyl and $CF_3$. In other embodiments $R^{12}$ and $R^{14}$ are each independently selected from H, F, CN, $C_1$ to $C_4$ alkyl and $CF_3$; or from H, F, CN and $C_1$ to $C_4$ alkyl; or from H, F, CN, methyl and ethyl; or from H, F, CN; or from H and F. It is understood that $R^8$ and $R^9$ are not both H, when $R^7$ (defined elsewhere) is either $C(=O)OR^g$ or $C(=O)R^g$.

$R^{10}$ is suitably selected from H, OH, CN, $R^b$, $OR^b$, $(CH_2)_{1-4}OR^b$ and $(CH_2)_{0-4}CF_3$. $R^{10}$ is typically selected from H, OH, CN, $R^b$, $OR^b$, $(CH_2)_{1-2}OR^b$ and $(CH_2)_{0-1}CF_3$. In other embodiments, $R^{10}$ is selected from H, OH, CN, $R^b$, $OR^b$ and $CF_3$ or from H, OH, CN, $R^b$ and $OR^b$; or from H, OH, $R^b$, and $OR^b$; or from H and CN; or from H and OH.

m is an integer from 0 to 2; preferably an integer from 0 to 1 (i.e., the heterocyclic ring is either pyrrolidinyl or piperidinyl); and more preferably is 1 (i.e., the ring is piperidinyl).

L is selected from $(CH_2)_k$, $(CHR^2)_k$, $CR^8R^9(CH_2)_{k-1}$, $(CH_2)_{k-1}OCR^8R^9$, $CH_2CR^8R^9CH_2$, $CH_2CH_2CR^8R^9CH_2$, and $CH_2CR^8R^9CH_2CH_2$. In a preferred embodiment L is selected from $(CH_2)_k$ and $(CHR^2)_k$. In a more preferred embodiment, L is $(CH_2)_k$.

$R^2$ is selected from $R^c$ and $(CH_2)_{0-4}CF_3$. More typically $R^2$ is $R^c$. In other embodiments, $R^2$ is selected from $R^c$ and $(CH_2)_{0-2}CF_3$; or from $R^c$ and $CF_3$.

$R^8$ and $R^9$ are each independently selected from $R^c$ and $(CH_2)_{0-4}CF_3$. More typically $R^8$ and $R^9$ are independently $R^c$. In other embodiments, $R^8$ and $R^9$ are independently selected from $R^c$ and $(CH_2)_{0-4}CF_3$; or from $R^c$ and $CF_3$.

k is suitably an integer of from 2 to 4, and is typically an integer of from 2 to 3. In one embodiment, k=3.

$R^4$ is suitably selected from H, $R^d$ and $(CH_2)_{0-4}CF_3$, and is typically selected from H, $R^d$ and $(CH_2)_{0-2}CF_3$. In other embodiments, $R^4$ is selected from H, $R^d$ and $CF_3$; or from H and $R^d$. In a preferred embodiment $R^4$=H.

$R^5$ is suitably selected from H, $R^e$, $(CH_2)_{1-4}OR^e$ and $(CH_2)_{1-4}CF_3$; and is typically selected from H, $R^e$, $(CH_2)_{1-2}OR^e$ and $(CH_2)_{1-2}CF_3$. In other embodiments, $R^5$ is selected from H, $R^e$ and $(CH_2)_{1-4}OR^e$; or from H and $R^e$.

$R^6$ is suitably selected from H and $R^f$.

$R^7$ is suitably selected from H, $R^g$, $(CH_2)_{1-4}OR^g$, $C(=O)OR^9$, $C(=O)R^g$ and $(CH_2)_{0-4}CF_3$; and is typically selected from H, $R^g$, $(CH_2)_{1-2}OR^g$, $C(=O)OR^9$, $C(=O)R^g$ and $(CH_2)_{0-4}CF_3$. In other embodiments, $R^7$ is selected from H, $R^g$, $(CH_2)_{1-4}OR^g$, $C(=O)OR^g$ and $C(=O)R^g$; or from H, $R^g$ and $(CH_2)_{1-4}OR^g$; or H and $R^g$.

Each X is independently selected from F, Cl, Br, I, CN and $R^h$. In other embodiments, each X is independently selected from F, CN and $R^h$; or from F and CN. In a preferred embodiment each X is F.

q is an integer of from 0 to 4, and preferably 0 to 3. In other embodiments, q is 1 or 2; or is 2.

$R^a$, $R^d$, $R^c$, $R^f$, $R^g$ and $R^h$ are suitably each independently selected from $C_1$ to $C_6$ alkyl, and typically are each independently selected from $C_1$ to $C_4$ alkyl. In a preferred embodiment, each of $R^a$, $R^d$, $R^e$, $R^f$, $R^g$ and $R^h$ is independently selected from methyl and ethyl.

$R^b$ and $R^c$ are suitably each independently selected from $C_1$ to $C_6$ alkyl and $C_3$ to $C_7$ cyclic alkyl; and typically selected from $C_1$ to $C_4$ alkyl and $C_3$ to $C_6$ cyclic alkyl. In other embodiments, $R^b$ and $R^c$ are each independently selected from $C_1$ to $C_6$ alkyl and $C_3$ to $C_7$ cycloalkyl; or from $C_1$ to $C_4$ alkyl and $C_3$ to $C_6$ cycloalkyl; or from $C_1$ to $C_4$ alkyl.

The term "$C_1$ to $C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$ to $C_4$ alkyl" means n-, iso-, sec- and t-butyl, n- and isopropyl, ethyl and methyl.

The term "$C_3$ to $C_7$ cyclic alkyl" means cycloalkyl rings having from 3 to 7 carbon atoms (i.e., cyclopropyl, cyclobutyl, cyclopentyl, cyclohexyl, cycloheptyl or cyclooctyl) optionally substituted with one or more $C_1$ to $C_6$ alkyl groups as defined above.

The term "aryl" as used herein, except where otherwise specifically defined, refers to phenyl or substituted phenyl.

The term "substituted" includes multiple degrees of substitution by a named substituent to the extent such multiple substitution is chemically allowed. Thus, for example, "substituted phenyl" includes mono-, di- tri-, tetra- and penta-substituted phenyl groups.

The definition of any substituent or variable (e.g., X or $R^c$) at a particular location in a molecule is independent of its definitions elsewhere in that molecule. Thus, $CR^8R^9(CH_2)_{k-1}$, wherein k=2 and $R^8$ and $R^9$ are each independently $R^c$, represents

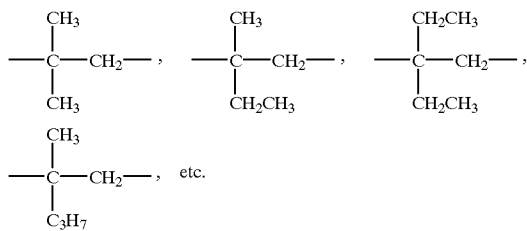

It is understood that substituents and substitution patterns on the compounds of the instant invention can be selected by one of ordinary skill in the art to provide compounds that are chemically stable and that can be readily synthesized by techniques known in the art as well as those methods set forth below.

Where multiple substituent moieties are disclosed or claimed, the substituted compound can be independently substituted by one or more of the disclosed or claimed substituent moieties, singly or plurally.

Representative compounds of the present invention exhibit high selectivity for the human alpha 1a adrenergic receptor. One implication of this selectivity is that these compounds display selectivity for lowering intraurethral pressure without substantially affecting diastolic blood pressure.

Representative compounds of this invention display sub-micromolar affinity for the human alpha 1a adrenergic receptor subtype while displaying at least ten-fold lower affinity for the human alpha 1d and alpha 1b adrenergic receptor subtypes, and many other G-protein coupled human receptors. Particular representative compounds of this invention exhibit nanomolar and subnanomolar affinity for the human alpha 1a adrenergic receptor subtype while displaying at least 30 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors). Still other representative compounds of this invention exhibit nanomolar and subnanomolar affinity for the human alpha 1a adrenergic receptor subtype while displaying at least 50 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed; e.g., treatment of BPH. For use in medicine, the salts of the compounds of this invention refer to non-toxic "pharmaceutically acceptable salts." Other salts may, however, be useful in the preparation of the compounds according to the invention or in the prepartion of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, benzenesulfonate, benzoate, bicarbonate, bisulfate, bitartrate, borate, bromide, calcium, canmsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Compounds of this invention are used to reduce the acute symptoms of BPH. Thus, compounds of this invention may be used alone or in combination with more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intra-ocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient Conventional procedures for the selection and preparation of suitable prodrug derivatives are described, for example, in Design of Prodrugs, ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "selective alpha 1a adrenergic receptor antagonist," as used herein, refers to an alpha 1a antagonist compound which is at least ten fold selective for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used a herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention includes pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" encompasses a product comprising the specified ingredients in the specified amounts, as well as any product which results, directly or indirectly, from combination of the specified ingredients in the specified amounts.

The liquid forms in which the novel compositions of the present invention may be incorporated for a ministration orally or by injection include aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

The specificity of binding of compounds showing affinity for the alpha 1a receptor is shown by comparing affinity to membranes obtained from transfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its finction. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. WO94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha 2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic finction of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range; e.g., from about 0.01 to about 1000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to about 10 mg/kg of body weight per day, and especially from about 0.001 mg/kg to about 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this invention is administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO93/23420, EP 0572166; WO 93/23050; WO93/23038; WO93/23048; WO93/23041; WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject is about 0.01 mg per subject per day to about 50 mg per subject per day in combination with an alpha 1a antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. No.'s 4,377,584 and 4,760,071 which describe dosages and formulations for 5a-reductase inhibitors.

Abbreviations used in the instant specification, particularly the Schemes and Examples, are as follows:

AcOH or HOAc=acetic acid
BCE-BOCA=bis-(2-chloroethyl)-tert-butoxycarbonylamine
$BF_3$ Et2O=boron trifluoride diethyl etherate
Boc or BOC=t-butyloxycarbonyl
$Boc_2O$=di-tert-butyl dicarbonate
DBU=1,8-diazabicyclo[5.4.0]undec-7-ene
DfBzCHO=3,4-difluorobenzaldehyde
DMF=N,N-dimethylformamide
DMSO=dimethylsulfoxide
EDC=1-(3-dimethylaminopropyl)-3-ethylcarbodiimide hydrochloride
Et=ethyl
$Et_3N$=triethylamine
EtOAc=ethyl acetate
EtOH=ethanol
HOAt=1-hydroxy-7-azabenzotriazole
HOBt=1-hydroxy benzotriazole hydrate
HPLC=high performance liquid chromatography
LDA=lithium diisopropylamide
Me=methyl
MeI=methyl iodide
MeOH=methanol
NMR=nuclear magnetic resonance
NPhCF=p-nitrophenylchoroformate
OMe=methoxy
Pd/C=palladium on carbon
TEA=triethylamine
THF=tetrahydrofuran
TLC=thin layer chromatography The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Unless otherwise indicated, all variables are as defined above.

Many of the compounds of the present invention can be prepared as outlined in Scheme 1. Reaction of 1-Boc-4- piperidone with LDA and n-phenyltrifluoromethane sulfonimide provides the 1,2,5,6-tetrahydropyridin-4-yl ester of trifluoromethane sulfonic acid which, upon reaction with aryl zinc iodide in the presence of tetrakis (triphenylphosphine) palladium provides 1-Boc-4-aryl-1,2,5,6-tetrahydropyridine which is hydrogenated to 1-Boc-4-arylpiperidine. The Boc group is then removed by reaction with HCl to form the 4-aryl piperiidinium hydrochloride. The hydrochloride is then reacted with 3-bromo-1-Boc-propylamine and TEA to provide 3-[4-aryl piperidin-1-yl]-1-Boc-propylamine, which is converted to the hydrochloride by reaction with HCl. The hydrochloride is then reacted with a 5-carboxylic acid dihydropyrimidin-2-one (e.g., 4-difluorophenyl-6-alkoxyalkyl-2-oxo-1,2,3,4-tetrahydropyrimidine-5-carboxylic acid), EDC, HOBT and TEA to obtain 5-(3-[4-arylpiperidin-1-yl]-propyl) carboxamido-1,6-dihydropyrimidin-2-one (e.g., 4-difluorophenyl-6-alkoxyalkyl-2-oxo-1,2,3,4-tetrahydropyrimidine-5-carboxylic acid [3-(4-arylpiperidin-1-yl) propyl]-amide).

Scheme 2 is a variation of Scheme 1 by which 4-aryl-hydropiperidin-1-yl substituents can be obtained. An aryl-magnesium bromide is reacted with 1-Boc-4-piperidone to obtain 1-Boc-4-aryl-4-hydroxy piperidine which is converted to the hydrochloride salt by reation with HCl. This 4-aryl-4-hydroxy hydrochloride is then reacted in the same manner as the 4-aryl piperidine hydrochloride in Scheme 1 to obtain the 5-[3-[-4-hydroxy-4-arylpiperidin-1-]-propyl] carboxamide-1,6-dihydropyridin-2-one (e.g., 4-difluorophenyl-2-oxo-1,2,3,4-tetrahydropyrimidine-5-carboxylic acid [3-(4-hydroxy-4-arylpiperidin-1-yl) propyl] amide).

Scheme 3 provides a general method for preparing the reverse dihydropyrimidinones of the invention with 4-aryl-4-cyanopiperidin-1-yl substituents. Arylacetonitrile is reacted with BCEBOCA and NaH or CsCO₃ to provide 1-Boc-4-aryl-4-cyano-piperidine, which is converted to 4-aryl-4-cyano-piperidine hydrochloride by reaction with HCl. This hydrochloride is then reacted in the same manner as the 4-arylpiperidum hydrochloride in Scheme 1 to obtain the 5-{3-[4cyano- 4-aryl-piperidin-1-yl]-propyl} carboxamide-1,6-dihydropyrimidin-2-one (e.g., 4-difluorophenyl-2-oxo-1,2,3,4-tetrahydropyrimidine-5-carboxylic acid-[3-(4-cyano-4-arylpiperidin-1-yl) propyl] amide).

Schemes 4–6 present general procedures for preparing the 5-carboxylic acid dihydropyrimidin-2-one intermediates employed in Schemes 1–3. In both Schemes 4 and 5, methyl-3,3-dimethoxypropionate is condensed with urea (or an alkylurea) and an arylaldehyde catalyzed by acetic acid, copper oxide and a Lewis acid (e.g., $BF_3 \cdot Et_2O$) to obtain 4-aryl-2-oxo-1,2,3,4-tetrahydro-pyrimidine-5-carboxylic acid methyl ester from urea (or the 1-alkyl analog from alkylurea), which is subsequently converted to the 5-carboxylic acid derivative by basic hydrolysis. Alternatively, the methyl ester can first be treated with an alkyl halide (e.g., methyl iodide) to obtain 4-aryl-3-alkyl-2-oxo-1,2,3,4-tetrahydropyrimidine-5-carboxylic acid methyl ester from urea (or the 1-alkyl analog from alkylurea), which is then hydrolyzed to the 5-carboxylic acid derivative. Scheme 4 illustrates the foregoing procedure wherein the urea is alkylurea and the arylaldehyde is 3,4-difluorobenzaldehyde. Scheme 5 illustrates the procedure using methylurea and 3,4-difluorobenzaldehyde.

Scheme 5 also includes a procedure for resolving the optical isomers, wherein the mixture of methyl ester enantiomers is reacted with LDA and NPhCF followed by R-(+) alpha methyl benzylamine to obtain the 3-(1-phenylethylcarbamoyl) diastereomers, which are separated by conventional means known in the art. The enantiomers are then obtained from the separated diastereomers first by reaction with DBU to regenerate the methyl ester, followed directly by basic hydrolysis to obtain a 4-aryl-2-oxo-1-alkyl-1,2,3,4-tetrahydropyrimidine 5-carboxylic acid enantiomer, or followed by reaction with an alkyl halide and then hydrolysis to obtain a 4-aryl-3-alkyl-2-oxo-1,2,3,4-tetrahydropyrimidine carboxylic acid enantiomer.

Scheme 6 outlines a route to a mixture of 6-alkyl-4-aryl-3-alkyl-2-oxo- and 6-alkyl-4aryl-2-oxo-1-alkyl-1,2,3,4-tetrahydropyrimidine 5-carboxylic acids by N-alkylating 4-aryl-2-methoxy-3,4-dihydropyrimidine 5-carboxylic acid methyl ester with an alkyl halide in the presence of a hydride, followed by acid hydrolysis to form the 2-oxo group, and then by basic hydrolysis to form the 5-carboxylic acid derivative.

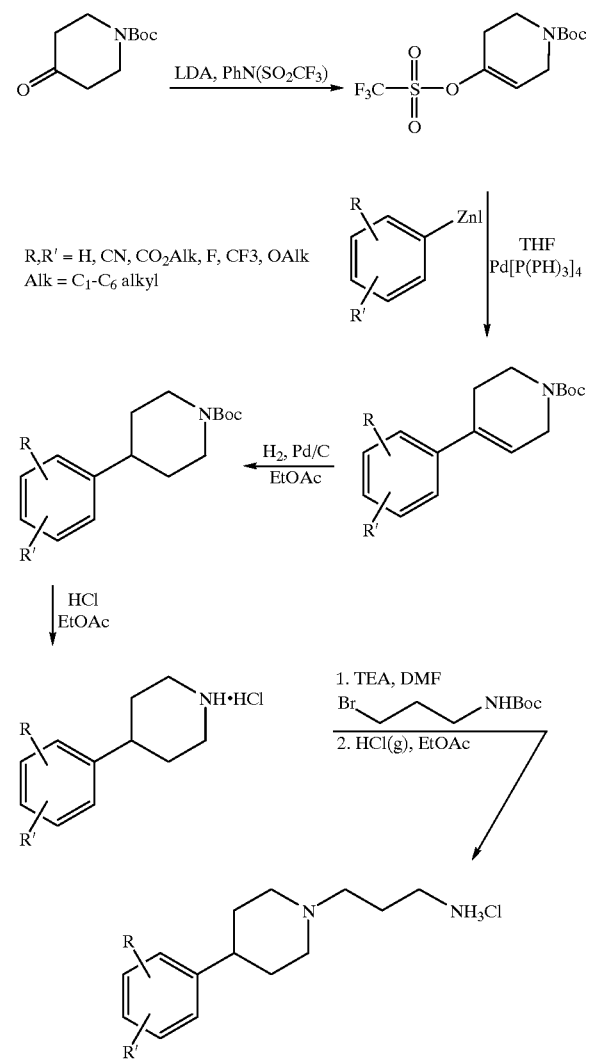

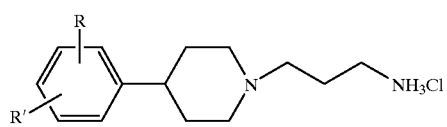
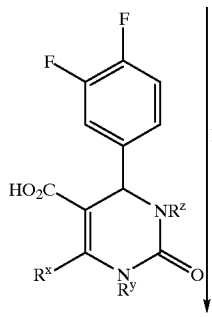
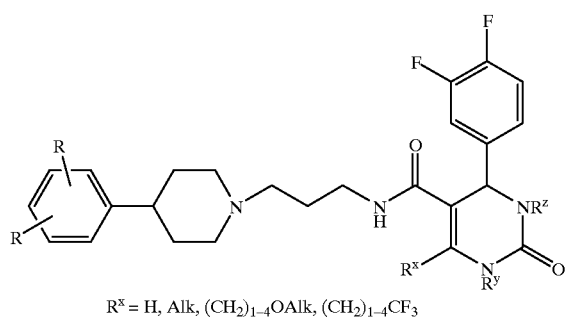
Scheme 2
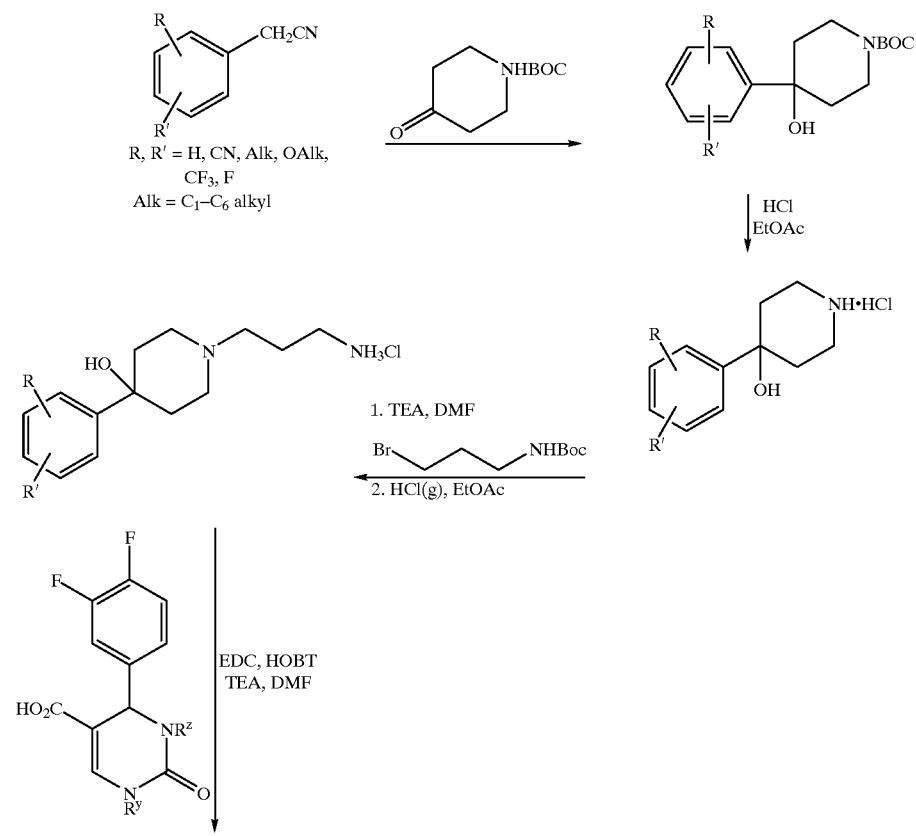

-continued
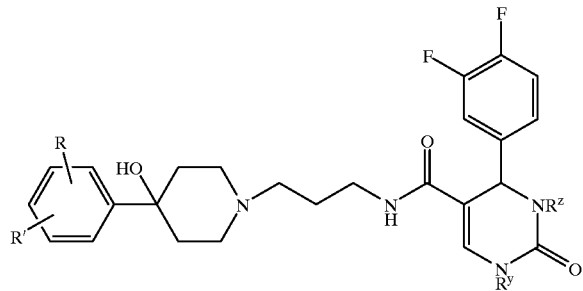
$R^y$ = H, Alk
$R^z$ =H, Alk, $(CH_2)_{1-4}$OAlk, COOAlk, C(=O)Alk
Alk = $C_1$–$C_6$ alkyl
20
25
Scheme 3
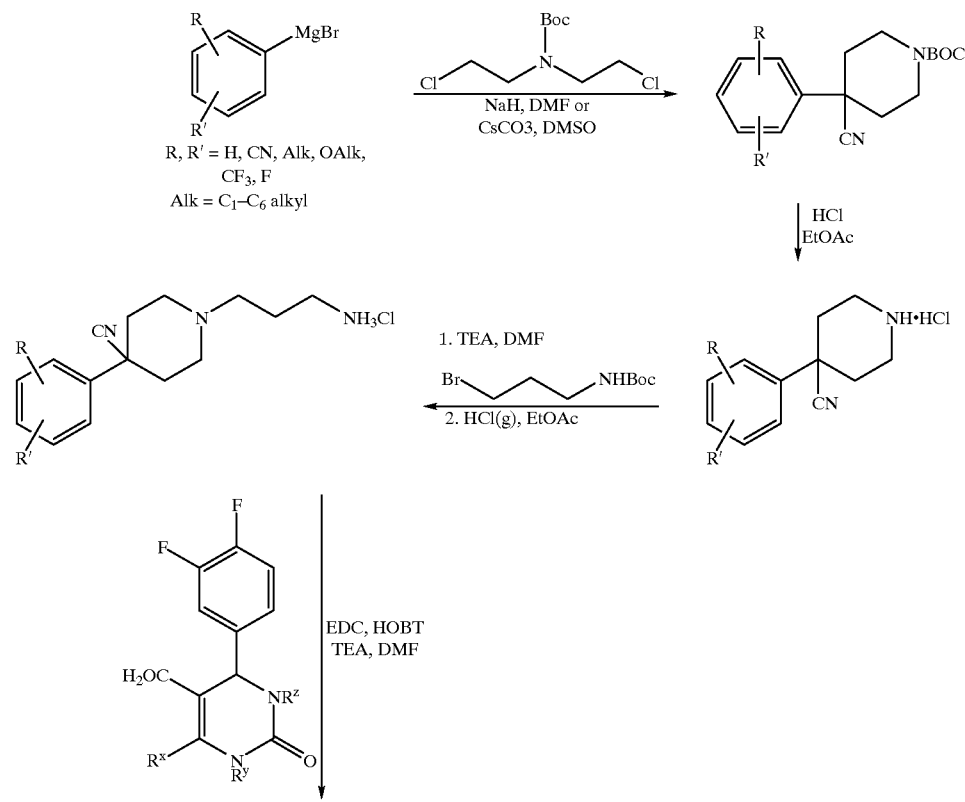

-continued
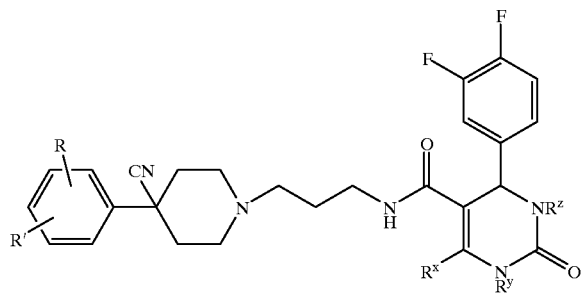
$R^x$ = H, Alk, $(CH_2)_{1-4}$OAlk, $(CH_2)_{1-4}CF_3$
$R^y$ = H, Alk
$R^z$ = H, Alk, $(CH_2)_{1-4}$OAlk, COOAlk, C(=O)Alk
Alk = $C_1-C_6$ alkyl
Scheme 4
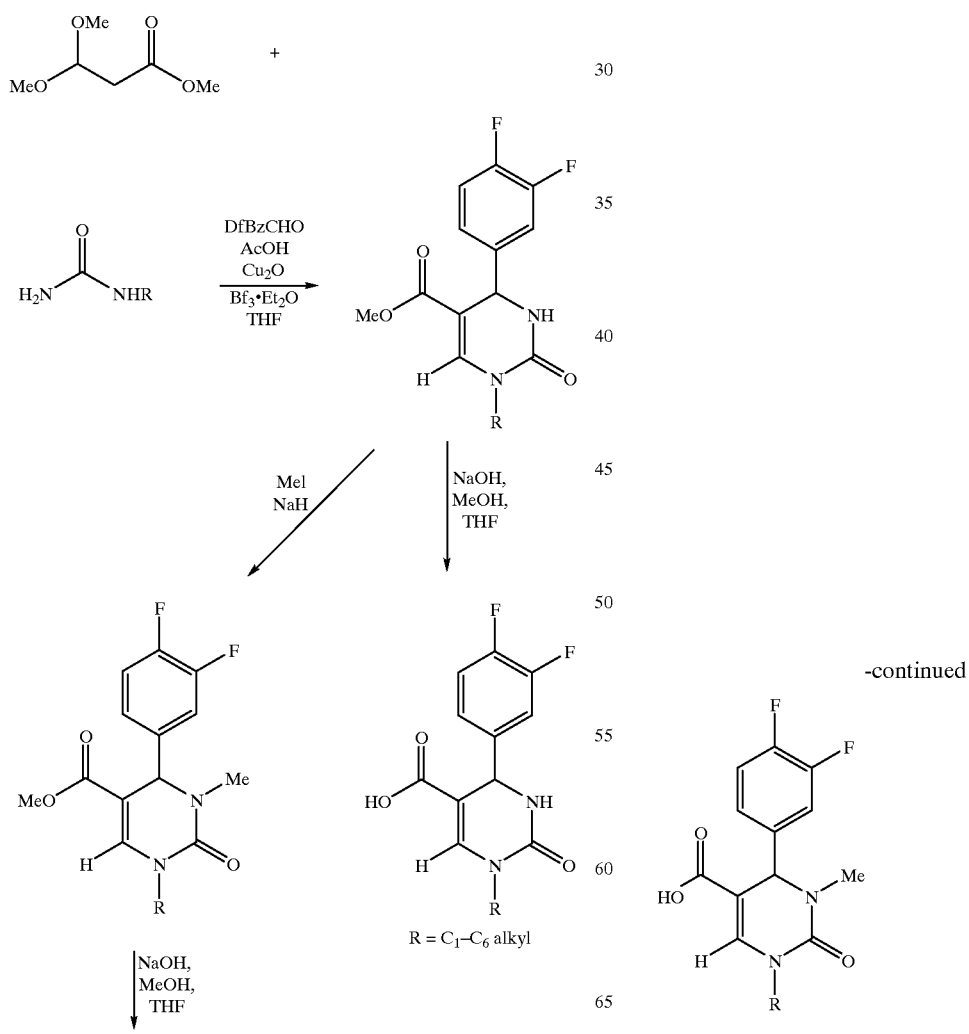
R = $C_1-C_6$ alkyl
-continued Scheme 5
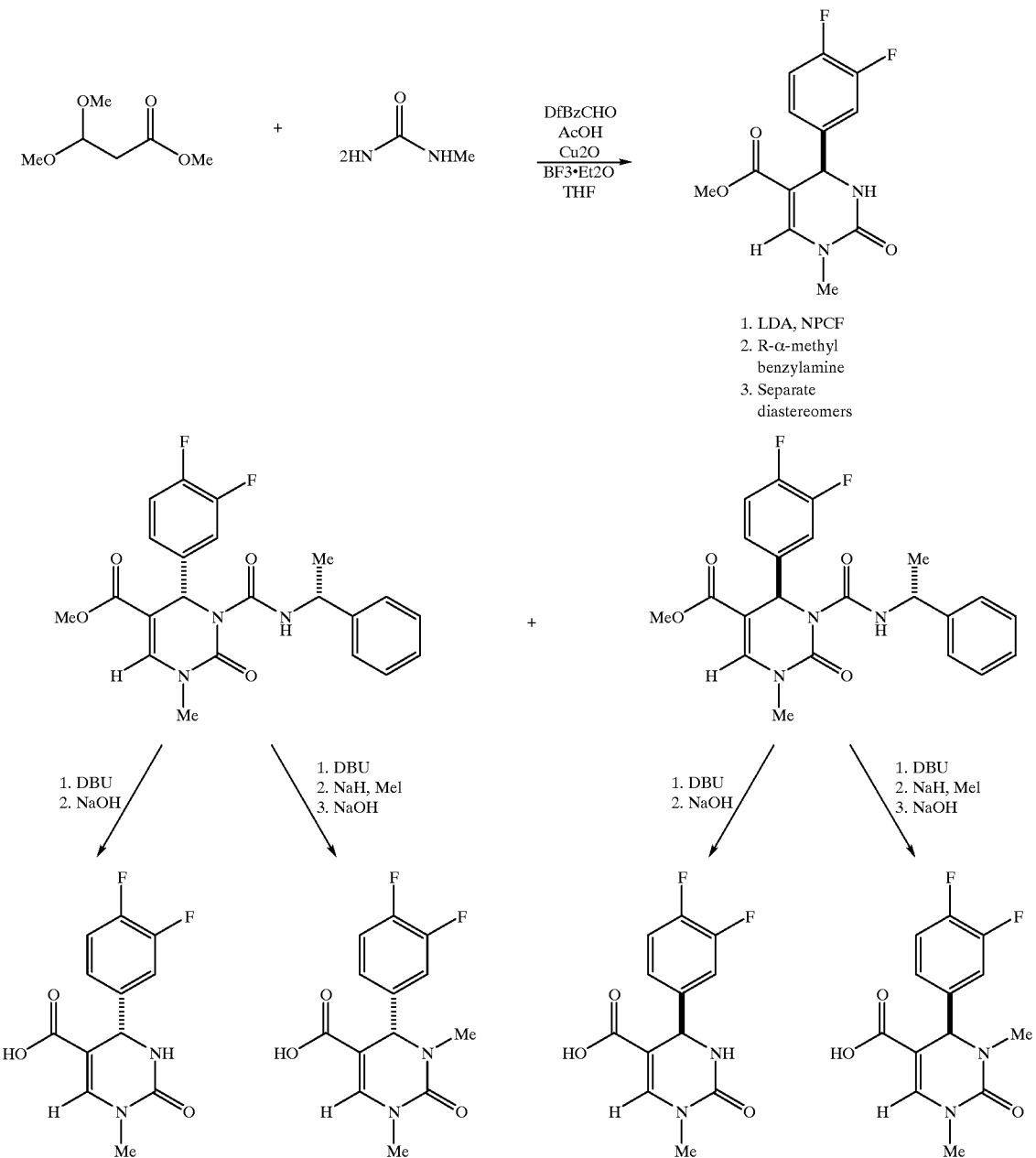
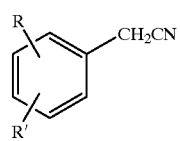
Scheme 6
R = C₁–C₆ alkly
NaH, MeI

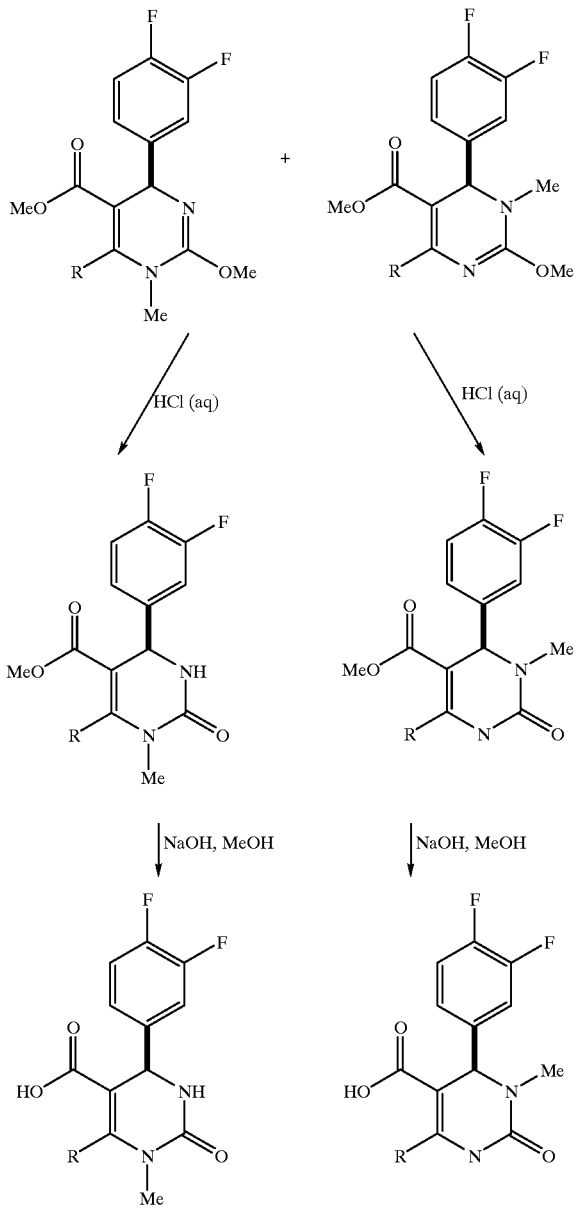

The following examples illustrate the practice of the present invention and are not to be construed as limiting the scope or spirit of the invention.

EXAMPLE 1

2-[1-(3-Aminopropyl)-piperidin-4-yl] benzonitrile Hydrochloride

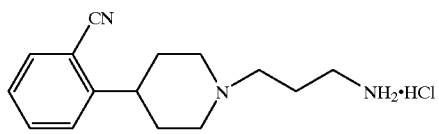

Step A. Thifluoromethanesulfonic acid[1-tert-butoxycarbonyl-(1,2,3,6-tetrahydro-pyridin-4-yl)] ester

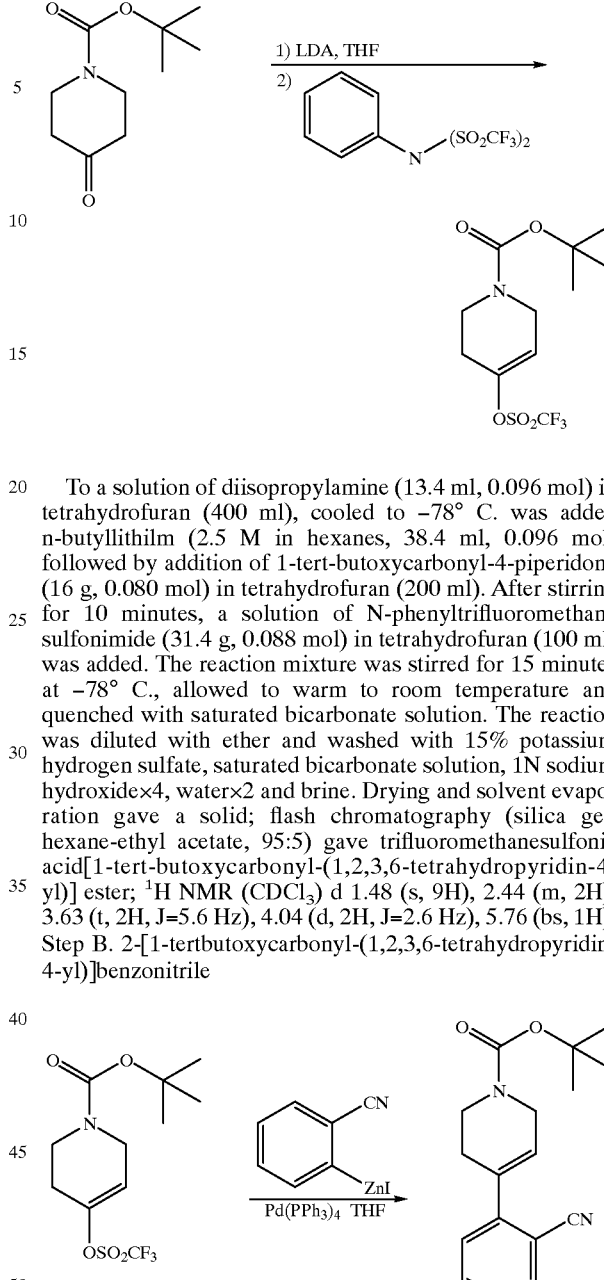

To a solution of diisopropylamine (13.4 ml, 0.096 mol) in tetrahydrofuran (400 ml), cooled to −78° C. was added n-butyllithilm (2.5 M in hexanes, 38.4 ml, 0.096 mol) followed by addition of 1-tert-butoxycarbonyl-4-piperidone (16 g, 0.080 mol) in tetrahydrofuran (200 ml). After stirring for 10 minutes, a solution of N-phenyltrifluoromethane sulfonimide (31.4 g, 0.088 mol) in tetrahydrofuran (100 ml) was added. The reaction mixture was stirred for 15 minutes at −78° C., allowed to warm to room temperature and quenched with saturated bicarbonate solution. The reaction was diluted with ether and washed with 15% potassium hydrogen sulfate, saturated bicarbonate solution, 1N sodium hydroxide×4, water×2 and brine. Drying and solvent evaporation gave a solid; flash chromatography (silica gel, hexane-ethyl acetate, 95:5) gave trifluoromethanesulfonic acid[1-tert-butoxycarbonyl-(1,2,3,6-tetrahydropyridin-4-yl)] ester; $^1$H NMR (CDCl$_3$) d 1.48 (s, 9H), 2.44 (m, 2H), 3.63 (t, 2H, J=5.6 Hz), 4.04 (d, 2H, J=2.6 Hz), 5.76 (bs, 1H).

Step B. 2-[1-tertbutoxycarbonyl-(1,2,3,6-tetrahydropyridin-4-yl)]benzonitrile

To a suspension of trifluoromethanesulfonic acid[1-tert-butoxycarbonyl-(1,2,3,6-tetrahydropyridin-4-yl)] ester (10.5 g, 0.032 mol) and tetrakis(triphenylphosphine) palladium(0) (1.8 g, 1.6 mmol) in tetrahydrofuran (95 ml) was added iodo(2-cyanophenyl)zinc (0.5M in tetrahydrofuran, 94 ml, 0.047 mol) dropwise. The reaction mixture was stirred at room temperature for 0.5 hours and quenched with saturated bicarbonate solution. The mixture was diluted with ethyl acetate and washed with water×2 and brine. Drying and solvent evaporation gave an oil (13 g); flash chromatography (silica gel, hexane-ethyl acetate, 92:8) gave 2-[1-tert-butoxycarbonyl-(1,2,3,6tetrahydropyridin-4-yl)] benzonitrile; $^1$H NMR (CDCl$_3$) d 1.50 (F, 9H), 2.53 (m, 2H), 3.67 (t, 2H, J=6.0 Hz), 4.12 (d, 2H, J=3.2 Hz), 5.98 (m, 1H), 7.34 (m, 2H), 7.54 (bt, 1H, J=7.6 Hz), 7.66 (bd, 1H, J=8 Hz).

Step C. 2-(1-tert-Butoxycarbonylpiperidin-4-yl)benzonitrile

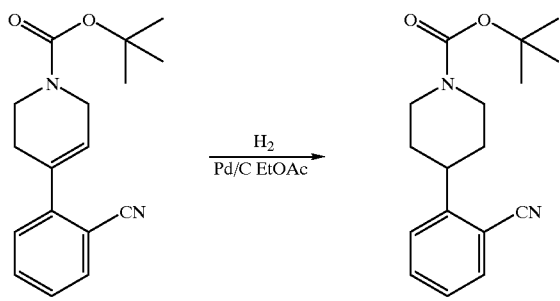

To a solution of 2-[1-tert-butoxycarbonyl-(1,2,3,6-tetrahydropyrdin-4-yl)]benzonitrile (5.3 g, 0.019 mol) and acetic acid (0.28 ml, 4.9 mmol) in ethanol (200 ml), degassed with argon was added palladium on carbon. The reaction was hydrogenated on a Parr capparatus at 50 psi for 15 hours. The mixture was recharged twice with acetic acid (0.14 ml, 0.28 ml) and palladium on carbon (900 mg, 1.8 g), hydrogenated as above and filtered through celite. Solvent evaporation gave 2-(1-tert-butoxycarbonylpiperidin-4-yl) benzonitrile; $^1$H NMR (CDCl$_3$) d 1.49 (s, 9H), 1.64 (m, 2H), 1.86 (bd, 2H, J=13.4 Hz), 2.88 (bt, 2H, J=14 Hz), 3.14 (tt, 1H, J=12 Hz, J=4 Hz), 4.27 (bs, 2H), 7.31 (m, 2H), 7.56 (bt, 1H, J=7.7 Hz), 7.63 (bd, 1H, J=7.7 Hz).

Step D. 2-(Piperidin-4-yl)benzonitrile hydrochloride

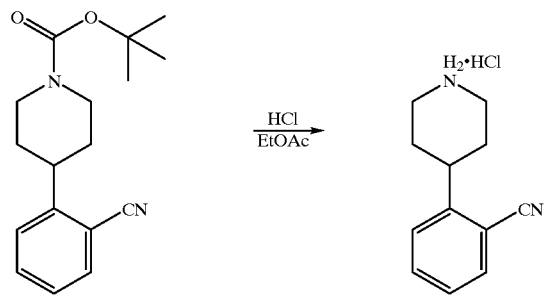

To a solution of 2-(1-tertbutoxycarbonylpiperidin-4-yl) benzonitrile (1.7 g, 5.9 mmol) in ethyl acetate (~50 ml), cooled to 0° C. was added hydrogen chloride gas, bubbled vigorously for 5 minutes. The reaction mixture was stirred for 10 minutes at 0° C., purged with argon and concentrated. Flushing with ethyl acetate×3 and concentration gave 2-(piperidin-4-yl)benzonitrile hydrochloride; $^1$H NMR (DMSO) d 1.98 (m, 4H), 3.07 (m, 2H), 3.21 (tt, 1H, J=12 Hz, J=3.8 Hz), 3.36 (m, 2H), 7.46 (m, 2H), 7.74 (bt, 1H, J=7.7 Hz), 7.83 (bd, 1H, J=7.0 Hz), 9.10 (bd, 2H).

Step E. 3-Bromo-1-tertbutoxycarbonylpropylamine

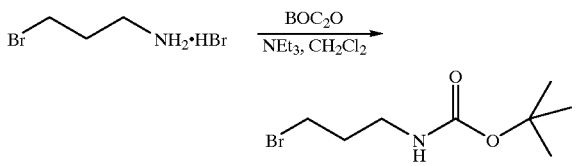

To a suspension of 3-bromopropylamine hydrobromide (5.0 g, 0.023 mol) and di-tert-butyl dicarbonate(5.0 g, 0.023 mol) in methylene chloride (125 ml), cooled to 0° C. was added triethylamine (3.2 ml, 0.023 mol). The reaction mixture was stirred for 3 hours at room temperature, diluted with methylene chloride and washed with water×2 and brine. Drying and solvent evaporation gave 3-bromo-1-tert-butoxycarbonylpropylamine; $^1$H NMR (CDCl$_3$) d 1.46 (s, 9H), 2.05 (m, 2H), 3.28 (m, 2H), 3.43 (m, 2H), 4.64 (bs, 1H).

Step F. 2-[1-(3-tert-Butoxycarbonylaminopropyl) pipexidin-4-yl]benzonitrile

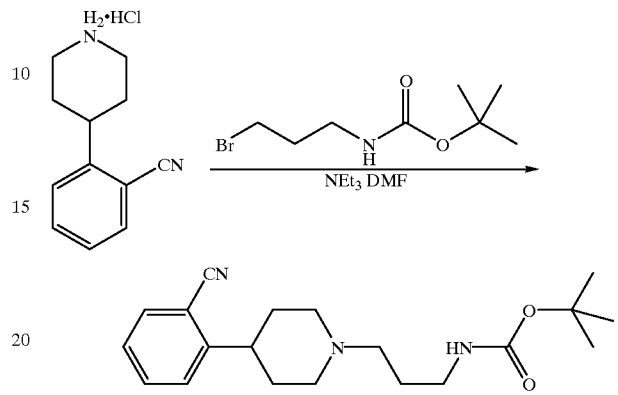

A suspension of 2-(piperidin-4-yl)benzonitrile hydrochloride (600 mg, 2.7 mmol), 3-bromo-1-tert-butoxycarbonylpropylamine (0.67 g, 2.8 mmol) and triethylamine (0.77 ml, 5.5 mmol) in DMF (12 ml) was stirred at room temperature for 15 hours. The reaction mixture was diluted with ethyl acetate and washed with saturated bicarbonate solution, water×2 and brine. Drying and solvent evaporation gave an oil (0.86 g); flash chromatography (silica gel, ethyl acetate) gave 2-[1-(3-tert-butoxycarbonylaminopropyl) piperidin-4-yl] benzonitrile; $^1$H NMR (CDCl$_3$) d 1.45 (s, 9H), 1.69 (m, 2H), 1.80 (bt, 2H, J=12 Hz), 1.89 (m, 2H), 2.12 (bt, 2H, J=10.8 Hz), 2.47 (t, 2H, J=6.7 Hz), 2.97–3.08 (m, 3H), 3.22 (m, 2H), 5.61 (bs, 1H), 7.29 (m, 1H), 7.39 (bd, 1H, J=7.9 Hz), 7.54 (bt, 1H, J=7.7 Hz), 7.62 (bd, 1H, J=7.7 Hz).

Step G. 2-[1-(3-Aminopropyl)-piperidin-4-yl] benzonitrile hydrochloride

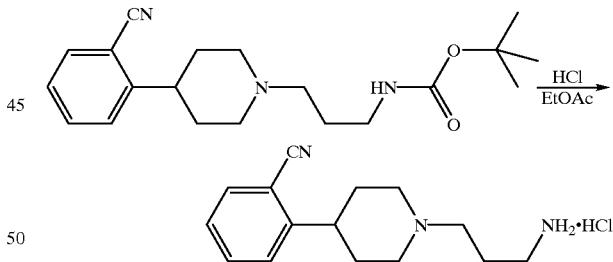

To a solution of 2-[1-(3-tert-butoxycarbonylaminopropyl)piperidin-4-yl] benzonitrile (0.73 g, 2.1 mmol) in ethyl acetate (100 ml), cooled to 0° C. was added hydrogen chloride gas, bubbled vigorously for 5 minutes. The reaction mixture was stirred for 10 minutes at 0° C., purged with argon and concentrated. Flushing with ethyl acetate×2 and concentration gave 2-[1-(3-arninopropyl)-piperidin4-yl] benzonitrile hydrochloride; $^1$H NMR (DMSO) d 2.00 (m, 2H), 2.10 (m, 2H), 2.28 (m, 2H), 2.95 (m, 2H), 3.18 (m, 4H), 3.56 (bd, 2H, J=11.7 Hz), 7.47 (m, 2H), 7.75 (bt, 1H, J=8 Hz), 7.84 (bd, 1H, J=7.9 Hz), 8.14 (bs, 2H), 11.1 (bd, 1H).

EXAMPLE 2

2-[1-(3-Aminopropyl)-piperidin-4-yl]-4-fluorobenzonitrile hydrochloride

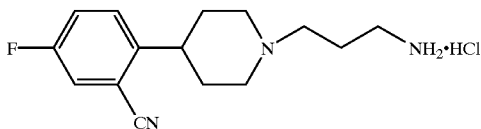

Step A. 4-(2-Cyano-4-fluorophenyl)-3,6-dihydro-2H-pyridine-1-carboxylic acid tert-butyl Ester A solution of 2-bromo-5-fluorobenzonitrle (8.1 g, 40.5 mmole) in THF (50 mL) was added rapidly to a solution of n-BuLi (20 mL, 2.5M, 50 mmole) in THF at −78° C. and the resulting dark solution stirred at for 5 minutes. To this solution was added $ZnCl_2$, (0.5 M in THF, 89 mL, nmmoles) and the solution was warmed to 0° C. Palladium tetrakistriphenylphosphine (1.5 g, 1.3 mmole) was added followed by trifluoromethanesulfonic acid [1-tert-butoxycarbonyl-(1,2,3,6-tetrahydropyridin-4yl)] ester from Example 1, step 1 from above (9 g, 27.16 mmole). The reaction was heated to 40° C. for 30 minutes and then cooled to room temperature and poured into saturated aqueous sodium bicarbonate (1 L). The mixture was extracted with ethyl acetate (3×300 mL) and the combined organic extracts were dried over anhydrous magnesium sulfate, filtered and concentrated at reduced pressure. The residue was chromatographed on silica gel eluting with 15% to 30% ethyl acetate/hexanes to give the product.

$^1$H NMR ($CDCl_3$): δ 7.4–7.25 (m, 3H), 5.95 (br s, 1H), 4.09 (br s, 2H), 3.65–3.60 (m, 2H), 2.50 (m, 2H), 1.50 (s, 9H).

Step B. 4-(2-Cyano-4-fluorophenyl)piperidine-1-carboxylic Acid Tert-butyl Ester 4-(2-Cyano-4-fluorophenyl)-3,6-dihydro-2H-pyridine-1-carboxylic acid tert-butyl ester (7.89 g, 26.1 mmol) and 10% Palladium on carbon (3.95 g) were combined in absolute ethanol (270 ml) containing acetic acid (0.79 ml) and the mixture hydrogenated at 60psi for 2.5 hrs. The catalyst was removed by filtration through super cel and the filtrate concentrated to dryness in vacuo to give a crude oil (8.26 g). Flash chromatography on silica gel (10% to 15% ethyl acetate in hexane) gave the product as a colorless oil.

$^1$H NMR ($CDCl_3$): δ 7.35–7.25 (m, 3H), 4.30–4.11 (br d, 2H), 3.15–3.06 (m, 1H), 2.91–2.82 (t, 2H), 1.87–1.82 (br d, 2H), 1.68–1.62 (m, 2H), 1.49 (s, 9H).

An ethyl acetate solution (56 ml) of 4-(2-Cyano-4-fluorophenyl)-piperidine-1-carboxylic acid tert-butyl ester (5.64 g, 18.5 mmol) was cooled to 0° C. and hydrogen chloride gas was bubbled through the solution until saturated (10 min). The solution was stirred in the cold (20 min) and then concentrated in vacuo to give the product as a white solid.

$^1$H NMR ($CD_3OD$): δ 7.61–7.53 (m, 2H), 7.53–7.43 (m, 1H), 3.60–3.50 (m, 2H), 3.40–3.16 (m, 3H), 2.18–1.94 (m, 4H).

Step D. 2-[1-(3-Aminopropyl)-piperidin-4-yl]-4-fluoro Benzonitrile Hydrochloride A suspension of 2-(piperidin-4-yl)-4-fluorobenzonitrile hydrochloride (2.5 g, 10.4 nmmol), 3-bromo-1-tert-butoxycarbonylpropylamine (3.22 g, 13.5 mmol) and triethylamine (3.76 ml, 27 mmol) in DMF (12 ml) was stirred at room temperature for 16 hours. The reaction mixture was diluted with ethyl acetate (200 mL) and washed with saturated bicarbonate solution, water×2 and brine. Dying and solvent evaporation gave after flash chromatography (silica gel, ethyl acetate) gave 3.1 g of 2-[1-(3-tert-butoxycarbonylaminopropyl) piperidin-4-yl]-4-fluorobenzonitrile. This material was dissolved in EtOAc (200 mL), cooled to 0° C. and HCl gas was bubbled into the solution for 15 minutes. The reaction mixture was concentrated at reduced pressure to give the product $^1$H NMR ($CD_3OD$): δ 7.65–7.50 (m, 2H), 7.5–7.43 (m, 1H), 3.75–3.65 (m, 2H), 3.40–3.1 (m, 3H), 2.25–2.1 (m, 4H).

EXAMPLE 3

1-(3-Aminopropyl)-4-(4-fluorophenyl)-piperidine-4-carbonitrile Dihydrochloride

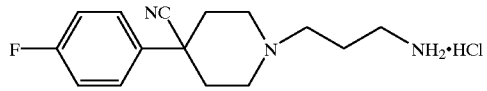

Step A. Bis-(2-chloro-ethyl)-tert-butoxycarbonylamine

To a solution of Bis(2-chloroethyl)amine hydrochloride (10 g, 56.66 mmol) in 210 ml 2.5:1 dioxane :$H_2O$ was added triethylamine (7.88 mL, 56.66 mmol). This solution was cooled to 0° C. under argon, and boc anhydride (14.96, 68.58 mmol) was added dropwise. This was stirred for 45 min, poured onto saturated sodium bicarbonate, and extracted with ethyl acetate. The combined organic layers were washed with saturated sodium chloride, dried with magnesium sulfate, and concentrated in vacuo t o give the product.

$^1$H NMR $d_H$ ($CDCl_3$) 3.70–3.55 (m, 8H), 1.47 (s, 9H).

Step B. 4-(4-Fluorophenyl)-tert-butoxycarbonylpiperidine-4-carbonitrile

To a solution of Bis-(2-chloro-ethyl)-tert-butoxycarbonylagnine (3.0 g, 12.39 mmol) in 75 mL of Dd n was added 4-fluorobenzylacetonitrile (1.515 g, 11.27 mmol). This solution was cooled to 0° C., and a 60% dispersion of sodium hydride was added portion wise (1.17 g, 29.25 mmol). The solution was sintered for 20 min , warmed to room temperature, then heated to 80° C. for 24 h. It was poured onto water, and extracted with ethyl acetate. The combined organic layers were washed with saturated sodium chloride, dried with magnesium sulfate, and concentrated in vacuo. The crude material was passed through silica (25% ethyl acetate, hexane) to give the product.

$^1$H NMR $d_H$ ($CDCl_3$) 7.50–7.40 (m, 2H), 7.15–7.05 (m, 2H), 4.40–4.20 (br m, 2H), 3.30–3.10 (br m, 2H), 2.15–2.05 (m, 2H), 2.00–1.85 (m, 2H), 1.49 (s, 9H).

Step C. 4-(4-Fluorophenyl)-piperidine-4-carbonitrile Hydrochloride

A solution of 4-(4-fluorophenyl)-tert-butoxycarbonylpiperidine-4-carbonitrile (840 mg, 2.74 mmol) in 50 mL ethyl acetate was cooled to 0° C. Hydrogen chloride gas was bubbled through the solution for 2 min. It was stirred for 10 min and then concentrated in vacuo to give the product.

$^1$H NMR $d_H$ ($CD_3OD$) 7.65–7.55 (M, 2H), 7.30–7.20 (m, 2H), 3.68–3.60 (m, 2H), 3.45–3.00 (m, 2H), 2.50–2.25 (m, 4H).

Step D. 1-(3-tert-Butoxycarbonylamino-propyl)-4-(4-fluorophenyl)-piperidine -4-carbonitrile The free base of 4-(4-fluorophenyl)-piperidine-4-carbonitrile hydrochloride was prepared by pouring the salt onto saturated sodium carbonate ,extracting with ethyl acetate, drying the organic layers with sodium sulfate, filtering, and concentrating in vacuo. To a solution of 4-(4-fluorophenyl)-piperidine-4-carbonitrile (300 mg, 1.578 mmol) in 4 mL of DMF was added 3-bromopropyl-tert-butoxycarbonylamine (387 mg, 1.626 mmol) and triethylamine (225 mL, 1.623 mmol) under argon. The solution was stirred for 2h at 60° C., poured onto saturated sodium bicarbonate, and extracted with ethyl acetate. The combined organic layers were washed with saturated sodium chloride, dried with magnesium sulfate, and concentrated in vacuo. The crude material was passed through silica (5% methanol, dichloromethane) to give the product.

$^1$H NMR $d_H$ (CDCl$_3$) 7.50–7.45 (m, 2H), 7.15–7.05 (m, 2H), 5.40 (br S, 1H), 3.23–3.21 (m, 2H), 3.06–3.02 (m, 2H), 2.55–2.46 (m, 4H), 2.10–2.06 (m, 4H), 1.70–1.64 (m, 2H).

Step E. 1-(3-Aminopropyl)-4-(4-fluorophenyl)-piperidine-4-carbonitrile

A solution of 1-(3-tert-butoxycarbonylamino-propyl)-4-(4-fluorophenyl)piperidine-4-carbonitrile (480 mg, 1.33 mmol) in 50 mL ethyl acetate was cooled to 0° C. Hydrogen chloride gas was bubbled through the solution for 2 min, and it was stirred for 20 min and then concentrated in vacuo to give the product.

$^1$H NMR $d_H$ (CD$_3$OD) 7.66–7.61 (m, 2H), 7.26–7.20 (m, 2H), 3.85–8.81 (m, 2H), 3.45–3.25 (m, 4H), 3.10 (t, 2H, J=7.6Hz), 2.60–2.52 (m, 4H), 2.28–2.15 (m, 2H).

EXAMPLE 4

1-(3-Aminopropyl)-4-(2,4-difluorophenyl)-piperidine-4-carbonitrile Dihydrochloride

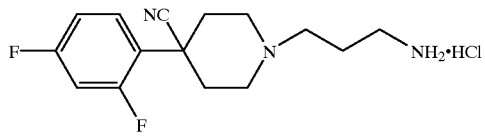

This compound was prepared by procedures similar those described above for Example 3 except substituting 2,4-difluorophenyl acetonitrile in Step B.

$^1$H NMR $d_H$ (CD$_3$OD) 7.66–7.55 (m, 2H), 7.21–7.05 (m, 2H), 3.90–3.85 (m, 2H), 3.55–3.25 (m, 4H), 3.15–3.05 (m, 2H), 2.70–2.55 (m, 4H), 2.30–2.015 (m, 2H).

EXAMPLE 5

1-(3-Aminopropyl)-4-cyano-4-(2-cyano-4-fluorophenyl)-piperidine

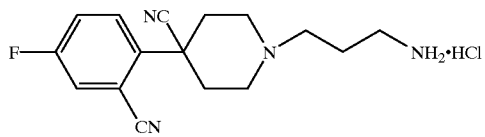

Step A. 2-Cyano-4-fluorophenylacetonitrile

A solution of 1.0 g (7.2 mmol) 2,5-difluorobenzonitrile, 1.2 ml (8.4 mmol) tert-butyl cyanoacetate, and 3.5 g (10.7 mmol) cesium carbonate in 30 ml DMSO was heated to 100° C. for 2 hours. The reaction was cooled to room temperature, diluted with 600 ml ether, washed with 300 ml 10% KHSO$_4$, 300 ml dilute brine, and 300 ml brine. The ether layer was dried over MgSO$_4$, filtered, and concentrated to give 1.6 g of an oil (TLC Rf=0.34 (20% EtOAc:hexanes)). This oil was dissolved in 100 ml 1,2-dichloroethane and 0.5 ml trifluoroacetic acid was slowly added. The reaction was heated to reflux for 4 hours, cooled, diluted with 200 ml ether, washed with 100 ml saturated aqueous sodium bicarbonate solution, 100 ml brine, then dried over MgSO4, filtered, and concentrated in vacuo. Purification by flash chromatography (4×12 cm silica gel, linear gradient 20–50% EtOAc:hexanes) afforded the title compound. $^1$H NMR (300 MHz, CDCl$_3$) d 7.64 (m, 1H); 7.41 (m, 2H); 3.95 (s, 2H).

Step B. 4-Cyano-4-(2-cyano-4-fluorophenyl)-piperidine-1-carboxylic Acid Tert Butyl Ester.

To a solution of 0.098 g (0.61 mmol) 2-cyano-4-fluorophenylacetonitrile and 0.17 g (0.07 mmol) N-Boc-di-(2-chloroethyl)amine in 3 ml DMSO was added 0.69 g (2.1 mmol) cesium carbonate. The reaction was stirred 24h at room temperature, then diluted with 100 ml ethyl acetate, washed with 100 ml aqueous 10% KHSO$_4$ solution, 100 ml saturated sodium bicarbonate solution, 100 ml brine; then dried over Na$_2$SO$_4$, filtered and concentrated in vacuo. Purification by flash chromatography (3×12 cm silica gel, linear gradient 0–4% acetone/CH$_2$Cl$_2$) afforded the title compound. TLC Rf=0.25 (30% EtOAc:hexanes). $^1$H NMR (400 MHz, CDCl$_3$) d 7.65 (m, 1H); 7.50 (m, 1H); 7.37 (m, 1H); 4.37 (br m, 2H); 3.25 (br m, 2H); 2.30 (m, 4H); 1.50 (s, 9H).

Step C. 1-(3-N-Bocaminopropyl)-4-cyano-4-(2-cyano-4-fluorophenyl)-piperidine.

To a 0° C. solution of 0.53 g (1.63 mmol) 4-cyano-4-(2-cyano-4-fluorophenyl)piperidine-1-carboxylic acid tert butyl ester in 10 ml ethyl acetate was bubbled through HCl gas for 5 minutes. The heterogeneous reaction mixture was stirred 5 more minutes at 0° C., then diluted with 70 ml EtOAc and extracted 2×75 ml H$_2$O. The combined aqueous extracts were brought to pH 11 with 3 ml 50% aqueous NaOH and extracted 3×50 ml ethyl acetate, adding solid NaCl to each extraction. The combined organic extracts were dried over Na$_2$SO$_4$, filtered and concentrated to give 0.33 g of an oil that was dissolved in 10 ml DMF. To this was added 0.3 ml (2.1 mmol) triethylamine and 0.38 g (1.6 mmol) N-boc-3-bromopropylamine. The reaction mixture was stirred 24 hours at room temperature, then diluted with 200 ml ethyl acetate, washed with 100 ml saturated aqueous sodium bicarbonate solution, 100 ml water, and 100 ml brine; then dried over Na$_2$SO$_4$, filtered and concentrated in vacuo. Purification by flash chromatography (3×12 cm silica gel, linear gradient 2–5% MeOH/1% NH$_4$O/CH$_2$Cl$_2$) afforded the title compound.

$^1$H NMR (400 MHz, CDCl$_3$) d 7.60 (dd, 1H, J=9.16 and 5.13 Hz); 7.51 (dd, 1H, J=7.69 and 2.93 Hz); 7.35 (m, 1H); 5.10 (br s, 1H); 3.20 (m, 2H); 3.08 (d, 2H, J=12.5 Hz); 2.54 (m, 4H); 2.40 (d, 2H, J=12.5 Hz); 2.25 (dt, 2H, J=2.54 and 11.9 Hz); 1.70 (quint, 2H, J=6.45 Hz); 1.43 (s, 9H).

Step D. 1-(3-Aminopropyl)-4-cyano-4-(2-cyano-4-fluorophenyl)-piperidine.

To a 0° C. solution of 0.38 g (1 mmol) mmol) 1-(3-N-Bocaminopropyl)-4-cyano-4-(2-cyano-4-fluorophenyl)-piperidine in 5 ml ethyl acetate was bubbled through HCl gas for 5 minutes. The heterogeneous reaction mixture was stirred 5 more minutes at 0° C., then concentrated in vacuo to give the title compound as the dihydrochloride salt. $^1$H NMR (300 MHz, CD$_3$OD) d 7.82 (dd, 1H, J=8.06 and 2.93 Hz); 7.75 (dd, 1H, J=8.79 and 4.88 Hz); 7.60 (m, 1H); 3.95 (d, 2H, J=13.0 Hz); 3.41 (m, 4H); 3.10 (t, 2H, J=7.57 Hz); 2.90 (m, 2H); 2.63 (br t, 2H, J=14.7 Hz); 2.23 (m, 2H).

EXAMPLE 6

1-(3-Amino-propyl)-4-cyanophenyl)-piperidine-4-carbonitrile

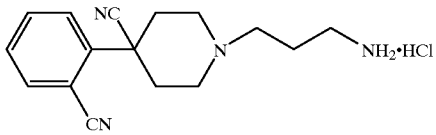

Step A. 1-(3-tert-Butoxycarbonylaminopropyl)-4-(4-cyanophenyl)-piperidine-4-carbonitrile This compound was prepared by a procedure similar to Example 5.

$^1$H NMR d$_H$ (CDCl$_3$) 7.82–7.79 (d, 1H, J=7.6Hz), 7.66–7.62 (m, 2H), 7.50–7.48 (t, 1H, J=6.1 Hz), 5.20–5.15 (br s, 1H), 3.22–3.20 (br m, 2H), 3.11–3.06 (br m, 2H), 2.59–2.51 (m, 4H), 2.44–2.40 (br m, 2H), 2.33–2.28 (m, 2H), 1.73–1.68 (m, 2H), 1.43 (s, 9H).

Step B. 1-(3-Amino-propyl)-4-(4-cyanophenyl)-pipenidine-4-carbonitrile

This compound was prepared by a procedure similar to Example 5, step D.

$^1$H NMR d$_H$ (CDCl$_3$) 7.97–7.95 (d, 1H, J=7.1 Hz), 7.83–7.80 (t, 1H, J=7.1), 7.72–7.63 (m, 2H), 3.95–3.90 (d, 2H, J=15Hz), 3.51–3.29 (m, 4H), 3.12–3.07 (t, 2H, J=7.8), 2.93–2.88 (br m, 2H), 2.67–2.55 (m, 2H), 2.22–2.01 (m, 2H).

EXAMPLE 7

3-[4-(4-Fluorophenyl)piperidin-1-yl]propylamine

Step A. 4-(4-Fluorophenyl)piperidine Hydrochloride

To a solution of 4-(4-fluorophenyl)-1,2,3,6-tetrahydropyridine hydrochloride (10 g) in methanol (200 mL) was added 10% palladium on charcoal (0.5 g) and the mixture was hydrogenated at 50 psi for 3 h. The catalyst was removed by filtration and solvent was evaporated to leave the product as a white powder, which was used in the next step without any purification. The 1H-NMR and TLC analysis showed this product to be pure. M.P. 181–182° C. $^1$H NMR (CDCl$_3$): d 1.95–2.03 (br d, 2H), 2.14–2.29 (m, 2H), 2.70–2.80 (m, 1H), 2.91–3.07 (br q, 2H), 3.60–3.64 (br d, 2H), 6.96–7.03 (m, 2H), 7.19–7.22 (m, 2H), 9.60 (br s, 1H), 9.71 (br s, 1H).

Step B. 3-[4-(4-Fluorophenyl)piperidin-1-yl]propylphthalimide

A mixture of 4-(4-fluorophenyl)piperidine hydrochloride (5.08 g, 23.2 mmol), 3-bromopropylphthalimide (6.22 g, 23.2 mmol), and potassium carbonate (15 g) in DMF (100 mL) was stirred and heated at 95–100° C. for 12 h. About 80% of the solvent was evaporated at reduced pressure, the residue was diluted with ethyl acetate (200 mL) and washed with brine (3×100 mL) and dried (Na$_2$SO$_4$). Solvent was evaporated and the residue was purified by column chromatography on silica gel using 1/1 hexane-ethyl acetate to 100% ethyl acetate as eluent. This product was crystallized from isopropanol to give a white crystalline solid; m.p. 80–81° C. This material was used in the next step. Concentration of the mother liquor and cooling gave the second crop.

$^1$H NMR (CDCl$_3$): d 1.43–1.52 (m, 2H), 1.67–1.75 (m, 2H), 1.80–1.96 (m, 4H), 2.33–2.46 (m, 3H), 2.94–2.99 (br d, 2H), 3.78 (t, J=7 Hz, 2H), 6.90–7.04 (m, 4H), 7.70–7.74 (m, 2H), 7.84–7.87 (m, 2H).

Step C. 3-[4-(4-Fluorophenyl)piperidin-1-yl]propylamine

To a solution of 3-[4-(4-fluorophenyl)piperidin-1-yl] propylphthalilide (4.5 g, 12.3 mmol) in methanol (200 mL), hydrazine (4 mL) was added and the mixture was stirred and refluxed for 8 h. It was cooled, and the white solid was filtered and washed with methanol (20 mL). Solvent was evaporated, and the residue was dried under vacuum for 4 h. Chloroform (50 mL) was added to this material, it was stirred for 1 h and filtered. The white solid was washed with more chloroform (20 mL), and the solvent was evaporated from the combined filtrates to leave the crude product as an oil. It was purified by column chromatography on silica gel using dichloromethane/methanol/2M ammonia in methanol (10/3/1) as the eluent. $^1$H NMR (CDCl$_3$): d 1.60–1.83 (m, 6H), 1.96–2.07 (m, 4H), 2.40–2.55 (m, 3H), 2.70–2.85 (br t, 2H), 3.03–3.07 (br d, 2H), 6.93–7.00 (m, 2H), 7.14–7.20 (m, 2H).

EXAMPLE 8

3-Aminopropyl-4-(2-pyridyl)piperidine

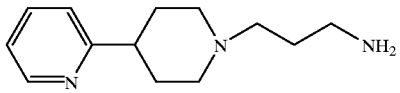

Step A. 1-(3-Aminopropyl)-4-[2-pyridyl]pyridinium Bromide Hydrobromide

A solution of 2,4'-dipyridyl (25 g, 160 mmol) and 3-bromopropylamine hydrobromide (35 g, 160 mmol) in DMF (60 mL) was heated at 90–95° C. for 10 h. After cooling to room temperature, anhydrous ether (500 mL) was added to the mixture. The resulting white solid was filtered, washed with ether and dried. $^1$H NMR (300 MHz, DMSO) d 2.35–2.44 (m, 2 H), 3.08–3.13 (m, 2 H), 4.76–4.81 (m, 2 H), 7.58 (dd, J=4.8 Hz, J=7.5 Hz, 1 H), 8.03 (dt, J=1.8 Hz, J=7.8 Hz, 1 H), 8.32 (d, J=7.8 Hz, 1 H), 8.77–8.81 (m, 3 H), 9.12 (d, J=6.3 Hz, 2 H). Anal. Calcd. for C$_{13}$H$_{16}$N$_3$Br.HBr.0.5 H$_2$O: C, 40.65; H, 4.72; N, 10.94. Found: C, 40.83; H, 4.37; N, 11.05.

Step B. 3-(3',6'-Dihydro-2'-H-[2,4']bipyridinyl-1'-yl)-propylamine

To a solution of 1-(3-aminopropyl)-4-[2-pyridyl] pyridinium bromide hydrobromide (6 g, 16 mmol) in MeOH (150 mL) at 0° C. was added NaBH$_4$ (2 g, 53 mmol) in small portions over a period of 2 h. The reaction mixture was stirred overnight at room temperature and the solvent was evaporated. The residue was suspended in ether (200 mL) and treated with 50% NaOH solution (100 mL). The ether layer was separated and the aqueous layer was extracted with ether (2×50 mL). The combined ether extracts were dried over potassium carbonate and the solvent was removed to give 3-(3',6'-dihydro-2'-H-[2,4']bipyridinyl-1'-yl)-propylamine as an oil. It was immediately used in the next step without purification.

Step C. 3-Aminopropyl-4-(2-pyridyl)piperidine

To a solution of 3-(3',6'-dihydro-2'-H-[2,4']bipyridinyl-1'-yl)-propylamine (3.48 g crude, 15.9 mmol) in MeOH (40 mL), was added 1.0 g of palladium hydroxide catalyst. The suspension was hydrogenated under 120 psi for 10 h after which the reaction mixture was filtered through a pad of Celite and the solvent was removed. The residue was purified by column chromatography over silica gel (30 g) [Note: If a large excess of silica gel is used the recovery of the product will be very low] using methylene chloxidemethanol/2M ammonia in MeOH (90:8:4 to 90:40:40) as eluent. The product was obtained as a pale yellow oil.

¹H NMR d (CD₃OD) 1.50–1.99 (m, 10 H), 2.02–2.06 (m, 2 H), 2.37–2.75 (m, 3 H), 3.02–3.06 (br m, 2 H), 7.05–7.09 (m, 4 H), 7.16 (dt, J=0.9 Hz, J=8.7 Hz, 1H), 8.48(dd, J=0.9 Hz, J=4.2 Hz, 1 H).

EXAMPLE 9

3-[4-(4-Fluorophenyl)-4-hydroxypiperidin-1-yl] propylamine Hydrochloride

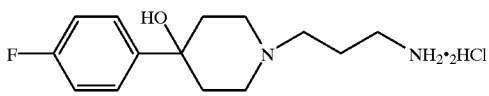

A solution of 4-(4-fluorophenyl)-4-piperidinol (2.3 g, 10 mmole) (Sigma) and 3-bromo-1-tert-butoxycarbonylpropylamine (2.5 g, 10.4 mmole) in DMF was treated with TEA (2.5 g, 25 mmole) and stirred at room temperature, for 24 hours. The reaction was poured into saturated sodium bicarbonate solution (150 mL) and the mixture extracted with ethyl acetate (3×150 mL) the combined extracts were dried over anhydrous magnesium sulfate, filtered and concentrated at reduced pressure to give an oil which was chromatographed on silica gel eluting with methanol/methylene chloride to give 2.2 g of the intermediate Boc protected. This material was dissolved in ethyl acetate (100 mL), cooled to 0° C., and hydrogen chloride gas was bubbled through the solution until saturated (10 min). The solution was stirred in the cold (20 min) and then concentrated in vacuo to give the product as a white solid.

¹H NMR (CD₃OD): δ 7.6–7.45 (m, 2H), 7.15–7.05 (m, 2H), 3.65–3.40 (m, 4H), 3.3–3.25 (m, 2H), 3.15–3.05 (t, J=8.2 Hz, 2H), 2.55–2.4 (m, 2H), 2.30–2.15 (m, 2H), 2.05–1.8 (m, 2H)

EXAMPLE 10

(−)-4-(3,4Difluorophenyl)-2-oxo-1,2,3,4-tetrahydro-pyrimidine-5-carboxylic Acid

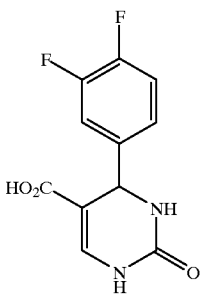

Step A. 4-(3,4-Difluorophenyl)-2-oxo-1,2,3,4-tetrahydro-pyrimidine-5-carboxylic Acid Methyl Ester To a solution of methyl 3,3-dimethoxypropionate (284 mL, 2.0 mmol) in 4.0 mL THF was added urea (180 mg, 3.0 mmol), 3,4-difluorobenzaldehyde (284 mg, 2.0 mmol), acetic acid (12.0 mL, 0.20 mmnol), copper oxide (27.0 mg, 0.20), and boron trifluoxide diethyl etherate (320 mL, 2.6 mmol). The solution was heated to 650° C. under argon for 24 h, poured onto saturated sodium bicarbonate, and extracted with ethyl acetate. The combined organic layers were washed with saturated sodium chloride, dried with magnesium sulfate, and concentrated in vacuo. The crude material was swished with dichloromethane to give the mixture of enantiomers. The enantiomers were resolved on a chiral 250×46 mm OD column with a mobile phase of 3:1 hexane: ethyl acetate, a flow rate of 1 ml/min, and 280 nm detection.

¹H NMR d_H (DMSO) 9.29 (d, 1H, J=5.37Hz), 7.75 (s, 1H), 7.50–7.35 (m, 1H), 7.30–7.20 (m, 2H), 7.15–7.05 (m, 1H), 5.155 (d, 1H, J=2.68Hz), 3.565 (s, 3H).

Step B. (−)-4-(3,4Difluorophenyl)-2-oxo-1,2,3,4-tetrahydro-pyrimidine-5-carboxylic acid To a solution of (−)-4-(3,4-Difluorophenyl)-2-oxo-1,2,3,4-tetrahydro-pyrimidine-5-carboxylic acid methyl ester (450 mg, 1.68 mmol) in 15 mL MeOH was added 1M NaOH (28 mL, 28.0 mmol). The solution was stirred under argon at room temperature for 6 h, poured 10% potassium hydrogen sulfate, and extracted with ethyl acetate. The combined organic layers were washed with saturated sodium chloride, dried with magnesium sulfate, and concentrated in vacuo to give the product. ¹H NMR d_H (DMSO) 9.17 (d, 1H, J=5.37Hz), 7.69 (s, 1H), 7.50–7.35 (m, 1H), 7.30–7.20 (m, 2H), 7.15–7.05 (m, 1H), 5.13 (d, 1H, J 2.44).

EXAMPLE 11

(+) and (−)-4-(3,4-difluorophenyl)-1-methyl-2-oxo-1,2,3,4-tetrahydro-pyrimidine-5-carboxylic Acid

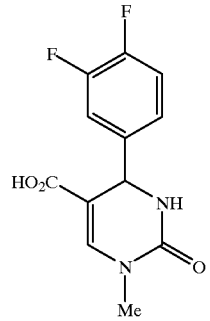

Step A. 4-(3,4Difluorophenyl)-1-methyl-2-oxo-1,2,3,4-tetrahydro-pyr-imidine-5-carboxylic Acid Methyl Ester The title compound was prepared using the Biginelli reaction described above in Example 10 except substituting methyl urea for urea in step A ¹H NMR (300 MHz, CDCl₃) d 7.32 (s, 1H); 7.2–7.1 (m, 3H); 6.02 (s, 1H), 5.34 (s, 1H); 3.66 (s, 3H); 3.20 (s, 3H).

Step B. 4-(3,4-Difluorophenyl)-1-methyl-2-oxo-3-(1-phenylethyl-carbamoyl)-1,2,3,4-tetrahydro-pyIimidine-5-carboxylic Acid Methyl Ester To a −78° C. solution of 4 g (14 mmol) 4-(3,4-Difluorophenyl)-1-methyl-2-oxo-1,2,3,4-tetrahydro-pyrimidine-5-carboxylic acid methyl ester in 70 ml THF was added 7 ml (14 mmol, 2M solution in THF/heptane/ethylbenzene) LDA. The reaction mixture was stirred for 15 minutes, then a −78° C. solution of 3.13 g (15.5 mmol) p-nitrophenylchloroformate in 10 ml THF was added very quickly via a large bore cannula. After stirring 45 min at −78° C., the reaction mixture was poured into 300 ml EtOAc and washed with 200 ml saturated aqueous sodium bicarbonate solution, 200 ml 5% aqueous K₂CO₃ solution, 200 ml water, and 200 ml brine; then dried over Na₂SO₄, filtered and concentrated in vacuo. The residue was dissolved in 50 ml DMF and to this was added 2 ml (14 mmol) triethylamine and 1.83 ml (14 mmol) (R)-1-phenethylamine. The reaction mixture was stirred 3 hours at room temperature, diluted with 400 ml ethyl acetate, washed with 3×150 ml 10% aqueous $K_2CO_3$ solution, 1×200 ml water, and 1×200 ml brine; then dried over $Na_2SO_4$, filtered and concentrated in vacuo. Purification by flash chromatography (6×18 cm silica gel, linear gradient 0–5% MeOH/1% $NH_4OH/CH_2Cl_2$) followed by purification of the mixed fractions by flash chromatography (5×15 cm silica gel, linear gradient 0–12% MeOH/1% $NH_4OH/CH_2Cl_2$) afforded "hi Rf diastereomer". $^1H$ NMR (300 MHz, $CDCl_3$) d 9.24 (d, 1H, J=6.84 Hz); 7.36–7.04 (m, 4H); 6.59 (s, 1H); 4.95 (quint, 1H, J=6.84 Hz); 3.67 (s, 3H); 3.27 (s, 3H); 1.48 (d, 3H, J=7.08 Hz). and 1.7 g "lo Rf diastereomer" $^1H$ NMR (300 MHz, $CDCl_3$) d 9.22 (d, 1H, J=7.08 Hz); 7.34–7.00 (m, 4H); 6.67 (s, 1H), 5.00 (quint, 1H, J=6.92 Hz); 3.73 (s, 3H); 3.27 (s, 3H); 1.50(d, 3H, J=6.84 Hz).

Step C. (+) and (−) 4-(3,4-Difluorophenyl)-1-methyl-2-oxo-1,2,3,4-tetrahydropyrimidine-5-carboxylic Acid Methyl Ester A solution of 1.7 g (4.3 mmol) 4-(3,4Difluorophenyl)-1-methyl-2-oxo-3-(1-phenylethylcarbamoyl) 1,2 ,3,4-tetrahydro-pyrimidine-5-carboxylic acid methyl ester, "hi Rf diastereomer" , and 3 ml (20 mmol) DBU in 50 ml toluene was heated to 110° C. for 16 hours the cooled to room temperature. To this was added 2 ml concentrated aqueous $NH_4OH$ solution and the reaction stirred 5 minutes, then 200 ml ethyl acetate and 200 ml 10% aqueous $KHSO_4$ solution were added and the layers mixed and separated. The ethyl acetate layer was washed with 200 ml water and 200 ml brine, dried over $Na_2SO_4$, filtered and concentrated in vacuo. Purification by flash chromatography (5×15 cm silica gel, linear gradient 50–90% EtOAc/hexanes) afforded of the resolved DHP $\alpha_D^{25}$=+121° c=0.48 $CH_2Cl_2$. The same procedure on the "lo Rf diastereomer" afforded DHP with $\alpha_D^{25}$=−126° c=0.6 $CH_2Cl_2$. HPLC analysis on a Chiracel OD 250×4.6 mm column, 70% hexane(0.1% diethylamine)/30% ethanol 1 ml/min gave retention times of 5.6 min for the (+) enantiomer (93% ee) and 6.2 min for the (−) enantiomer (91% ee).

Step D. (+) and (−) 4-(3,4-Difluorophenyl)-1-methyl-2-oxo-1,2,3,4-tetrahydro-pyr-imidine-5-carboxylic Acid The title compounds prepared by hydrolysis of the product of Step C by the procedure described in Example 10, step B.

$^1H$ NMR (300 MHz, $CD_3OD$) d 7.50 (s, 1H); 7.27–7.10 (m, 3H); 5.25 (s, 1H); 3.20 (s, 3H).

EXAMPLE 12
(−)-4-(3,4-Difluorophenyl)-1,3-dimethyl-2-oxo-1,2,3,4-tetrahydro-pyrimidine-5-carboxylic Acid

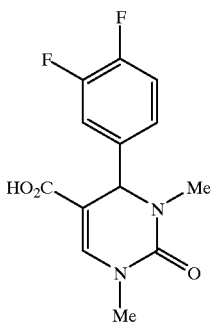

To a solution of 0.36 g (1.3 mmol) (−)-4-(3,4-Difluorophenyl)-1-methyl-2-oxo-1,2,3,4-tetrahydro-pyrimidine-5-carboxylic acid methyl ester (the product of Example 10, Step C) in 3 ml DMF was added 0.068 g (2.8 mmol) sodium hydride. After the gas evolution had ceased (5 min), 0.10 ml (1.6 mmol) methyl iodide was added and the reaction mixture was stirred 2 hours at room temperature then poured into 100 ml EtOAc and washed 100 ml 5% aqueous $KHSO_4$ solution, 100 ml water, and 100 ml brine; then dried over $Na_2SO_4$, filtered and concentrated in vacuo. The residue was dissolved in 5 ml MeOH and to this was added 0.2 ml (0.5 mmol, 2.5M solution in water) NaOH, 2 ml THF, and 0.8 ml (2 mmol, 2.5M solution in water) NaOH. The initially heterogeneous reaction mixture slowly became homogeneous, and after 6 hours, the reaction was poured into 75 ml EtOAc and extracted 2×75 ml $H_2O$. The aqueous layer was acidified to pH=1 with concentrated HCl solution, solid NaCl was added and the mixture extracted 3×50 ml ethyl acetate. The combined ethyl acetate extracts were dried over $Na_2SO_4$, filtered and concentrated in vacuo. Toluene (50 ml) was added and removed in vacuo two times, and the residue was dissolved in 1 ml $CH_2Cl_2$ and 0.33 g of essentially pure solid was obtained by adding hexane. $\alpha^{25}$=−150° C.=0.37 MeOH. $^1H$ NMR (300 MHz, $CD_3OD$) d 7.45 (s, 1H); 7.28–7.12 (m, 3H); 5.25 (s, 1H); 3.21 (s, 3H); 2.82 (s, 3H).

EXAMPLE 13
4-(3,4-Difluorophenyl)-1,6-dimethyl-2-oxo-1,2,3,4-tetrahydro-pyrimidine-5-carboxylic Acid

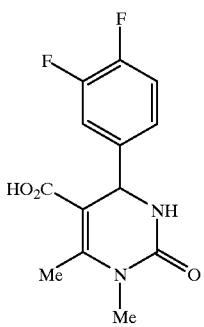

Step A. 4-(3,4-Difluorophenyl)-1,6-dimethyl-2-oxo-1,2,3,4-tetra-hydro-pyrimidine-5-benzyl Carboxylate Benzyl acetoacetate (28.8 g, 150 mmol), methyl urea (11.26 g, 152 mmol) and 3,4-difluorobenzaldehyde (21.3 g, 150 mmol) are combined in ethanol (60 ml) and conc. HCl (24 drops) is added. The reaction mixture is refluxed for 5 hrs. The solvent is removed in vacuo and ethanol (30 ml) and hexane (250 ml) is added. 4-(R,S)-(3,4-Difluorophenyl)-1,6-dimethyl-2-oxo-1,2,3,4-tetrahydro-pyrimidine-5-benzyl carboxylate is obtained as a pale yellow solid by filtration. Another portion of product is obtained from the mother liquor.

$^1$H NMR (CDCl$_3$): δ 7.40–7.25 (m, 3H), 7.25–7.15 (m, 2H), 7.10–6.80 (m, 3H), 6.06 (br s, 1H), 5.35 (d, 1H), 5.10 (AB q, 2H), 3.25 (s, 3H), 2.55 (s, 3H).

Step B. 4-(3,4-Difluorophenyl)-1,6-dimethyl-2-oxo-1,2,3,4-tetra-hydro-pyrimidine-5-carboxylic Acid A solution of 4-(3,4-Difluorophenyl)-1,6-dimethyl-2-oxo-1,2,3,4-tetrahydro-pyrimidine-5-benzyl carboxylate (3 g, 8.06 mmol) in ethanol (100 ml) and ethyl acetate (60 ml) is hydrogenated over 10% Pd/C (300 mg) for 2 hrs. After filtration on celite and concentration in vacuo, 4-(R,S)-(3,4-Difluorophenyl)-1,6-dimethyl-2-oxo-1,2,3,4-tetrahydro-pyrimidine-5-carboxylic acid is obtained as a white solid.

$^1$H NMR (d6 DMSO): δ 8.00 (d, 1H), 7.40 (br q, 1H), 7.25–7.20 (m, 1H), 7.15–7.05 (m, 1H), 5.15 (d, 1H), 3.10 (s, 3H), 2.50 (s, 3H).

EXAMPLE 14

(−)-4-(3,4-Difluorophenyl)-3,6-dimethyl-2-oxo-1,2,3,4-tetrahydro-pyrimidine-5-carboxylic Acid

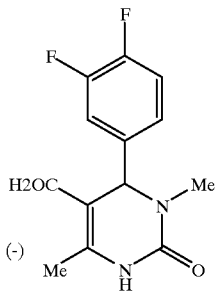

Step A. (+) and (−)-6-(3,4-Difluorophenyl)-2-methoxy-4-methyl-1,6-dihydro-pyrimidine-5-carboxylic Acid Methyl Ester.

To a solution of methyl acetoacetate (8.0 g, 0.069 mol), 3,4-difluorobenzaldehyde (9.8 g, 0.069 mol), acetic acid (0.490 g, 0.008 mole) and piperidine (0.69 g, 0.008 mol) in benzene (1.5 L) were added molecular sieves (37.9 g) and the mixture was stirred at room temperature for 48 h. The molecular sieves were removed by filtration and the solvent was evaporated under reduced pressure. The residue was purified by trituration from hexane to yield the intermediate methyl 2-[(3,4-difluorophenyl)methylene]-3-oxo-butyrate product as a yellow solid as a mixture of cis and trans isomers. A suspension of the methyl 2-[(3,4-difluorophenyl)methylene]-3- oxo-butyrate thus obtained(12 g, 49.9 mmol), O-methylisourea hemisulfate (11.15 g, 67.76 mmol, 1.5 eq.), and sodium bicarbonate (17 g, 203 mmol, 3 eq.) in DMF (110 mL) was stirred at 60° C. for 8 hours. The solvent was evaporated and the residue was partitioned between ethyl acetate and water. The organic layer was washed with brine and dried over anhydrous sodium sulfate. The residue was purified by chromatography on silica gel eluting with 25%–30% EtOAc/hexane, to give the product as a pale yellow solid. $^1$H NMR (CDCl$_3$) d 7.2–7.0 (m, 3H), 6.0 (s, 1H), 5.56 (s, 1H), 3.75 (s, 3H), 3.65 (s, 3H), 2.33 (s, 3H), The racemic material was resolved by preparative HPLC (Chiralpak AD, 70:30 0.1% diethyl amine in hexane: ethanol) to provide both enantiomers.

Step B. (+)-6-(3,4-Difluorophenyl)-2-methoxy-1,4-dimethyl-1,6-dihydro-pyrimidine-5-carboxylic Acid Methyl Ester

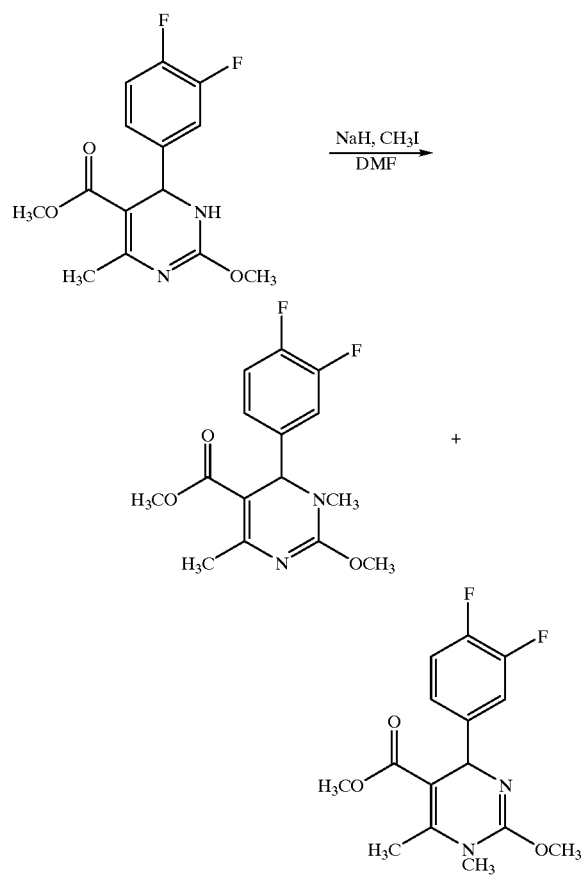

To a suspension of a 60% oil dispersion of NaH (96 mg, 2.2 mmol) in DMF (3 ml) at 0° C. was added a DMF solution (5 ml) of (+6-(3,4-Difluorophenyl)-2-methoxy-4-methyl-1,6-dihydro-pyrimidine-5-carboxylic acid methyl ester (592 mg, 2.0 mmol, [α$_D$]=+28°). After the mixture was stirred 30 min, a DMF solution (2 ml) of methyliodide (312 mg, 2.2 mmol) was added and the reaction stirred at room temperature for 45 min. The DMF was removed in vacuo, the residue treated with water and extracted with ethyl acetate(3X). The extracts were combined, washed with brine, dried over magnesium sulfate, filtered and concentrated in vacuo to give a crude oil (800 mg). Flash chromatography on silica gel (3% to 6% diethyl ether in methylene chloride) gave 6-(3,4-difluorophenyl)-2-methoxy-1,4-dimethyl-1,6-dihydro-pyrimidine-5-carboxylic acid methyl ester and 4-(3,4-difluorophenyl)-2-methoxy-1,6-dimethyl-1,4-dihydro-pyrimidine-5-carboxylic acid methyl ester as colorless oils.

Upper component, R$_f$=0.54 (5% ether in CH$_2$Cl$_2$). $^1$H NMR (CDCl$_3$): δ 7.26–7.00 (m, 3H), 5.18 (s, 1H), 3.90 (s, 3H), 3.62 (s, 3H), 2.83 (s, 3H), 2.36 (s, 3H).

Lower component, R$_f$=0.33 (5% ether in CH$_2$Cl$_2$). $^1$H NMR (CDCl$_3$): δ 7.27–6.98 (m, 3H), 5.55 (s, 1H), 3.77 (s, 3H), 3.66 (s, 3H), 3.11 (s, 3H), 2.49 (s, 3H).

Step C. (−)-4-(3,4-Difluorophenyl)-3,6-dimethyl-2-oxo-1,2,3,4-tetra-hydro-pyrimidine-5-carboxylic Acid Methyl Ester

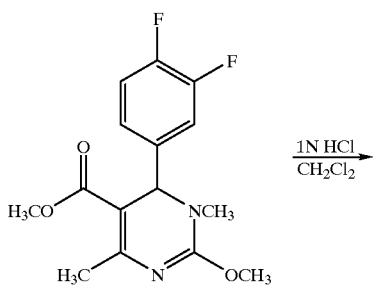

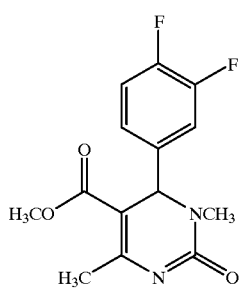

6-(3,4-Difluorophenyl)-2-methoxy-1,4-dimethyl-1,6-dihydro-pyrimidine-5-carboxylic acid methyl ester (278 mg, 0.896 mmol) was dissolved in methylene chloride (4 ml), treated with 1N HCl in ether (1.66 ml), and stirred at room temperature for 2 hrs. The solvent was removed in vacuo, the residue treated with water and saturated sodium bicarbonate (aq.) to adjust the pH=9.0, and extracted with ethyl acetate (3X). The extracts were combined, washed with brine, dried over magnesium sulfate, filtered, and concentrated in vacuo to give a white foam. Crystallization from diethyl ether gave the product as a white solid [$\alpha_D$]=−113°, c=0.20 CH$_2$Cl$_2$).

$^1$H NMR (CDCl$_3$): δ 7.60 (br s, lH), 7.19–7.07 (m, 3H), 5.19 (s, 1H), 3.67 (s, 3H), 2.86 (s, 3H), 2.34 (s, 3H).

Step D. (−)-4-(3,4-Difluorophenyl)-3,6-dimethyl-2-oxo-1,2,3,4-tetra-hydro-pyrimidine-5-carboxylic Acid

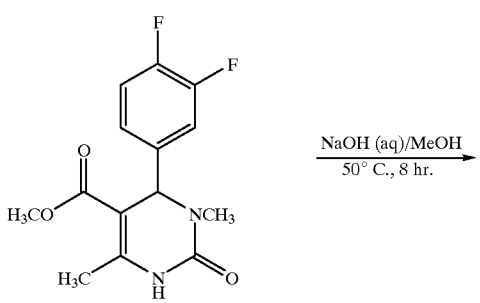

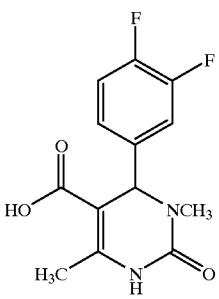

(−)-4-(3,4-Difluorophenyl)-3,6-dimethyl-2-oxo-1,2,3,4-tetrahydro-pyrimidine-5-carboxylic acid methyl ester (650 mg, 2.19 mmol) was dissolved in methanol (10 ml), treated with 2.5N sodium hydroxide (10 ml), and warmed to 500° C. for 8hr. The solvent was removed in vacuo, the remaining aqueous phase treated with 10% KHSO$_4$ (aq), and extracted with ethyl acetate (3X). The extracts were combined, washed with brine, dried over magnesium sulfate, filtered and concentrated to dryness in vacuo to give a crude oil. Crystallization from diethyl ether gave the product as a white solid [$\alpha_D$]=−128°, c=0.20 MeOH).

$^1$H NMR (DMSO): δ 9.37 (s, 1H), 7.47–7.38 (m, 1H), 7.31–7.24 (m, 1H), 7.14–7.07 (m, 1H), 5.19 (s, 1H), 2.71 (s, 3H), 2.23 (s, 3H).

EXAMPLE 15

(+)-(R)-4-(3,4-Difluorophenyl)-1,6-dimethyl-2-oxo-1,2,3,4-tetrahydro-pyrimidine-5-carboxylic Acid

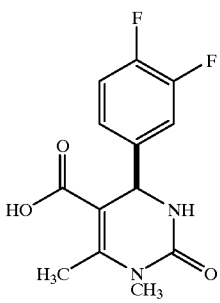

4-(3,4-Difluorophenyl)-2-methoxy-1,6-dimethyl-1,4-dihydro-pyrimidine-5-carboxylic acid methyl ester was converted to (+)-4-(3,4-difluorophenyl)-1,6-dimethyl-2-oxo-1,2,3,4-tetrahydro-pyrinidine-5-carboxylic acid following steps C and D above in Example 14 to give the product as a crystalline solid from diethyl ether ([$\alpha_D$]=+48°, c=0.145 MeOH).

$^1$H NMR (DMSO): δ 7.98 (d, 1H, J=3.9 Hz), 7.45–7.35 (m, 1H), 7.25–7.17 (m, 1H), 7.10–7.03 (m, 1H), 5.12 (d, 1H, J=3.9 Hz), 3.08 (s, 3H), 2.50 (s, 3H).

EXAMPLE 16

(R,S)-4-(3,4-Difluorophenyl)-1,3,6-trinethyl-2-oxo-1,2,3,4-tetrahydro-pyrimidine-5-carboxylic Acid

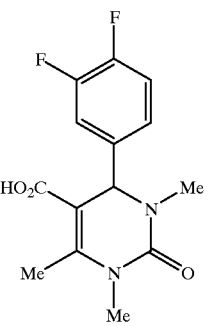

To a suspension of 4-(3,4-Difluorophenyl)-1,6-dimethyl-2-oxo-1,2,3,4-tetrahydro-pyrimidine-5-benzyl carboxylate (10 g, 26.9 mmol) in toluene (200 ml) is added dimethyl sulfate (3.05 ml, 32.2 mmol) followed by NaH (60% dispersion in oil, 1.13 g, 28.2 mmol) by portions. The reaction mixture is stirred at 60° C. for 3 hrs, allowed to cool to room temperature and diluted with diethyl ether and water. The organic layer is separated, washed with 1N HCl and brine, dried over $MgSO_4$, and concentrated in vacuo. The crude material is purified by flash chromatography (silica gel, 30% ethyl acetate in hexane to 40%) to provide 4-(R,S)-(3,4-difluorophenyl)-1,3,6tinmethyl-2-oxo-1,2,3,4-tetrahydro-pyrimidine-5-benzyl carboxylate. Hydrogenolysis of the previous benzyl ester (400 mg, 1.03 mmol) under similar conditions as described in Example 13 provides 4-(3,4-Difluorophenyl)-1,3,6-trimethyl-2-oxo-1,2,3,4-tetrahydro-pyrimidine-5-carboxylic acid (2).

$^1$H NMR ($CDCl_3$): δ 7.15–7.05 (m, 2H), 7.00–6.95 (m, 1H), 5.25 (s, 1H), 3.25 (s, 3H), 2.95 (s, 3H), 2.55 (s, 3H).

EXAMPLE 17

4-(3,4-Difluorophenyl)-1,6-dimethyl-3-acetyl-2-oxo-1,2,3,4-tetrahydro-pyrimidine-5-carboxylic Acid

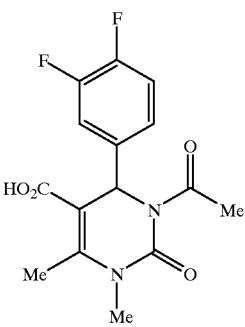

4-(3,4-Difluorophenyl)-1,6-dimethyl-3-acetyl-2-oxo-1,2,3,4-tetrahydro-pyzimidine-5-benzyl acetate is prepared using a similar procedure as described for the preparation of 4-(3,4-difluorophenyl)-1,3,6-trimethyl-2-oxo-1,2,3,4-tetrahydro-pyrimidine-5-benzyl acetate where dimethyl sulfate is substituted for acetic anhydride and toluene is substituted for DMF. Hydrogenolysis of the previous benzyl ester under similar conditions as described in example 13 provides 4-(3,4-Difluorophenyl)-1,6-dimethyl-3-acetyl-2-oxo-1,2,3,4-tetrahydro-pyrimidine-5-carboxylic acid.

$^1$H NMR ($CDCl_3$): δ 7.15–7.05 (m, 2H), 7.00–6.90 (m, 1H), 6.65 (s, 1H), 3.25 (s, 3H), 2.60 (s, 3H), 2.55 (s, 3H).

EXAMPLE 18

4-(3,4-Difluorophenyl)-1,6-dimethyl-3-carbomethoxy-2-oxo-1,2,3,4-tetrahydro-pyrimidine-5-carboxylic Acid

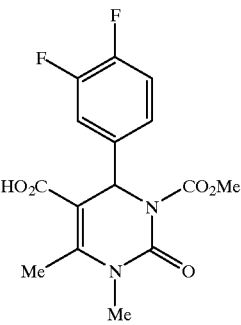

4-(3,4-Difluorophenyl)-1,6-dimethyl-3-carbomethoxy-2-oxo-1,2,3,4-tetrahydro-pyrimidine-5-benzyl acetate is prepared using a similar procedure as described for the preparation of 4(3,4-Difluorophenyl)-1,3,6-trimethyl-2-oxo-1,2,3,4-tetrahydro-pyrimidine-5-benzyl acetate where dimethyl sulfate is substituted for methyl chloroformate and toluene is substituted for THF. Hydrogenolysis of the previous benzyl ester under similar conditions as described in example XX provides 4-(3,4-Difluorophenyl)-1,6-dimethyl-3-carbomethoxy -2-oxo-1,2,3,4-tetrahydro-pyrimidine-5-carboxylic acid.

$^1$H NMR ($CDCl_3$): δ 7.20–7.05 (m, 2H), 7.00–6.90 (m, 1H), 6.35 (s, 1H), 3.95 (s, 3H), 3.20 (s, 3H), 2.55 (s, 3H).

EXAMPLE 19

(−)-4-Methoxymethyl-1,2,3,6-tetrahydro-2-oxo-6-(3,4-difluorophenyl)-pyrimidine-5-carboxylic Acid

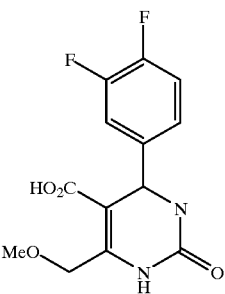

To a well stirred mixture of methyl 4-methoxyacetoacetate (50 g, 0.351 mol), 3,4-difiuorobenzaldehyde (51.39 g, 0.351 mmol), and urea (31.64 g, 0.527 mole) in THF (300 mL) at room temperature were added sequentially copper(I) oxide (5.06 g, 0.035 mole) and acetic acid (2.05 mL) followed by the dropwise addition of boron trifluoride diethyl etherate (56 mL, 0.456 mole). The mixture was stirred and refluxed for 8 h, whereupon TLC indicated completion of the reaction. It was cooled and poured into a mixture of ice and sodium bicarbonate (100 g). The resulting mixture was filtered through celite. The celite was washed with dichloromethane (400 mL). The organic layer was separated and the aqueous layer was extracted with dichloromethane (3×300 mL). The combined organic extracts were dried (sodium sulfate) and the solvent was evaporated. The crude product was purified by flash column chromatography on silica gel using 50% ethyl acetate in hexanes and then ethyl acetate as eluent to give the product as a pale yellow foam.

$^1$H NMR (CDCl$_3$) d 3.476 (s, 3H), 3.651 (s, 3H), 4.653 (s, 2H), 5.39 (s, 1H), 6.60 (br s, 1H, NH), 7.00–7.20 (m, 3H), 7.72 (br s, 1H, NH).

The racemic intermediate 5-methoxycarbonyl-4-methoxymethyl-1,2,3,6-tetrahydro-2-oxo-6-(3,4-difluorophenyl)-pyrimidine was resolved by chiral HPLC [Chiralcel OD 20×250 mm #369-703-30604; 1254 nm; hexanes/ethanol 90/10; 85 mg per injection; the 2nd enantiomer peak to elute] to give (−)-5-methoxycarbonyl-4-methoxymethyl-1,2,3,6-tetrahydro-2-oxo-6-(3,4-difluorophenyl)-pyrimidine. The material is hydrolyzed to the acid by standard means described previously.

EXAMPLE 20

(−)-4-Methyl-1,2,3,6-tetrahydro-2-oxo-6-(3,4-difluorophenyl)-pyrimidine-5-carboxylic Acid

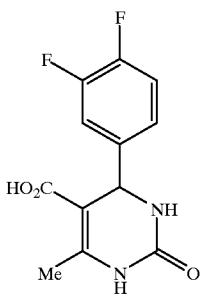

The title compound was prepared by procedures similar to those described above for Example 20 except substituting methyl acetoacetate for methyl 4-methoxyacetoacetate in the first step.

$^1$H NMR (DMSO): δ 9.3 (br s, 1H), 7.8 (br s, 1H), 7.43–7.35 (m, 1H),), 7.26–7.16 (m, 1H), ), 7.1–7.02 (m, 1H), 5.13 (s, lH), 2.34 (s, 3H).

EXAMPLE 21

(4R)-4-(3,4-Difluorophenyl)-6-methoxymethyl-2-oxo-1,2,3,4-tetrahydropyridine-5-carboxylic acid {3-[4-(2-cyano-4-fluorophenyl)-piperidin-1-yl]-propyl}-amide

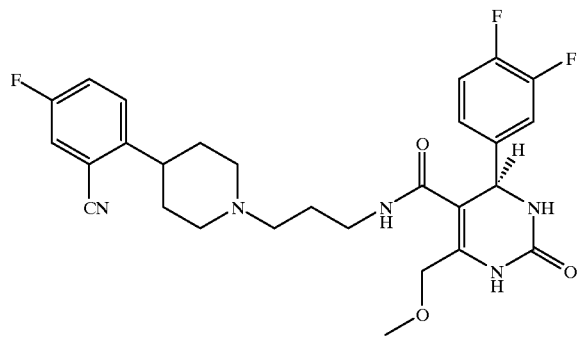

2-[1-(3-amino-propyl)-piperidin-4-yl]-5-fluoro-benzonitrile dihydrochloride (90 mg, 0.296 mmol), triethylamine (95.61, 0.688 mmol), 4-(R(3,4-difluorophenyl)-6-methoxymethyl-2-oxo-1,2,3,4-tetrahydro-pyrimidine-5-carboxylic acid (88.3 mg, 0.296 mmol), 1-ethyl-3-(3-dimethylaminopropyl)-carbodiimide Hydrochloride (56.6 mg, 0.296 mmol), and 1-hydroxybenzotriazole hydrate (40.0 mg, 0.296 mmol) were combined in dimethylformamide (2 ml) and stirred 24 hr at room temperature. After removal of the solvent in vacuo, the residue was treated with saturated sodium bicarbonate (aq.) and extracted with ethyl acetate (3X). The extracts were combined, washed with brine, dried over magnesium sulfate, filtered and concentrated in vacuo to give a crude oil (160 mg). Flash chromatography on silica gel (160/10/1 of methylene chloride/methanol/conc. ammonium hydroxide) gave as a white solid from ether.

Analysis: Calcd. for C$_{28}$H$_{30}$F$_3$N$_5$O$_3$. 0.01C$_4$H$_{10}$O. 0.55H$_2$O; C, 61.03; H, 5.79; N, 12.53; Found: C, 61.27; H, 5.69; N, 12.14.

The following examples were prepared using the procedure for Example 21 above with the noted reagent replacements.

EXAMPLE 22

(4R)-4-(3,4-Difluorophenyl)-6-methyl-2-oxo-1,2,3,4-tetrahydro-pyrimidine-5-carboxylic acid {3-[4-(2-cyano-4-fluorophenyl)-piperidin-1-yl]-propyl}-amide

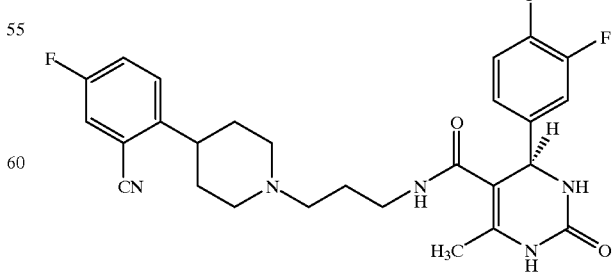

(4R)-4-(3,4-difluorophenyl)-6-methyl-2-oxo-1,2,3,4-tetrahydro-pyrimidine-5-carboxylic acid was used in place of (R)-4-(3,4-difluorophenyl)-6-methoxymethyl-2-oxo-1,2,3,4-tetrahydro-pyrimidine-5-carboxylic acid.

Analysis: Calcd. for $C_{27}H_{28}F_3N_5O_2 \cdot 0.05C_4H_{10} \cdot 0.55H_2O$; C, 62.20; H, 5.68; N, 13.34; Found: C, 62.44; H, 5.51; N, 12.94.

EXAMPLE 23

(4RS4-(3,4-Difluorophenyl)-6-methoxymethyl-2-oxo-1,2,3,4-tetrahydro-pyrimidine-6-carboxylic acid {3-[4-(2-cyanophenyl)-piperidin-1-yl]-propyl}-amide Hydrochloride

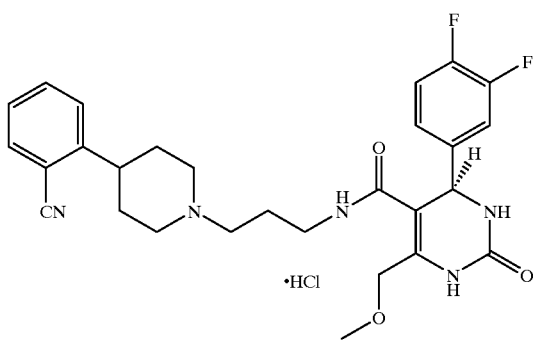

2-[1-(3-amino-propyl)-pipexidine-4-yl]-benzonitrile dihydrochloride was used in place of 2-[1-(3-amino-propyl)-piperidine-4-yl]-5-fluoro-benzonitrile dihydrochloride. The hydrochloride salt was prepared from ethyl acetate/ether with 1N hydrochloric acid in ether.

Analysis: Calcd. for $C_{28}H_{31}F2N_5O_{3\cdot HCl} \cdot 0.15C_4H_{10}O \cdot 0.60H_2O$; C, 59.02; H, 6.01; N, 12.03; Found: C, 59.02; H, 5.88; N, 11.64.

EXAMPLE 24

(4R)-4-(3,4-Difluorophenyl)-6-methyl-2-oxo-1,2,3,4-tetrahydro-pyrimidine-5-carboxylic acid {3-[4-(2-cyanophenyl)-piperidin-1-yl]-propyl}-amide

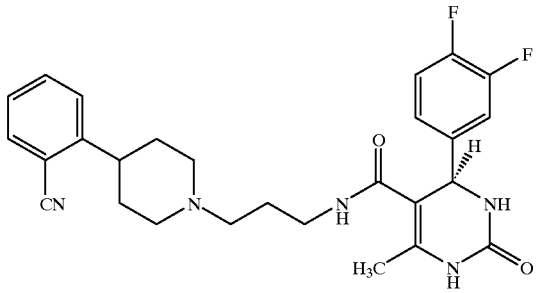

2-[1-(3-amino-propyl)-piperidine-4-yl]-benzonitrile dihydrochloride as used in place of 2-[1-(3-amino-propyl)-piperidine-4-yl]-5-fluoro-enzonitrile dihydrochloride and (R)-4-(3,4-difluorophenyl)-6-methyl-2-oxo-1,2,3,4-tetrahydro-pyrimidine-5-carboxylic acid was used in place of (R)-4-(3,4-difluorophenyl)-6-methoxymethyl-2-oxo-1,2,3,4-tetrahydro-pyrimidine-5-carboxylic acid.

Analysis: Calcd. for $C_{27}H_{29}F2N_5O_2 \cdot 0.40H_2O$; C, 64.75; H, 6.00; N, 13.99; Found: C, 64.84; H, 6.28; N, 13.60.

EXAMPLE 25

(4R)-4-(3,4-Difluorophenyl)-6-methoxymethyl-2-oxo-1,2,3,4-tetrahydro-pyrimidine-5-carboxylic acid {3-[4-(4-fluorophenyl)-4-hydroxy-piperidin-1-yl]-propyl}-amide.

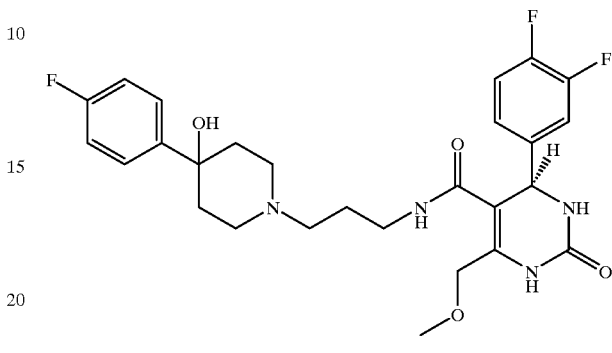

1-(3-Amino-propyl)-4-(4-fluorophenyl)-piperidine-4-ol dihydrochloride was used in place of 2-[1-(3-Amino-propyl)-pipexidine-4-yl]-5-fluoro-benzonitrile dihydrochloride.

Analysis: Calcd. for $C_{27}H_{31}F_3N_4O_4 \cdot .65H_2O$; C, 59.58; H, 5.98; N, 10.29; Found: C, 59.29; H, 6.01; N, 10.14.

EXAMPLE 26

(4R)-4-(3,4-Difluorophenyl)-6-methyl-2-oxo-1,2,3,4-tetrahydro-pyrimidine-5-carboxylic acid {3-[4-(4-fluorophenyl)-4-hydroxy-piperidin-1-yl]-propyl}-amide

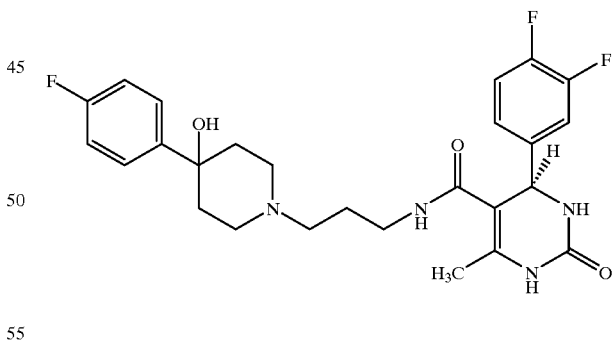

1-(3-Amino-propyl)-4-(4-fluorophenyl)-piperidine-4-ol dihydrochloride was used in place of 2-(1-(3-Amino-propyl)-piperidine-4-yl]-5-fluoro-benzonitrile dihydrochloride and (4R)-4-(3,4-difluorophenyl)-6-methyl-2-oxo-1,2,3,4-tetrahydro-pyrimidine-5-carboxylic acid was used go in place of (4R)-4-(3,4-difluorophenyl)-6-methoxymethyl-2-oxo-1,2,3,4-tetrahydro-pyrimidine-5-carboxylic acid.

Analysis: Calcd. for $C_{26}H_{29}F_3N_4O_3 \cdot 0.80H_2O$; C, 60.40; H, 5.97; N, 10.84; Found: C, 60.19; H, 5.98; N, 10.77.

EXAMPLE 27

(4R)-4-(3,4-Difluorophenyl)-6-methoxymethyl-2-oxo-1,2,3,4-tetrahydro-pyrimidine-5-carboxylic acid [3-(3',4',5',6'-tetrahydro-2'H-[2,4']bipyridinyl-1'-yl)-propyl]-amide Dihydrochloride

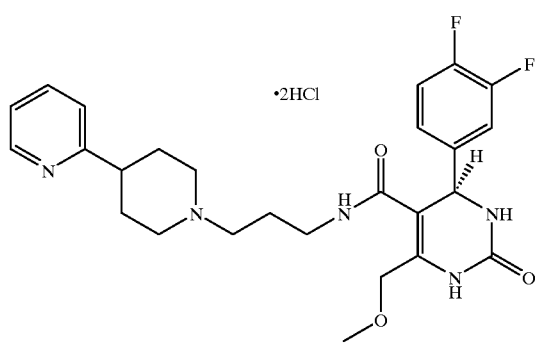

3-(3',4',5',6'-Tetrahydro-2'H-(2,41bipyridinyl-1'-yl)-propylamine trihydrochloride was used in place of 2-[1-(3-amino-propyl)-piperidine-4-yl]-5-fluoro-benzonitrile dihydrochloride. The hydrochloride salt was prepared from ethyl acetate/ether with 1N hydrochloric acid in ether.

Analysis: Calcd. for $C_{26}H_{31}F2N_5O_3.2HCl.0.85H_2O$; C, 53.12; H, 5.95; N, 11.92; Found: C, 52.85; H, 6.13; N, 11.83.

EXAMPLE 28

(4R)-4-(3,4-Difluorophenyl)-6-methyl-2-oxo-1,2,3,4-tetrahydro-pyrimidine-5-carboxylic acid [3-(3',4',5',6'-tetrahydro-2'H-[2,4']bipyridinyl-1'-yl)-propyl]-amide

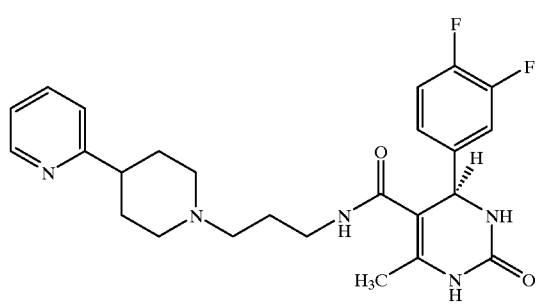

3-(3',4',5',6'-Tetrahydro-2'H-[2,4']bipyridinyl-1'-yl)-propylamine trihydrochoride was used in place of 2-[1-(3-amino-propyl)-piperidine-4-yl]-5-fluoro-benzonitrile dihydrochloride and (4R)-4-(3,4-difluorophenyl)-6-methyl-2-oxo-1,2,3,4-tetrahydro-pyrimidine-5-carboxylic acid was used in place of (4R)-4-(3,4-difluorophenyl)-6-methoxymethyl-2-oxo-1,2,3,4-tetrahydro-pyrimidine-5-carboxylic acid.

Analysis: Calcd. for $C_{25}H_{29}F2N_5O_2$; C, 63.95; H, 6.23; N, 14.92; Found: C, 64.02; H, 6.29; N, 14.74.

The following examples were prepared by procedures similar to those described above in Example 21 except substituting the appropriate reagents.

EXAMPLE 29

(−)-4-(3,4-Difluorophenyl)-2-oxo-1,2,3,4-tetrahydro-pyrimidine-5-carboxylic acid {3-[4-(2-cyanophenyl)-piperidin-1-yl]-propyl}-amide

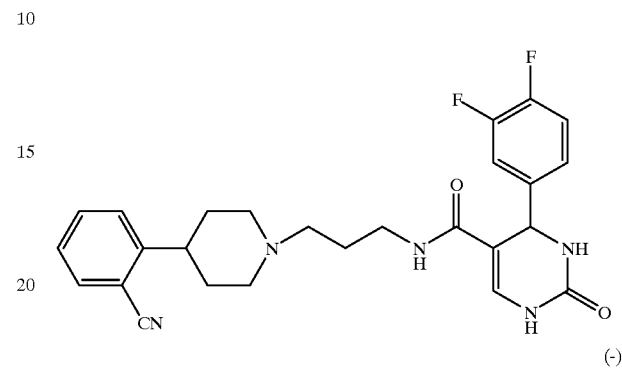

Analysis: Calcd. for $C_{26}H_{27}F2N_5O_2.0.60$ EtOAc; C, 63.68; H, 5.80; N, 14.28;

Found: C, 63.66; H, 5.81; N, 14.64.

EXAMPLE 30

(−)-4-(3,4-Difluorophenyl)-2-oxo-1,2,3,4-tetrahydro-pyrimidine-5-carboxylic acid {3-[4-(4-fluorophenyl)-piperidin-1-yl]-propyl}-amide

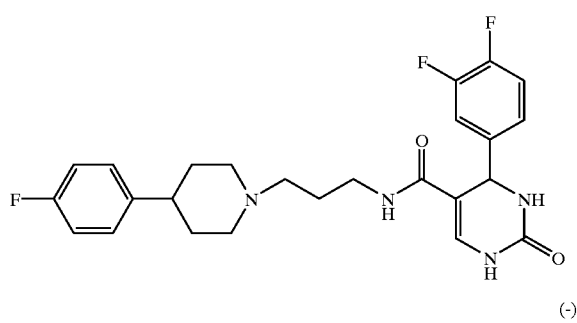

Analysis: Calcd. for $C_2SH_{27}F_3N_4O_2.2.20$ $H_2O.0.20$ EtOAc; C, 58.49; H 6.28; N, 10.58;

Found C, 58.51; H 5.89; N, 10.49.

EXAMPLE 31

(−)-4-(3,4-Difluorophenyl)-6-methyl-2-oxo-1,2,3,4-tetrahydro-pyrimidine-5-carboxylic acid [3-[4-(4-fluorophenyl)-piperidin-1-yl]-propyl]-amide Hydrochloride

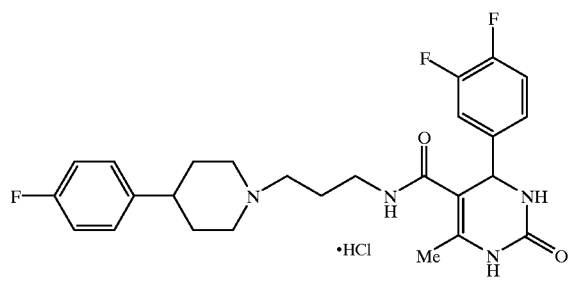

Analysis: Calcd. for $C_{26}H_{29}F_3N_4O_2 \cdot HCl \cdot 1.5$ EtOAc; C, 57.43; H, 6.33; N, 10.47; Found: C, 57.46; H, 5.93; N, 10.44.

EXAMPLE 32

(−)-4-(3,4-Difluorophenyl)-6-methoxymethyl-2-oxo-1,2,3,4-tetrahydro-pyrimidine-5-carboxylic acid {3-[4-(4-fluorophenyl)-piperidin-1-yl]-propyl}-anide

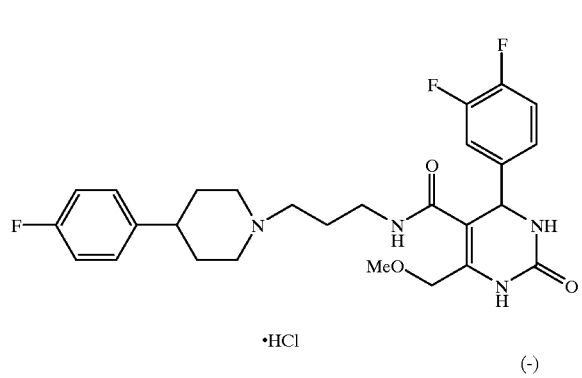

Analysis: Calcd. for $C_{27}H_{31}F_3N_4O_3 \cdot 0.25$ $H_2O$; C, 62.23; H, 6.09; N, 10.75; Found: C, 62.17, H, 6.07; N, 10.89.

EXAMPLE 33

(−)-4-(3,4-Difluorophenyl)-2-oxo-1,2,3,4-tetrahydro-pyrimidine-5-carboxylic acid {3-[4-(4-fluorophenyl)-4-hydroxy-piperidin-1-yl]-propyl}-amide Hydrochloride

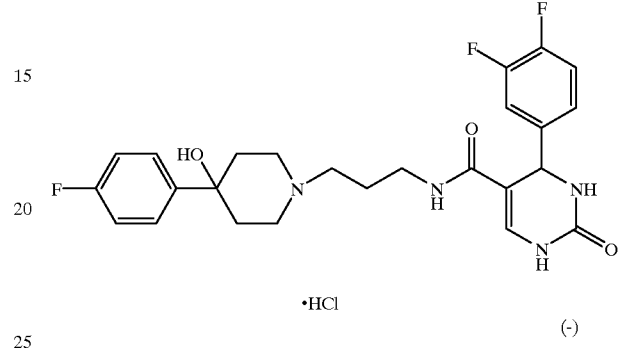

Analysis: Calcd. for $C_{25}H_{27}F_3N_4O_3 \cdot HCl \cdot 1.75H_2O$; C, 53.95; H, 5.71; N, 10.07; Found: C, 53.93; H, 5.60; N, 10.58.

EXAMPLE 34

(−)-4-(3,4-Difluorophenyl)-2-oxo-1,2,3,4-tetrahydro-pyrimidine-5-carboxylic acid {3-[4-(2-cyano-4-fluorophenyl)-piperidin-1-yl]-propyl}-amide Hydrochloride

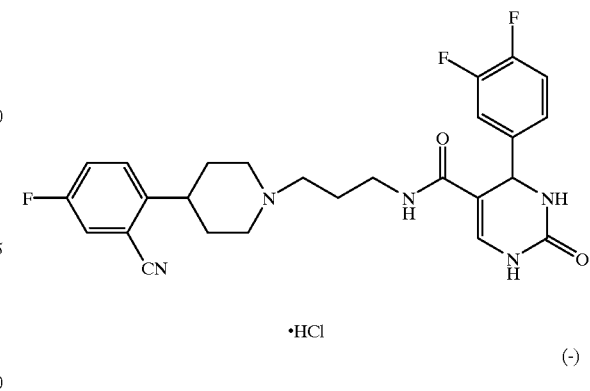

Analysis: Calcd. for $C_{26}H_{26}F_3N_5O_2 \cdot HCl \cdot 1.80$ $H_2O$; C, 55.23; H, 5.28; N, 12.39; Found: C, 55.22; H, 5.24; N, 12.96.

EXAMPLE 35

(−)-4-(3,4-Diuorophenyl)-2-oxo-1,2,3,4-tetrahydro-pyrimidine-5-carboxylic acid [3-(3',4',5',6'-tetrahydro-2'H-[2,4']bipyridinyl-1'-yl)-propyl]-amide Dihydrochloride

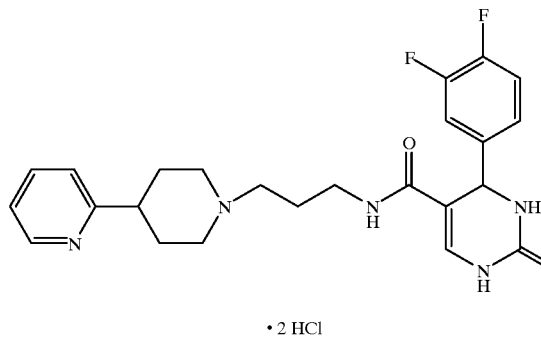

Analysis: Calcd. for $C_{24}H_{27}F2N_5O_2 \cdot HCl \cdot 2.00\ H_2O \cdot 0.45$ EtOAc; C, 51.29; H, 6.11; N, 11.59; Found: C, 51.28; H, 6.00; N, 11.58.

EXAMPLE 36

(−)-4-(3,4-Difluorophenyl)-2-oxo-1,2,3,4-tetrahydro-pyrimidine-5-carboxylic acid {3-[4-cyano-4-(fluorophenyl)-piperidin-1-yl]-propyl}-amide Hydrochloride

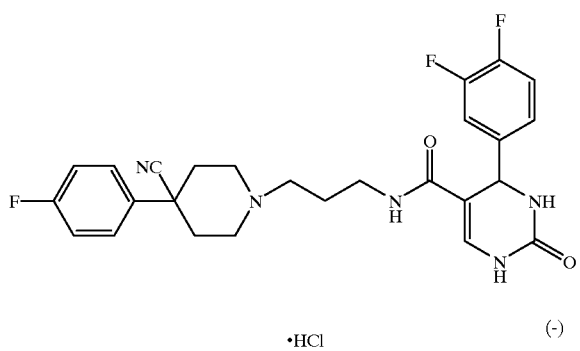

Analysis: Calcd. for $C_{26}H_{26}F_3N_5O_2 \cdot HCl \cdot 1.55\ H_2O$; C, 55.57; H, 5.40; N, 12.46; Found: C, 55.58; H, 5.25; N, 12.47.

EXAMPLE 37

(−)-4-(3,4-Difluorophenyl)-6methyl-2-ox1,2,3,4-tetrahydro-pyrimidine-5-carboxylic acid {³-[⁴-cyano-4-(⁴-(4-fluorophenyl)-piperidin-1-yl]-propyl}-amide Hydrochloride

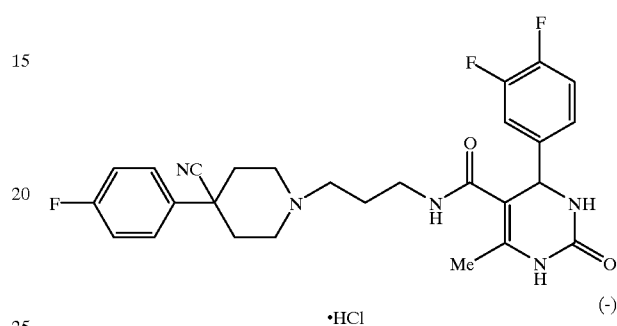

Analysis: Calcd. for $C_{27}H_{28}F_3N_5O_2 \cdot HCl \cdot 1.75\ H_2O \cdot 0.55$ EtOAc; C, 55.84; H, 5.92; N, 11.15; Found: C, 55.84; H, 5.54; N, 11.13.

EXAMPLE 38

(−)-4-(3,4-Difluorophenyl)-2-oxo-1,2,3,4-tetrahydro-pyrmidine-5-carboxylic acid {3-[4-cyano-4-(2-cyanophenyl)piperidin-1-yl]-propyl)}-amide Hydrochloride

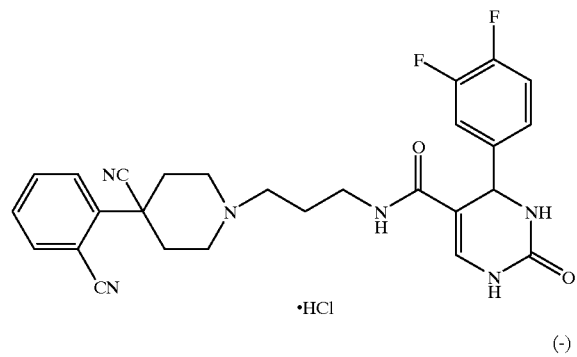

Analysis: Calcd. for $C_{27}H_{26}F2N_6O_2 \cdot HCl \cdot 0.95\ H_2O \cdot 0.25$ EtOAc; C, 57.96; H, 5.37; N, 14.49; Found: C, 57.96; H, 5.01; N, 14.45.

EXAMPLE 39

4-(3,4-Difluorophenyl)-6-methyl-2-oxo-1,2,3,4-tetrahydro-pyrimidine-5-carboxylic acid {3-[4-cyano-4-(2-cyanophenyl)-piperidin-1-yl]-propyl}-amide Hydrochloride

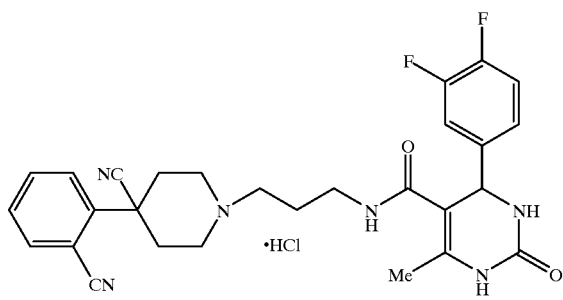

Analysis: Calcd. for $C_{28}H_{28}F_2N_6O_2 \cdot HCl \cdot 1.8\ H_2O$; C, 57.34; H, 5.43; N, 14.33; Found: C, 57.33; H, 5.47; N, 14.32.

EXAMPLE 40

4-(3,4-Difluorophenyl)-1-methyl-2-oxo-1,2,3,4-tetrahydro-pyrinidine-5-carboxylic acid {3-[4-cyano-4-(2,4-difluorophenyl)-piperidin-1-yl]-propyl}-amide

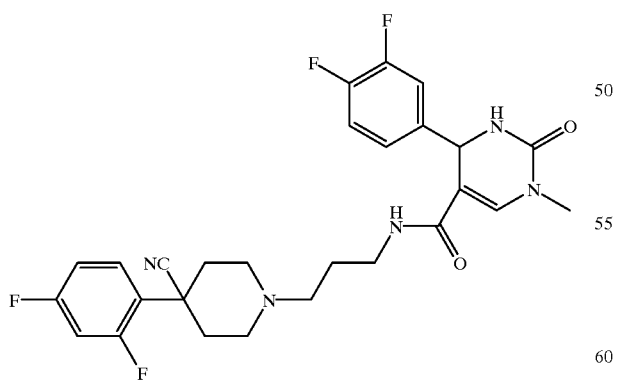

Analysis: Calcd. for $C_{27}H_{27}F_4N_5O_2 \cdot 0.45\ H_2O$; C, 60.31; H, 5.23; N, 13.03; Found: C, 60.30; H, 5.08; N, 13.14.

EXAMPLE 41

(+)-4-(3,4-Difluorophenyl)-1-methyl-2-oxo-1,2,3,4-tetrahydro-pyrimidine-5-carboxylic acid {3-[4-cyano-4-(4-fluorophenyl)piperidin-1-yl]-propyl}-amide

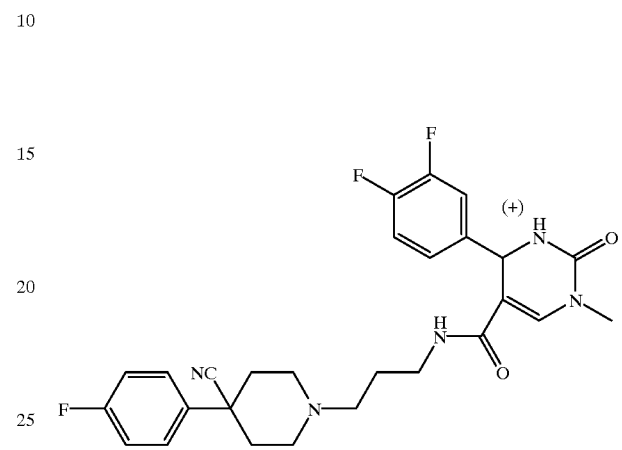

Analysis: Calcd. for $C_{27}H_{28}F_3N_5O_2 \cdot 0.45\ H_2O$; C, 62.40; H, 5.61; N, 13.48; Found: C, 62.38; H, 5.52; N, 13.61.

EXAMPLE 42

4-(3,4-Difluorophenyl)-1-methyl-2-oxo-1,2,3,4-tetrahydro-pyrimidine-5-carboxylic acid {3-[4-(4-fluorophenyl)-piperidin-1-yl]-propyl}-amide

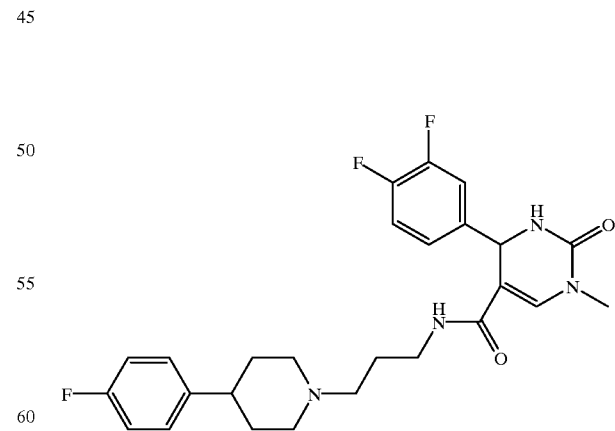

Analysis: Calcd. for $C_{26}H_{29}F_3N_4O_2 \cdot 2.5\ H_2O$; C, 58.74; H, 6.45; N, 10.54; Found: C, 58.35; H, 5.69; N, 10.65.

EXAMPLE 43

4-(3,4-Difluorophenyl)-1,3-dimethyl-2-oxo-1,2,3,4-tetrahydro-pyrimidine-5-carboxylic acid {3-[4-cyano-4-(4-fluorophenyl)-piperidin-1-yl]-propyl)-amide

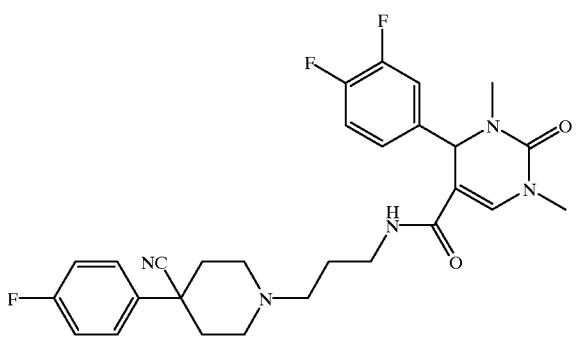

Analysis: Calcd. for $C_{28}H_{30}F_3N_5O_2 \cdot 0.95\ H_2O$; C,61.97; H, 5.93; N, 12.91; Found: C, 61.92; H, 5.69; N, 13.02.

EXAMPLE 44

4-(3,4-Difluorophenyl)-1,3-dimethyl-2-oxo-1,2,3,4-tetrahydro-pyrimidine-5-carboxylic acid {3-[4-(2-cyano-4-fluorophenyl)-piperidin-1-yl]-propyl}-amide

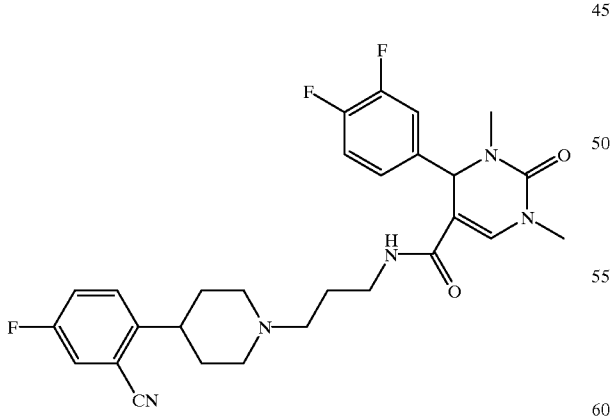

Analysis: Calcd. for $C_{28}H_{30}F_3N_5O_2 \cdot 0.85\ H_2O$; C,62.17; H, 5.91; N, 12.95; Found: C, 62.12; H, 5.92; N, 13.18.

EXAMPLE 45

4-(3,4-Difluorophenyl)-1,3-dimethyl-2-oxo-1,2,3,4-tetrahydro-pyrimidine-5-carboxylic acid {3-[4-(4-fluorophenyl)-piperidin-1-yl]-propyl}-amide Hydrochloride

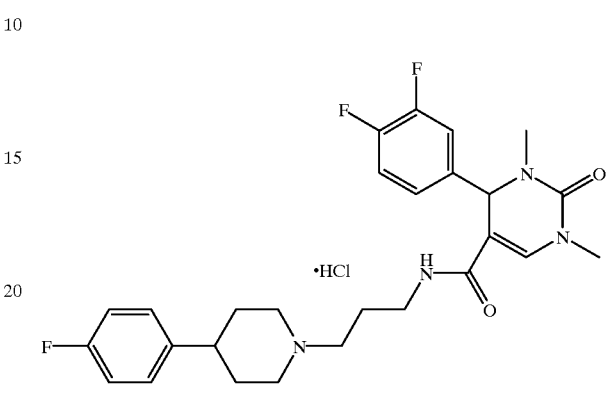

Analysis: Calcd. for $C_{27}H_{31}F_3N_4O_2 \cdot HCl \cdot 2.50\ H_2O \cdot 0.05$ EtOAc; C,55.70; H, 6.43; N, 9.55; Found: C, 55.64; H,6.43; N,9.55.

EXAMPLE 46

4-(3,4-Difluorophenyl)-1,3-dimethyl-2-oxo-1,2,3,4-tetrahydro-pyrimidine-5-carboxylic acid {3-[4-cyano-4-(2,4-difluorophenyl)-piperidin-1-yl]-propyl}-amide Hydrochloride Analysis: Calcd for $C_{28}H_{29}F_4N_5O2 \cdot HCl \cdot 1.95\ H_2O \cdot 0.30$ EtOAc; C,54.66; H, 5.70; N,10.92; Found: C, 54.64; H,5.32; N,10.87.

EXAMPLE 47

4-(3,4-Difluorophenyl)-1-methyl-2-oxo-1,2,3,4-tetrahydro-pyrimidine-5-carboxylic acid {3-[4-(4-fluorophenyl)-4-hydroxy-piperidin-1-yl]-propyl}-amide Hydrochloride

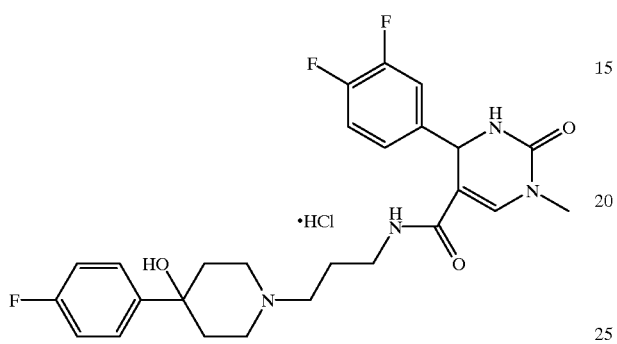

Analysis: Calcd. for $C_{26}H_{29}F_3N_4O_3 \cdot HCl \cdot 0.55\ H_2O$; C,56.89; H, 5.71; N,10.21; Found: C, 56.84; H,5.69; N,10.20.

EXAMPLE 48

4-(3,4-Difluorophenyl)-1-methyl-2-oxo-1,2,3,4-tetrahydro-pyrimidine-5-carboxylic acid {3-[4-(2-cyano-4-fluorophenyl)-piperidin-1-yl]-propyl}-amide

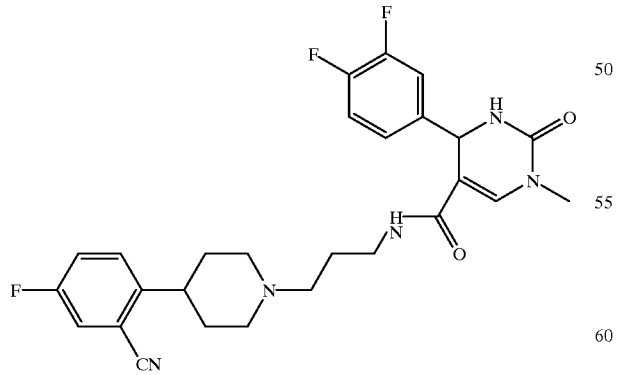

Analysis: Calcd. for $C_{27}H_{28}F_3N_5O_2 \cdot 0.10$ EtOAc; C, 63.24; H,5.58; N,13.46; Found: C, 63.32; H,5.54; N,13.40.

EXAMPLE 49

(−)-4-(3,4-Difluorophenyl)-1-methyl-2-oxo-1,2,3,4-tetrahydro-pyrimidine-5-carboxylic acid {3-[4-cyano-4-(4-fluorophenyl)-piperidin-1-yl]-propyl}-amide Hydrochloride

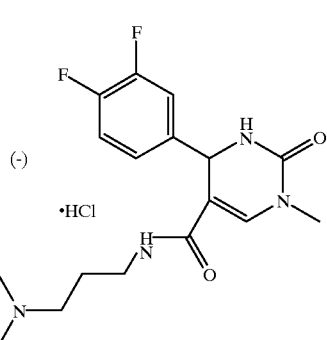

Analysis: Calcd. for $C_{27}H_{28}F_3N_5O_2 \cdot HCl \cdot 0.80\ H_2O \cdot 0.35$ EtOAc; C, 57.49; H,5.67; N,11.81; Found: C, 57.52; H,5.74; N,11.80.

EXAMPLE 50

4-(3,4-Difluorophenyl)-1-methyl-2-oxo-1,2,3,4-tetrahydro-pyrimidine-5-carboxylic acid {3-[2-cyano-4-fluorophenyl)-4-cyanopiperidin-1-yl]-propyl}amine

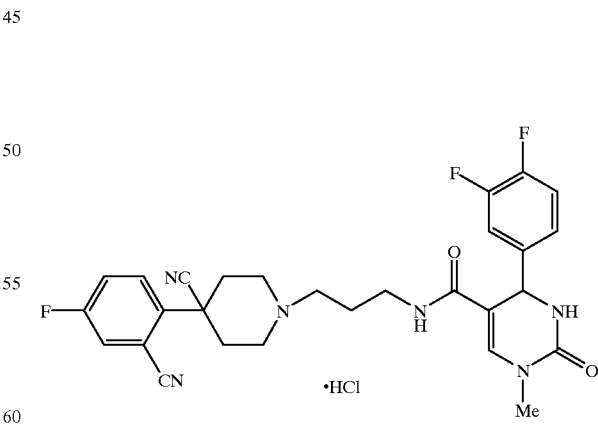

Calculated for $C_{28}H_{29}N_6O_2F_3Cl_1 \cdot 1.10\ H_2O$, 0.1 EtOAc: C=56.64% H=5.00% N=14.05%. Found: C=56.69% H=5.19% N=13.97%; mass spectrum M+H=537, calc 537.

EXAMPLE 51

4-(3,4-Difluorophenyl)-1,3-dimethyl-2-oxo-1,2,3,4-tetrahydro-pyrimidine-5-carboxylic acid {3-[2-cyano-4-fluorophenyl)-4-cyanopiperidin-1-yl]-propyl}amine

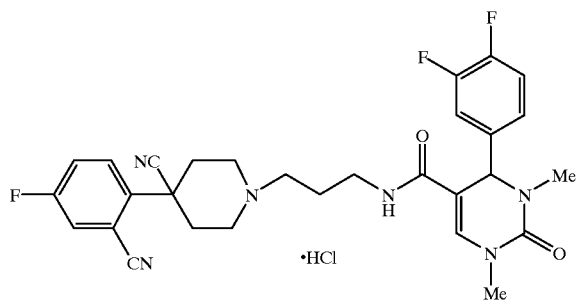

Calculated for $C_{29}H_{30}N_6O_2F_3Cl_1 \cdot 1.55$ $H_2O$, 0.1 hexane: C=57.01% H=5.58% N=13.48%. Found: C=56.98% H=5.21% N=13.22%; mass spectrum M+H=551, calc 551.

EXAMPLE 52

4-(3,4-Difluorophenyl)-1,6-dimethyl-2-oxo-1,2,3,4-tetrahydro-pyzrindine-5-carboxylic acid {3-[2-cyano-4-fluorophenyl)-piperidin-1-yl]-propyl}amine

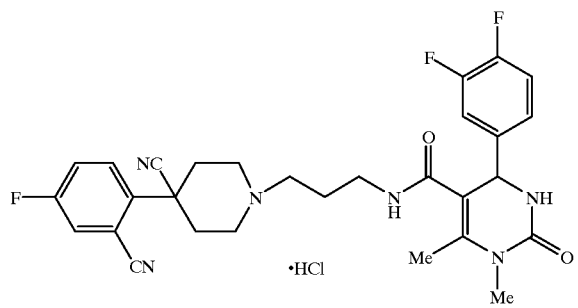

Calculated for $C_{29}H_{29}N_6O_2F_3 \cdot$ 0.2 $H_2O$: C=62.85% H=5.35% N=15.17%. Found: C=62.89% H=4.99% N=15.16%; mass spectrum M+H=551, calc 551.

EXAMPLE 53

4-(3,4-Difluorophenyl)-1,6-dimethyl-2-oxo-1,2,3,4-tetrahydro-pyrimidine-5-carboxylic acid {3-[4-(4-fluorophenyl)-piperidine-1-yl]-propyl}-amide

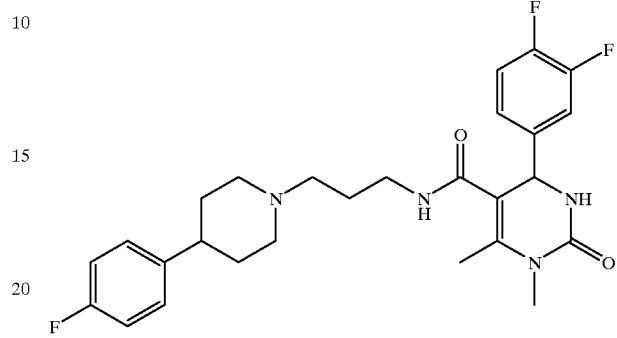

4-(3,4-Difluorophenyl)-1,6-dimethyl-2-oxo-1,2,3,4-tetrahydro-pyrimidine-5-carboxylic acid is coupled to 1-(3-aminopropyl)-4-(4-fluorophenyl)-piperidine dihydrochloride under EDC/HOAt conditions similar to those described earlier to provide the product as a white solid.

Analysis: Calcd. for $C_{27}H_{31}F_3N_4O_2 \cdot 1.2$ $H_2O$; C, 62.10; H, 6.45; N, 10.73; Found: C, 61.94; H, 6.05; N, 10.57.

The racemic material was resolved by preparative HPLC (Chiralpak AD, 70:30 0.1% diethyl amine in hexane: ethanol) to provide both enantiomers: $[\alpha]_D$=+87.7 (c=0.22, CDCl$_3$) and: $[\alpha]_D$=−97.1 (c=0.22, CDCl$_3$).

EXAMPLE 54

(R)-4-(3,4-Difluorophenyl)-1,6-dimethyl-2-oxo-1,2,3,4-tetrahydro-pyrimidine-5-carboxylic acid {3-[4-(4-fluorophenyl)-4-cyanopiperidine-1-yl]-propyl}-amide

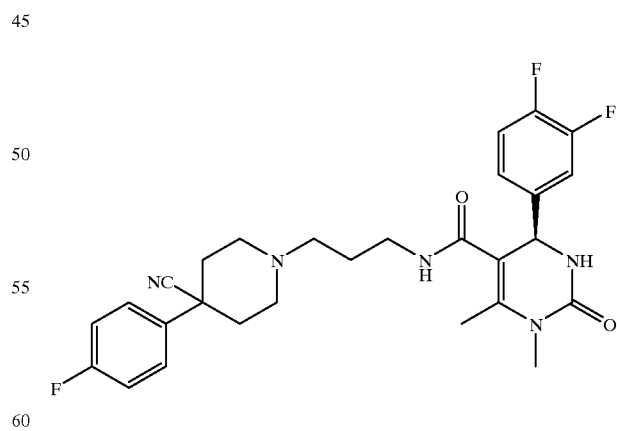

(R)-4-(3,4-Difluorophenyl)-1,6-dimethyl-2-oxo-1,2,3,4-tetrahydro-pyrimidine-5-carboxylic acid (preparation described earlier) is coupled to 1-(3-aminopropyl)-4-(4-fluorophenyl)-4-cyanopiperidine dihydrochloride under EDC/HOAt conditions similar to those described earlier to provide product as a white solid.

Analysis: Calcd. for $C_{28}H_{30}F_3N_5O_2 \cdot 0.15\ H_2O$; C, 63.66; H, 5.78; N, 13.26; Found: C, 63.65; H, 5.88; N, 12.91.

EXAMPLE 55

(R)-4-(3,4-difluorophenyl)-1,6-dimethyl-2-oxo-1,2,3,4-tetrahydro-pyrimidine-5-carboxylic acid {3-[4-(2,4-difluorophenyl)-4-cyano-piperidine-1-yl]-propyl}-amide

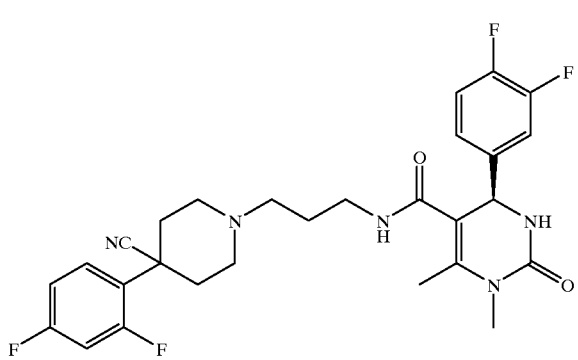

(R)-4-(3,4-Difluorophenyl)-1,6-dimethyl-2-oxo-1,2,3,4-tetrahydro-pyrimidine-5-carboxylic acid (preparation described earlier) is coupled to 1-(3-aminopropyl)-4-(2,4-difluorophenyl)-4-cyano-piperidine dihydrochloride under EDC/HOAt conditions similar to those described earlier to provide as a white solid.

Analysis: Calcd. for $C_{28}H_{29}F_4N_5O_2 \cdot 0.4\ H_2O$; C, 61.06; H, 5.45; N, 12.72; Found: C, 61.05; H, 5.56; N, 12.54.

EXAMPLE 56

4-(3,4-Difluorophenyl)-1,3,6-trimethyl-2-oxo-1,2,3,4-tetrahydro-pyrimidine-5-carboxylic acid-{3-[4-(4-fluorophenyl)-piperidine-1-yl]-propyl}-amide

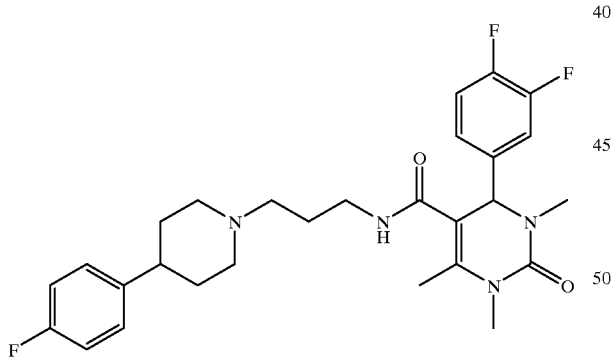

4-(3,4-Difluorophenyl)-1,3,6-trimethyl-2-oxo-1,2,3,4-tetrahydro-pyrimidine-5-carboxylic acid is coupled to 1-(3-aminopropyl)-4-(4-fluorophenyl)-piperidine dihydrochloride under EDC/HOAt conditions similar to those described earlier to provide as a white solid.

Analysis: Calcd. for $C_{28}H_{33}F_3N_4O_2 \cdot 0.8\ H_2O$; C, 63.57; H, 6.59; N, 10.59; Found: C, 63.52; H, 6.55; N, 10.30.

The racemic material was resolved by preparative HPLC (Chiralpak AD, 70:30 0.1% diethyl amine in hexane:ethanol) to provide both enantiomers as hydrochlorides after salt preparation with 1N HCl: $[\alpha]_D=+40.0$ (c=0.1, MeOH) and: $[\alpha]_D=-30.0$ (c=0.12, MeOH).

EXAMPLE 57

(R) and (S)-4-(3,4-Difluorophenyl)-1,3,6-trimethyl-2-oxo-1,2,3,4-tetrahydro-pyrimidine-5-carboxylic acid {3-[4-(4-fluorophenyl)-4-cyanopiperidine1-yl]-propyl}-amide Hydrochloride

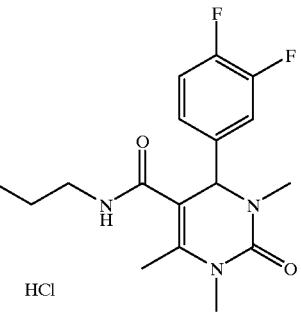

4-(3,4-difluorophenyl)-1,3,6-trimethyl-2-oxo-1,2,3,4-tetrahydro-pyrimidine-5-carboxylic acid is coupled to 1-(3-aminopropyl)-4-(4-fluorophenyl)-4-cyanopiperidine dihydrochloride under EDC/HOAt conditions similar to those described earlier to provide as a white solid, after hydrochloride preparation with 1N HCl.

The racemic material was resolved by preparative HPLC (Chiralpak AD, 80/20: 0.1% diethyl amine in hexane:EtOH) to provide both enantiomers: and:

$[\alpha]_D=+34.7$ (c=0.17, MeOH); Analysis: Calcd. for $C_{29}H_{32}F_3N_5O_2 \cdot HCl \cdot 0.85\ H_2O \cdot 0.25\ Et_2O$; C, 59.07; H, 6.15; N, 11.48; Found: C, 59.06; H, 5.75; N, 11.23; $[\alpha]_D=-34.1$ (c=0.14, MeOH).

Analysis: Calcd. for $C_{29}H_{32}F_3N_5O_2 \cdot HCl \cdot 0.45\ H_2O \cdot 0.25\ Et2O$; C, 59.78; H, 6.09; N, 11.62; Found: C, 59.78; H, 5.74; N, 11.38.

EXAMPLE 58

(+) and (−)-4-(3,4-Difluorophenyl)-1,3,6-trimethyl-2-oxo-1,2,3,4-tetrahydro-pyrimidine-5-carboxylic acid {3-[4-(2,4-difluorophenyl)-4-cyano-piperidine-1-yl]-propyl}-amide Hydrochloride

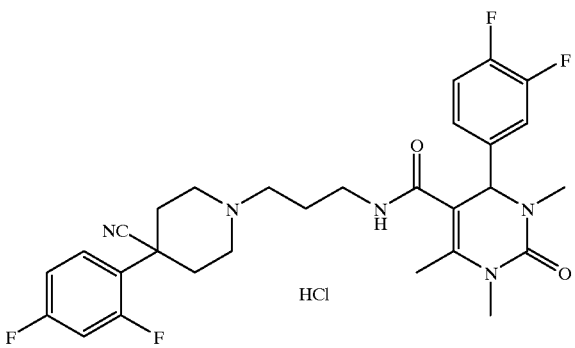

4-(3,4-difluorophenyl 1,3,6-trimethyl-2-oxo-1,2,3,4-tetrahydro-pyrimidine-5-carboxylic acid is coupled to 1-(3-aminopropyl)-4-(2,4-difluorophenyl)-4-cyano-piperidine dihydrochloride under EDC/HOAt conditions similar to those described earlier to provide as a white solid, after hydrochloride preparation with 1N HCl. The racemic material was resolved by preparative HPLC (Chiralpak AD, 80:20 0.1% diethyl amine in hexane:EtOH) to provide both enantiomers:

$[\alpha]_D$=+29.8 (c=0.29, MeOH); Analysis: Calcd. for $C_{29}H_{31}F_4N_5O_2$.HCl.0.05 $H_2O$.0.5 $CH_2Cl_2$; C, 55.58; H, 5.23; N, 10.99; Found: C, 55.60; H, 5.26; N, 10.95. $[\alpha]_D$=−26.3 (c=0.18, MeOH); Analysis: Calcd. for $C_{29}H_{31}F_4N_5O_2$.HCl.0.25 $H_2O$.0.2 $CH_2Cl_2$; C, 55.58; H, 5.23; N, 10.99; Found: C, 55.60; H, 5.26; N, 10.95.

EXAMPLE 59

4-(3,4Difluorophenyl)-1,6-dimethyl-3-acetyl-2-oxo-1,2,3,4-tetrahydro-pyrimidine-5-carboxylic acid {3-[4-(4-fluorophenyl)-piperidine-1-yl]-propyl}-amide Hydrochloride

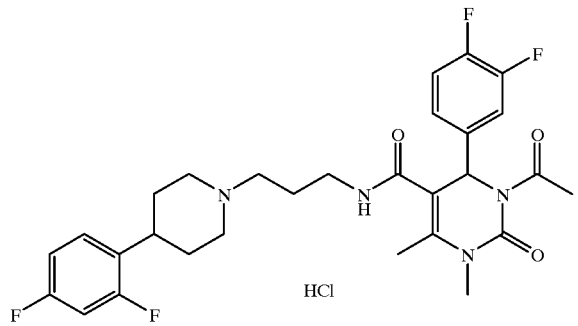

4-(3,4-difluorophenyl)-1,6dimnethyl-3-acetyl-2-oxo-1,2,3,4-tetrahydro-pyrrnidine-5-carboxylic acid is coupled to 1-(3-aminopropyl)-4-(4-fluorophenyl)-piperidine dihydrochioride under EDC/HOAt conditions simnilar to those described earlier to provide as a white solid, after hydrochloride preparation with 1N HCl.

Analysis: Caled. for $C_{29}H_{34}F_3N_4O_3Cl$.0.9 $H_2O$; C, 58.84; H, 6.46; N, 8.91; Found: C, 58.82; H, 6.24; N, 8.87.

EXAMPLE 60

4-(3,4-Difluorophenyl)-1,6-dimethyl-3-carbomethoxy-2-oxo-1,2,3,4-tetrahydro-pyrimidine-5-carboxylic acid {3-[4-(4-fluorophenyl)-piperidine-1-yl]-propyl}amide Hydrochloride

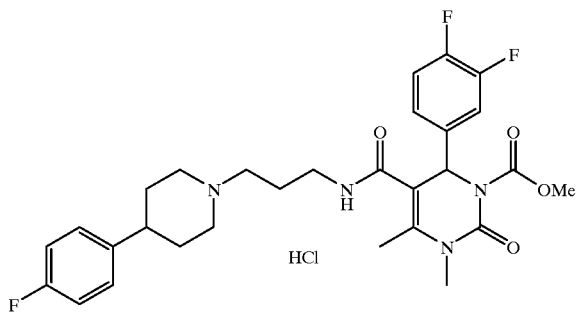

4-(3,4-Difluorophenyl)-1,6-dimethyl-3-carbomethoxy-2-oxo-1,2,3,4-tetrahydro-pyrimidine-5-carboxylic acid is coupled to 1-(3-aminopropyl)-4-(4-fluorophenyl)-piperidine dihydrochloride under EDC/HOAt conditions similar to those described earlier to provide as a white solid, after hydrochloride preparation with 1N HCl.

Analysis: Calcd. for $C_{29}H_{34}F_3N_4O_4Cl$.0.85 $H_2O$; C, 57.06; H, 5.90; N, 9.18; Found: C, 57.10; H, 6.21; N, 8.98.

EXAMPLE 61

(−)-4-(3,4-Difluorophenyl)-3,6-dimethyl-2-oxo-1,2,3,4-tetrahydro-pyrimidine-5-carboxylic acid {3-[4-(2-cyano-4-fluorophenyl)-piperidin-1-yl]-propyl}-amide

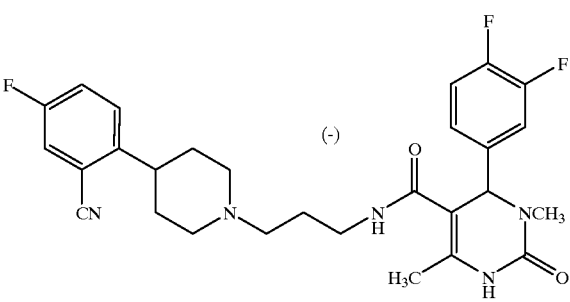

2-[1-(3-Amino-propyl)-piperidin-4yl]-5-fluoro-benzonitrile dihydrochloride (85.0 mg, 0.254 mmol), triethylamine (108 µl, 0.774 mmol), (−)-4-(3,4-difluorophenyl)-3,6-dimethyl-2-oxo-1,2,3,4-tetrahydro-pyrimidine-5-carboxylic acid (75.0 mg, 0.266 mmol), 1-ethyl-3-(3-dimethylaminopropyl)-carbodiimide Hydrochloride (50.9 mg, 0.266 mmol), and 1-hydroxybenzotriazole hydrate (35.9 mg, 0.266 mmol) were combined in dimethylformamide (5 ml) and stirred 24 hr at room temperature After removal of the solvent in vacuo, the residue was treated with saturated sodium bicarbonate (aq.) and extracted with ethyl acetate (3X). The extracts were combined, washed with brine, dried over magnesium sulfate, filtered and concentrated in vacuo to give a crude oil (140 mg). Flash chromatography on silica gel (133/10/1 of methylene chloride/methanol/conc. ammonium hydroxide) gave the product as a white solid from ether ($[\alpha_D]$=−78.4°, c=0.125 MeOH).

Analysis: Calcd. for $C_{28}H_{30}F_3N_5O_2$. 0.3$OH_2O$; C, 63.33; H, 5.81; N, 13.19; Found: C, 63.03; H, 5.76; N, 13.36.

The following seven Examples were prepared using the procedure for the immediately preceding Example above with the noted reagent replacements.

EXAMPLE 62

(−)-4-(3,4-Difluorophenyl)-3,6dimethyl-2-oxo-1,2,3,4-tetrahydro-pyrimidine-5-carboxylic acid {3-[4-cyano-4-(4-fluorophenyl)-pipenidin-1-yl]-propyl}-amide.

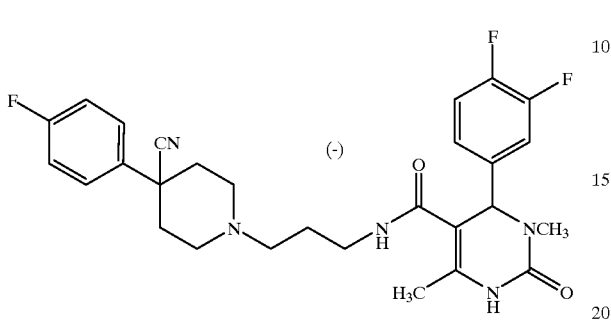

1-(3-Amino-propyl)-4-(4-fluorophenyl)-piperidine-4-carbonitrile dihydrochloride was used in place of 2-[1-(3-anmino-propyl)-piperidine-4-yl]-5-fluoro-benzonitrile dihydrochloride ($[\alpha_D]$=−72°, c=0.145 MeOH).

Analysis: Calcd. for $C_{28}H_{30}F_3N_5O_2$; C, 64.16; H, 5.84; N, 13.17; Found: C, 63.99; H, 5.88; N, 13.33.

EXAMPLE 63

(−)-4-(3,4-Difluorophenyl)-3,6-dimethyl-2-oxo-1,2,3,4-tetrahydro-pyrinidine-5-carboxylic acid {3-[4-cyano-4-(2,4-difluorophenyl)-piperidin-1-yl]-propyl}-amide Hydrochloride

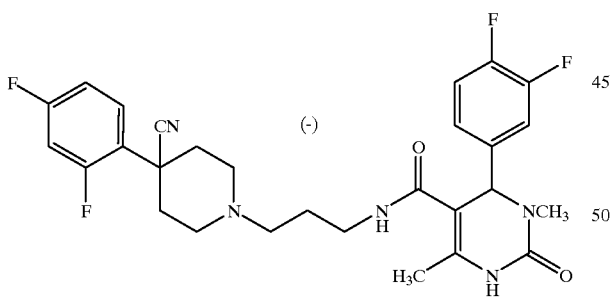

1-(3-Amino-propyl)-4-(2,4-difluorophenyl)-piperidine-4-carbonitrile dihydrochloride was used in place of 2-[1-(3-amino-propyl)-piperidine-4-yl]-5-fluoro-benzonitrile dihydrochloride. The hydrochloride salt was prepared from ethyl acetate/ether with 1N hydrochloric acid in ether ($[\alpha_D]$=−38.4°, c=0.185 MeOH).

Analysis: Calcd. for $C_{28}H_{29}F_4N_5O_2 \cdot HCl \cdot 0.55H_2O \cdot 0.20C_4H10O$; C, 57.19; H, 5.52; N, 11.58; Found: C, 56.94; H, 5.80; N, 11.34.

EXAMPLE 64

(−)-4(3,4-Difluorophenyl)-3,6dimethyl-2-oxo-1,2,3,4-tetrahydro-pyrimidine-5-carboxylic acid t3-[4-(4-fluorophenyl)-piperidin-1-yl]-propyl}-amide.

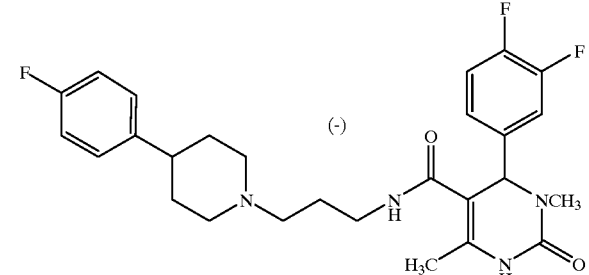

3-[4-(4-fluorophenyl)-piperidin-1-yl]-propylamine dihydrochloride was used in place of 2-[1-(3-amino-propyl)-piperidine-4-yl]-5-fluoro-benzonitrile dihydrochloride ($[\alpha_D]$=−82.2°, c=0.135 MeOH).

Analysis: Calcd. for $C_{27}H_{31}F_3N_4O_2 \cdot 0.35H_2O$; C, 63.97; H, 6.30; N, 11.01; Found: C, 63.78; H, 6.21; N, 11.18.

EXAMPLE 65

(−)-4-(3,4-Difluorophenyl)-1,6-dimethyl-2-oxo-1,2,3,4tetrahydro-pyrimidine-5-carboxylic acid {3-[4-(2-cyano-4-fluorophenyl)-piperidin-1-yl]-propyl}-amide.

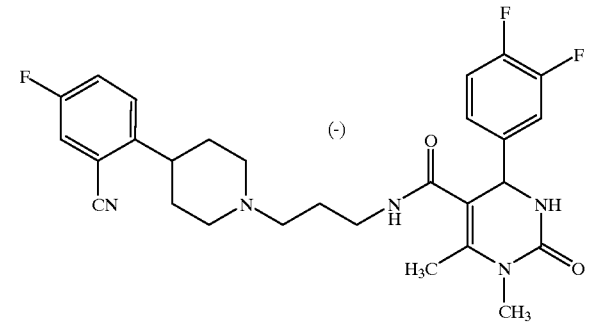

(+)-4-(3,4-Difluorophenyl)-1,6-dimethyl-2-oxo-1,2,3,4-tetrahydro-pyrimidine-5-carboxylic acid was used in place of (−)-4-(3,4-Difluorophenyl)-3,6-dimethyl-2-oxo-1,2,3,4-tetrahydro-pyrimidine-5-carboxylic acid ($[\alpha_D]$=−62.4°, c=0.165 MeOH).

Analysis: Calcd. for $C_{28}H_{30}F_3N_5O_2 \cdot 0.05H_2O$; C, 63.87; H, 5.76; N, 13.30; Found: C, 63.56; H, 5.46; N, 13.26.

EXAMPLE 66

(+)-4-(3,4-Difluorophenyl)-1,3,6-trimethyl-2-oxo-1,2,3,4-tetrahydro-pyrimidine-5-carboxylic acid {3-[4-(2-cyano-4-fluorophenyl)-piperidin-1-yl]-propyl}-amnide

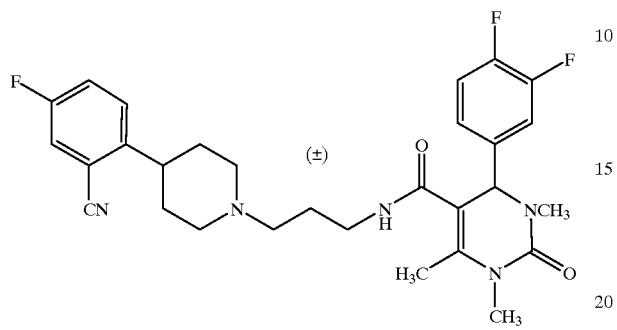

(+)-4-(3,4-Difluorophenyl)-1,3,6-trimethyl-2-oxo-1,2,3,4-tetrahydro-pyrimidine-5-carboxylic acid was used in place of (−)-4-(3,4-Difluorophenyl)-3,6-dimethyl-2-oxo-1,2,3,4-tetrahydro-pyrimidine-5-carboxylic acid.

Analysis: Calcd. for $C_{29}H_{32}F_3N_5O_2$; C, 64.55; H, 5.98; N, 12.98; Found: C, 64.33; H, 6.00; N, 12.98.

EXAMPLE 67

(−)-4-(3,4-Difluorophenyl)-1,3,6-trimethyl-2-oxo-1,2,3,4-tetrahydro-pyrimidine-5-carboxylic acid {3-[4-(2-cyano-4-fluorophenyl)-piperidin-1-yl]-propyl}-amide

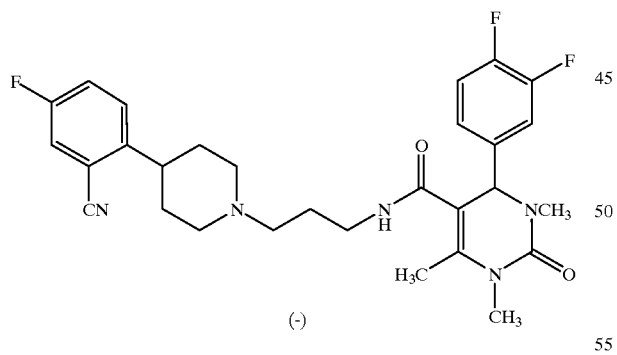

4-(3,4-Difluorophenyl)-1,3,6-trimethyl-2-oxo-1,2,3,4-tetrahydro-pyrimnidine-5-carboxylic acid {3-[4-(2-cyano-4-fluorophenyl)-piperidin-1-yl]-propyl}-amide was resolved via chiral HPLC to give the individual (−) and (+) enantiomers $[\alpha_D]=-33.8°$, c=0.145, MeOH; Analysis: Calcd. for $C_{29}H_{32}F_3N_5O_2 \cdot 0.5\ H_2O \cdot 0.2\ C_4H_{10}O$; C, 59.66; H, 6.05; N, 11.68; Found: C, 59.39; H, 6.15; N, 11.46.

EXAMPLE 68

(+)-4-(3,4-Difluorophenyl)-1,3,6-trimethyl-2-oxo-1,2,3,4-tetrahydro-pyrimidine-5-carboxylic acid {3-[4-(2-cyano-4-fluorophenyl)-piperidin-1-yl]-propyl}-amide

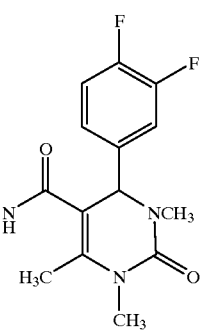

$[\alpha_D]=+34.8°$, c=0.11, MeOH; Analysis: Calcd. for $C_{29}H_{32}F_3N_5O_2 \cdot HCl \cdot 0.45\ H_2O \cdot 0.2\ C_4H_{10}O$; C, 59.75; H, 6.04; N, 11.69; Found: C, 59.45; H, 6.18; N, 11.40.

EXAMPLE 69

(R)-4-(3,4-Difluorophenyl)-6-methoxymethyl-2-oxo-1,2,3,4-tetrahydro-pyrimidine-5-carboxylic acid {3-[4-cyano-4-(4-fluorophenyl)-piperidin-1-yl]-propyl}-amide

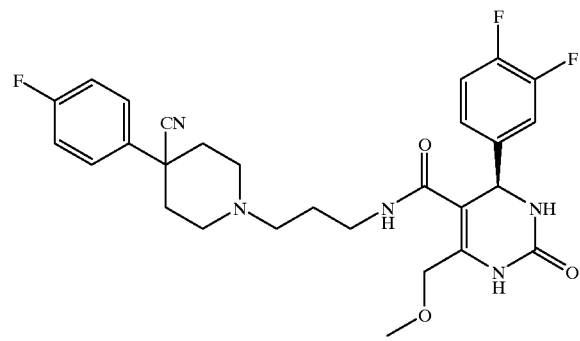

Analysis: Calcd. for $C_{28}H_{30}F_3N_5O_3$; C, 62.10; H, 5.58; N, 12.93; Found: C, 62.02; H, 5.49; N, 13.08.

EXAMPLE 70

(R)-4-(3,4-Difluorophenyl)-6-methoxymethyl-2-oxo-1,2,3,4-tetrahydro-pyrimidine-5-carboxylic acid {3-[4-cyano-4-(2,4-difluorophenyl)-piperidin-1-yl]-propyl}-amnide.

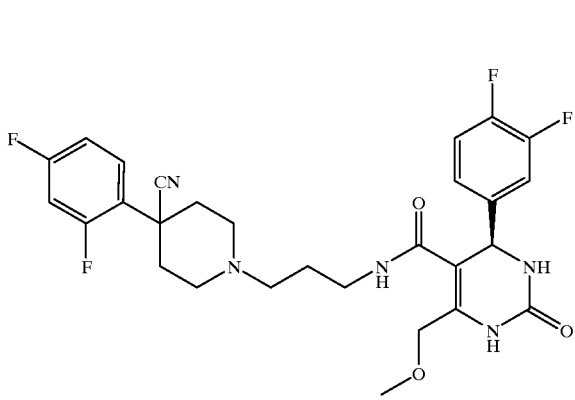

Analysis: Calcd. for $C_{28}H_{29}F_4N_5O_3$; C, 60.10; H, 5.22; N, 12.52; Found: C, 60.14; H, 5.05; N, 12.85.

EXAMPLE 71

(R)-4-(3,4-Difluorophenyl)-6-methoxymethyl-1-methyl-2-oxo-1,2,3,4-tetrahydro-pyrimidine-5-carboxylic acid {3-[4-cyano-4-(4-fluorophenyl)-piperidin-1-yl]-propyl}-amide

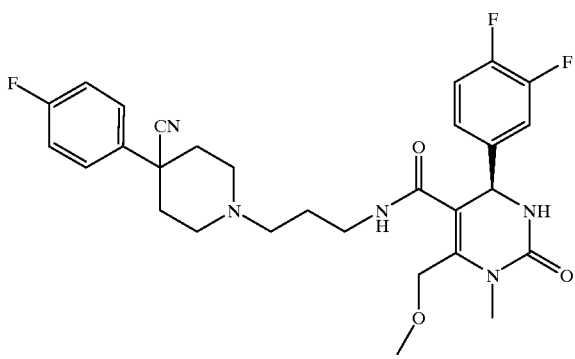

Analysis: Calcd. for $C_{29}H_{32}F_3N_5O_3$; C, 62.69; H, 5.81; N, 12.61; Found: C, 62.45; H, 6.01; N, 12.76.

EXAMPLE 72

4-(3,4-Difluorophenyl)-6-methoxymethyl-1-methyl-2-oxo-1,2,3,4-tetrahydro-pyrimidine-5-carboxylic acid {3-[4-(4-fluorophenyl)-piperidin-1-yl]-propyl}-amide

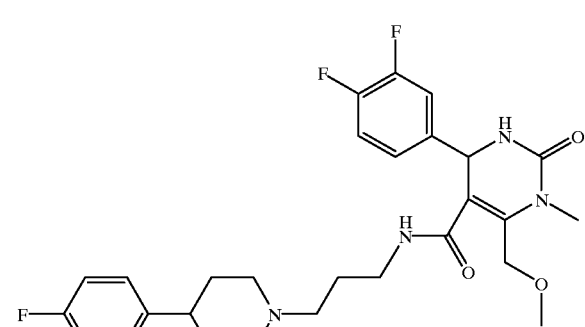

To a suspension of sodium hydride, 60% dispersion in mineral oil (0.233 mmol, 9 mg) in 2 ml DMF was added 4-(3,4-Difluorophenyl)-6-methoxymethyl-2-oxo-1,2,3,4-tetrahydro-pyrimidine-5-carboxylic acid {3-[4-(4-fluorophenyl)-piperidin-1-yl]-propyl}-amide (0.194 mmol, 100 mg) in 1 mL DMF. This was stirred under argon for 15 min, then iodomethane (0.194 mmol, 12 mL) was added. The suspension was stirred for 1 h, poured onto saturated sodium bicarbonate, and extracted with ethyl acetate. The combined organic layers were washed with saturated sodium chloride, dried with magnesium sulfate, and concentrated in vacuo. The crude material was passed through silica (3–5–10% methanol, dichloromethane) to give the product.

Analysis: Calcd. for $C_{28}H_{33}F_3N_4O_3 \cdot 0.75\ H_2O$; C, 61.80; H, 6.39; N, 10.30; Found: C, 61.83; H, 5.90; N, 10.57.

EXAMPLE 73

As a specific embodiment of an oral composition, 100 mg of the compound of Example 32 is formulated with sufficient finely divided lactose to provide a total amount of 580 to 590 mg to fill a size O hard gel capsule.

EXAMPLE 74

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values $\leq$50 nM.

EXAMPLE 75

Selective Binding Assays

Membranes prepared from stably transfected human alpha id and alpha 1b cell lines (ATCC CRL 11138 and CRL 11139, respectively) were used to identify compounds that selectively bind to the human alpha 1a adrenergic receptor. These competition binding reactions (total volume=200 μl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

All of the compounds prepared in Examples 21–72 were found to have alpha 1a Ki values of less than 30 nM as determined via the screening assay described in Example 74. These compounds were further found to be at least 10 fold more selective in binding to alpha 1a receptors versus binding to the alpha 1b and alpha 1d receptors, as determined by the selective binding assay described in the preceding paragraphs. Except for the (+) enantiomers of Examples 57 and 58 and the compounds of Examples 45, 59, 60, 64 and 68, the compounds were found to have a Ki of less than 5 nM and to exhibit at least 50-fold selectivity for 1a over 1b and 1d.

EXAMPLE 76

EXEMPLARY COUNTERSCREENS

1. Assay Title: Dopamine D2, D3, D4 In Vitro Screen
   Objective of the Assay:
   The objective of this assay is to eliminate agents which specifically affect binding of [3H] spiperone to cells expressing human dopamine receptors D2, D3 or D4.
   Method:
   Modified from VanTol et al (1991); *Nature* (Vol 350) Pg 610–613.
   Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 μg membranes in a total volume of 500 μl containing 0.2 nM [3H]-spiperone. Non-specific binding is defined using 10 μM apomorphine. The assay is terminated after a 2 hour incubation at room temperature by rapid filtration over GF/B filters presoaked in 0.3% PEI, using 50 mM Tris-HCl pH 7.4.
2. Assay Title: Serotonin 5HT1a
   Objective of the Assay
   The objective of this assay is to eliminate agents which specifically affect binding to cloned human 5HT1a receptor
   Method:
   Modified from Schelegel and Peroutka *Biochemical Pharcology* 35: 1943–1949 (1986).
   Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1mglml ascorbate. Non-specific binding is defined using 10 μM propranolol. The assay is terminated after a 1 hour incubation at room temperature by rapid filtration over GF/Cfilters

EXAMPLE 77

EXEMPLARY FUNCTIONAL ASSAYS

In order to confirm the specificity of compounds for the human alpha 1a adrenergic receptor and to define the biological activity of the compounds, the following functional tests may be performed:

1. In vitro Rat, Dog and Human Prostate and Dog Urethra
Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 68 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; CaCl$_2$, 2.5 mM; KH$_2$PO$_4$, 1.2 mM; MgSO$_4$, 1.2 mM; NaHCO$_3$, 2.0 mM; dextrose, 11 mM]warmed to 37° C. Excess lipid material and connective tissue are carefully removed. Tissue segments are attached to glass tissue holders. with 4-0 surgical silk and placed in a 5 ml jacketed tissue bath containing Krebs buffer at 37° C., bubbled with 5% CO$_2$/95% O$_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 μM (for rat), 10 μM (for dog) and 20 μM (for human) of phenylephrine, a cumulative concentration response curve to an agonist is generated; the tissues are washed every minutes for one hour. Vehicle or antagonist is added to the bath and allowed to incubate for one hour, then another cumulative concentration response curve to the agonist is generated.

EC$_{50}$ values are calculated for each group using GraphPad Inplot software. pA$_2$ (-log Kb) values were obtained from Schild plot when three or more concentrations were tested. When less than three concentrations of antagonist are tested, Kb values are calculated according to the following formula $K_b = [B] x - 1$ where x is the ratio of EC$_{50}$ of agonist in the presence and absence of antagonist and [B] is the antagonist concentration.

2. Measurement of Intra-Urethral Pressure in Anesthetized Does
PURPOSE: Benign prostatic hyperplasia causes a decreased urine flow rate that may be produced by both passive physical obstruction of the prostatic urethra from increased prostate mass as wel as active obstruction due to prostatic contraction. Alpha adrenergic receptor antagonists such as prazosin and terazosin prevent active prostatic contraction, thus improve uine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephline without any activity at the vasculature.

While the foregoing specification teaches the principles of the present invention, with examples provided for the purpose of illustration, the practice of the invention encompasses all of the usual variations, adaptations and/or modifications as come within the scope of the following claims and their equivalents.

What is claimed is:

1. A compound of formula:

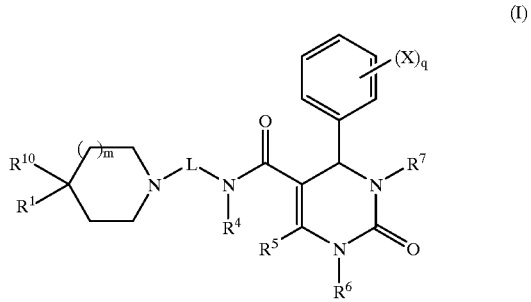

(I)

wherein $R^1$ is selected from phenyl, substituted phenyl, pyridyl, and substituted pyridyl, wherein the substituents on the phenyl or the pyridyl are independently selected from F, Cl, Br, I, $(CH_2)_{0-4}CF_3$, CN, $NO_2$, $R^a$, and $OR^a$;

$R^{10}$ is selected from H, OH, CN, $R^b$, $OR^b$, $(CH_2)_{1-4}OR^b$ and $(CH_2)_{0-4}CF_3$;

m is an integer of from 0 to 2;

L is selected from $(CH_2)_k$, $(CHR^2)_k$, $CR^8R^9(CH_2)_{k-1}$, $(CH_2)_{k-1}CR^8R^9$, $CH_2CR^8R^9CH_2$, $CH_2CH_2CR^8R^9CH_2$, and $CH_2CR^8R^9CH_2CH_2$;

$R^2$ is selected from $R^c$ and $(CH_2)_{0-4}CF_3$;

k is an integer of from 2 to 4;

$R^4$ is selected from H, $R^d$ and $(CH_2)_{0-4}CF_3$;

$R^5$ is selected from H, $R^e$, $(CH_2)_{1-4}OR^e$, and $(CH_2)_{1-4}CF_3$;

$R^6$ is selected from H and $R^f$;

$R^7$ is selected from H, $R^g$, $(CH_2)_{1-4}OR^g$, and $(CH_2)_{0-4}CF_3$;

$R^8$ and $R^9$ are each independently selected from $R^c$ and $(CH_2)_{0-4}CF_3$;

each X is independently selected from F, Cl, Br, I, CN and $R^h$;

$R^a$, $R^d$, $R^e$, $R^f$, $R^g$ and $R^h$ are each independently selected from $C_1$ to $C_6$ alkyl;

$R^b$ and $R^c$ are independently selected from $C_1$ to $C_6$ alkyl and $C_3$ to $C_7$ cyclic alkyl;

and q is an integer of from 0 to 4;

or a pharmaceutically acceptable salt thereof.

2. The compound according to claim 1, wherein $R^1$ is selected from phenyl, mono-, di- or tri-substituted phenyl, pyridyl, and mono-, di-, or tri-substituted pyridyl, wherein the substituents on the phenyl or the pyridyl are independently selected from F, Cl, Br, I, CN and $R^a$;

$R^{10}$ is selected from H, OH, CN, $R^b$ and $OR^b$;

$R^2$ is selected from H and $R^c$;

$R^4$ is selected from H and $R^d$;

$R^5$ is selected from H, $R^e$ and $(CH_2)_{1-4}OR^e$;

$R^7$ is selected from H, $R^g$, and $(CH_2)_{1-4}OR^g$;

$R^8$ and $R^9$ are each $R^c$;

$R^a$, $R^b$, $R^c$, $R^d$, $R^e$, $R^f$, $R^g$ and $R^h$ are each independently selected from $C_1$ to $C_4$ alkyl;

and q is an integer of from 0 to 3;

or a pharmaceutically acceptable salt thereof.

3. The compound according to claim 2, wherein $R^7$ is selected from H and $R^g$; or a pharmaceutically acceptable salt thereof.

4. The compound according to claim 2, wherein $R^1$ is selected from phenyl, mono-, di- or tri-substituted phenyl and pyridyl, wherein the substituents on the phenyl are independently selected from F, Cl, Br, I, CN and $R^a$; or a pharmaceutically acceptable salt thereof.

5. The compound according to claim 2, wherein $R^1$ is selected from phenyl, mono-, di- or tri-substituted phenyl and pyridyl, wherein the substituents on the phenyl are independently selected from F, CN and $R^a$; or a pharmaceutically acceptable salt thereof.

6. The compound according to claim 2, wherein $R^1$ is selected from phenyl, mono-, di- or tri-substituted phenyl and pyridyl, wherein the substituents on the phenyl are independently selected from F, CN and $R^a$;

m is an integer from 0 to 1;
L is selected from, $(CH_2)_k$, $(CHR^2)_k$, $CR^8R^9(CH_2)_{k-1}$, $(CH_2)_{k-1}CR^8R^9$, and $CH_2CR^8R^9CH_2$;
k is 2 or 3; and
each X is independently selected from F, CN and $R^h$; or a pharmaceutically acceptable salt thereof.

7. The compound according to claim 1, wherein $R^1$ is selected from phenyl, mono-, di- or tri-substituted phenyl, pyridyl, and mono-, di-, or tri-substituted pyridyl, wherein the substituents on the phenyl or the pyridyl are independently selected from F, Cl, Br, I, CN, $CF_3$ and $R^a$;

$R^{10}$ is selected from H, OH, CN, $R^b$ and $OR^b$;
m is 1;
$R^2$ is $R^c$;
$R^4$ is H;
$R^5$ is selected from H, $R^e$, and $(CH_2)_{1-4}OR^e$;
$R^6$ is selected from H and $R^f$;
$R^7$ is selected from H, $R^g$, and $(CH_2)_{1-4}OR^g$;
$R^8$ and $R^9$ are each independently $R^c$;
$R^a$, $R^c$, $R^e$, $R^f$, $R^g$ and $R^h$ are each independently selected from $C_1$ to $C_4$ alkyl;
$R^b$ is selected from $C_1$ to $C_6$ alkyl and $C_3$ to $C_7$ cyclic alkyl;
and q is an integer of from 0 to 3;

or a pharmaceutically acceptable salt thereof.

8. The compound according to claim 7, wherein $R^1$ is selected from phenyl, mono-, di- or tri-substituted phenyl and pyridyl, wherein the substituents on the phenyl are independently selected from F, Cl, Br, I, CN, $CF_3$ and $R^a$; and $R^5$ is selected from H and $R^e$; or a pharmaceutically acceptable salt thereof.

9. A compound of formula:

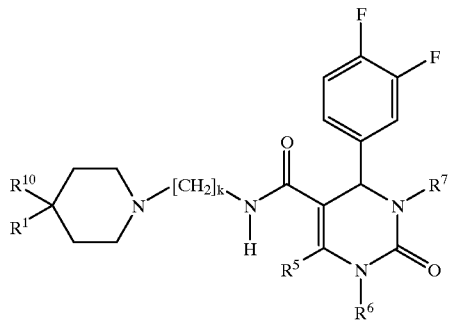

(III)

wherein $R^1$ is

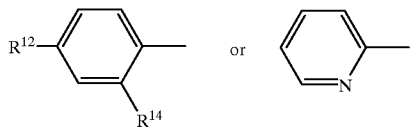

wherein $R^{12}$ and $R^{14}$ are each independently selected from H, F, Cl, Br, I, CN, $CF_3$ and $C_1$ to $C_4$ alkyl;
$R^{10}$ is selected from H, OH, and $R^b$;
k is an integer of from 2 to 4;
$R^5$ is selected from H, $R^e$ and $(CH_2)_{1-4}OR^e$;
$R^6$ is selected from H, methyl and ethyl;
$R^7$ is selected from H, $R^g$, and $(CH_2)_qOR^g$; and
$R^b$, $R^e$ and $R^g$ are each independently selected from $C_1$ to $C_4$ alkyl;

or a pharmaceutically acceptable salt thereof.

10. The compound according to claim 9, wherein $R^{12}$ and $R^{14}$ are each independently selected from H, F, CN and $C_1$ to $C_4$ alkyl;
k is an integer of from 2 to 3;
$R^5$ is selected from H, methyl, ethyl, and $CH_2OCH_3$; and
$R^7$ is selected from H, methyl, and ethyl;

or a pharmaceutically acceptable salt thereof.

11. The compound according to claim 10, wherein $R^7$ is selected from H and methyl; or a pharmaceutically acceptable salt thereof.

12. The compound according to claim 9 selected from the group consisting of:
(4R)-4-(3,4-Difluorophenyl)-6-methoxymethyl-2-oxo-1,2,3,4-tetrahydro-pyrimidine-5-carboxylic acid {3-[4-(2-cyano-4-fluorophenyl)-piperidin-1-yl]-propyl}-amide;
(4R)-4-(3,4-Difluorophenyl)-6-methyl-2-oxo-1,2,3,4-tetrahydro-pyrimidine-5-carboxylic acid {3-[4-(2-cyano-4-fluorophenyl)-piperidin-1-yl]-propyl}-amide;
(4R)-4-(3,4-Difluorophenyl)-6-methoxymethyl-2-oxo-1,2,3,4-tetrahydro-pyrimidine-5-carboxylic acid {3-[4-(2-cyanophenyl)-piperidin-1-yl]-propyl}-amide;
(4R)-4-(3,4-Difluorophenyl)-6-methyl-2-oxo-1,2,3,4-tetrahydro-pyrimidine-5-carboxylic acid {3-[4-(2-cyanophenyl)-piperidin-1-yl]-propyl}-amide;
(4R)4-(3,4-Difluorophenyl)-6-methoxymethyl-2-oxo-1,2,3,4-tetrahydro-pyrirnidine-5-carboxylic acid {3-[4-(4-fluorophenyl)-4-hydroxy-piperidin-1-yl]-propyl}-amide;

(4R)-4-(3,4-Difluorophenyl)-6-methyl-2-oxo-1,2,3,4-tetrahydro-pyrimidine-5-carboxylic acid {3-[4-(4-fluorophenyl)-4-hydroxy-piperidin-1-yl]-propyl}-amide;

(4R)-4-(3,4-Difluorophenyl)-6-methoxymethyl-2-oxo-1,2,3,4-tetrahydro-pyrimidine-5-carboxylic acid [3-(3',4',5',6'-tetrahydro-2'H-[2,4']bipyridinyl-1'-yl)-propyl]-amide;

(4R)-4-(3,4-Difluorophenyl)-6-methyl-2-oxo-1,2,3,4-tetrahydro-pyrimidine-5-carboxylic acid [3-(3',4',5',6'-tetrahydro-2'H-[2,4']bipyridinyl-1'-yl)-propyl]-amide;

(−)-4-(3,4-Difluorophenyl)-2-oxo-1,2,3,4-tetrahydro-pyrimidine-5-carboxylic acid {3-[4-(2-cyanophenyl)-piperidin-1-yl]-propyl}-amide; and (−)-4-(3,4-Difluorophenyl)-2-oxo-1,2,3,4-tetrahydro-pyrimidine-5-carboxylic acid {3-[4-(4-fluorophenyl)-piperidin-1-yl]-propyl}-amide;

and pharmaceutically acceptable salts thereof.

13. The compound according to claim 9 selected from the group consisting of:

(−)-4-(3,4-Difluorophenyl)-6-methyl-2-oxo-1,2,3,4-tetrahydro-pyrimidine-5-carboxylic acid [3-[4-(4-fluorophenyl)-piperidin-1-yl]-propyl]-amide;

(−)-4-(3,4-Difluorophenyl)-6-methoxymethyl-2-oxo-1,2,3,4-tetrahydro-pyrimidine-5-carboxylic acid {3-[4-(4-fluorophenyl)-piperidin-1-yl]-propyl}-amide;

(−)-4-(3,4-Difluorophenyl)-2-oxo-1,2,3,4-tetrahydro-pyrimidine-5-carboxylic acid {3-[4-(4-fluorophenyl)-4-hydroxy-piperidin-1-yl]-propyl}-amide;

(−)-4-(3,4-Difluorophenyl)-2-oxo-1,2,3,4-tetrahydro-pyrimidine-5-carboxylic acid {3-[4-(2-cyano-4-fluorophenyl)-piperidin-1-yl]-propyl}-amide;

(−)-4-(3,4-Difluorophenyl)-2-oxo-1,2,3,4-tetrahydro-pyrimidine-5-carboxylic acid [3-(3',4',5',6'-tetrahydro-2'H-[2,4']bipyridinyl-1'-yl)-propyl]-amide;

(−)-4-(3,4-Difluorophenyl)-2-oxo-1,2,3,4-tetrahydro-pyrimidine-5-carboxylic acid {3-[4-cyano-4-(fluorophenyl)-piperidin-1-yl]-propyl}-amide;

(−)-4-(3,4-Difluorophenyl)-6-methyl-2-oxo-1,2,3,4-tetrahydro-pyrimidine-5-carboxylic acid {3-[4-cyano-4-(4-fluorophenyl)-piperidin-1-yl]-propyl}-amide;

(−)-4-(3,4-Difluorophenyl)-2-oxo-1,2,3,4-tetrahydropyrimidine-5-carboxylic acid {3-[4-cyano-4-(2-cyanophenyl)-piperidin-1-yl]-propyl}-amide;

4-(3,4-Difluorophenyl)-6-methyl-2-oxo-1,2,3,4-tetrahydropyirimdine-5-carboxylic acid {3-[4-cyano-4-(2-cyanophenyl)-piperidin-1-yl]-propyl}-amide; and 4-(3,4-Difluorophenyl)-1-methyl-2-oxo-1,2,3,4-tetrahydropyiimidine-5-carboxylic acid {3-[4-cyano-4-(2,4-difluorophenyl)-piperidin-1-yl]-propyl}-amide;

and pharmaceutically acceptable salts thereof.

14. The compound according to claim 9 selected from the group consisting of:

(+)-4-(3,4-Difluorophenyl)-1-methyl-2-oxo-1,2,3,4-tetrabydro-pyrimidine-5-carboxylic acid {3-[4-cyano-4-(4-fluorophenyl)-piperidin-1-yl]-propyl}-amide;

4-(3,4-Difluorophenyl)-1-methyl-2-oxo-1,2,3,4-tetrahydropyrimidine-5-carboxylic acid {3-[4-(4-fluorophenyl)-piperidin-1-yl]-propyl}-amide;

4-(3,4-Difluorophenyl)-1,3-dimethyl-2-oxo-1,2,3,4-tetrahydro-pyrirnidine-5-carboxylic acid {3-[4-cyano-4-(4-fluorophenyl)-piperidin-1-yl]-propyl}-amide;

4-(3,4-Difluorophenyl)-1,3-dimethyl-2-oxo-1,2,3,4-tetrahydro-pyrimidine-5-carboxylic acid {3-[4-(2-cyano-4-fluorophenyl)-piperidin-1-yl]-propyl}-amide;

4-(3,4-Difluorophenyl)-1,3-dimethyl-2-oxo-1,2,3,4-tetrahydro-pyrimidine-5-carboxylic acid {3-[4-(4-fluorophenyl)-piperidin-1-yl]-propyl}-amide;

4-(3,4-Difluorophenyl)-1,3-dimethyl-2-oxo-1,2,3,4-tetrahydro-pyrimidine-5-carboxylic acid {3-[4-cyano-4-(2,4-difluoropbenyl)-piperidin-1-yl]-propyl}-amide;

4-(3,4-Difluorophenyl)-1-methyl-2-oxo-1,2,3,4-tetrahydro-pyrimidine-5-carboxylic acid {3-[4-(4-fluorophenyl)-4-hydroxy-piperidin-1-yl]-propyl}-amide;

4-(3,4-Difluorophenyl)-1-methyl-2-oxo-1,2,3,4-tetrahydro-pyrimidine-5-carboxylic acid {3-[4-(2-cyano-4-fluorophenyl)-piperidin-1-yl]-propyl}-amide;

(−)-4-(3,4-Difluorophenyl)-1-methyl-2-oxo-1,2,3,4-tetrahydro-pyrimidine-5-carboxylic acid {3-[4-cyano-4-(4-fluorophenyl)-piperidin-1-yl]-propyl}-amide; and 4-(3,4-Difluorophenyl)-1-methyl-2-oxo-1,2,3,4-tetrahydro-pyrimidine-5-carboxylic acid {3-[2-cyano-4-fluorophenyl)-4-cyano-piperidin-1-yl]-propyl}-amine;

and pharmaceutically acceptable salts thereof.

15. The compound according to claim 9 selected from the group consisting of:

4-(3,4-Difluorophenyl)-1,3-dimethyl-2-oxo-1,2,3,4-tetrabydro-pyrimdine-5-carboxylic acid {3-[2-cyano-4-fluorophenyl)-4-cyanopiperidin-1-yl]-propyl}amine;

4-(3,4-Difluorophenyl)-1,6-dimethyl-2-oxo-1,2,3,4-tetrahydro-pyrimidine-5-carboxylic acid {3-[2-cyano-4-fluorophenyl)-piperidin-1-yl]-propyl}amine;

4-(3,4-Difluorophenyl)-1,6-dimethyl-2-oxo-1,2,3,4-tetrahydro-pyrimidine-5-carboxylic acid {3-[4-(4-fluorophenyl)-piperidine-1-yl]-propyl}-amide;

(4R)-4-(3,4-Difluorophenyl)-1,6-dimethyl-2-oxo-1,2,3,4-tetrahydro-pyrirnidine-5-carboxylic acid {3-[4-(4-fluorophenyl)-4-cyano-piperidine-1-yl]-propyl}-amide;

(4R)-4-(3,4-Difluorophenyl)-1,6-dimethyl-2-oxo-1,2,3,4-tetrabydro-pyrimidine-5-carboxylic acid {3-[4-(2,4-difluorophenyl)-4-cyano-piperidine-1-yl]-propyl}-amide;

4-(3,4-Difluorophenyl)-1,3,6-trimethyl-2-oxo-1,2,3,4-tetrahydro-pyrimidine-5-carboxylic acid-{3-[4-(4-fluorophenyl)-piperidin-1-yl]-propyl}-amide;

(4R)-4-(3,4-Difluorophenyl)-1,3,6-trimethyl-2-oxo-1,2,3,4-tetrahydro-pyrimidine-5-carboxylic acid {3-[4-(4-fluorophenyl)-4-cyano-piperidin-1-yl]-propyl}-amide;

(4R)-4-(3,4-Difluorophenyl)-1,3,6-trimethyl-2-oxo-1,2,3,4-tetrahydro-pyirnidine-5-carboxylic acid {3-[4-(2,4-difluorophenyl)-4cyano-piperidine-1-yl]-propyl}-amide;

(−)-4-(3,4-Difluorophenyl)-3,6-dimethyl-2-oxo-1,2,3,4-tetrahydro-pyrimidine-5-carboxylic acid {3-[4-(2-cyano-4-fluorophenyl)-piperidin-1-yl]-propyl}-amide; and (−)-4-(3,4-Difluorophenyl)-3,6-dimethyl-2-oxo-1,2,3,4-tetrahydro-pyrimidine-5-carboxylic acid {3-[4-cyano-4-(4-fluorophenyl)-piperidin-1-yl]-propyl}-amide;

and pharmaceutically acceptable salts thereof.

16. The compound according to claim 9 selected from the group consisting of:

(−)-4-(3,4-Difluorophenyl)-3,6-dimethyl-2-oxo-1,2,3,4-tetrahydro-pyrimidine-5-carboxylic acid {3-[4-cyano-4-(2,4-difluorophenyl)-piperidin-1-yl]-propyl}-amide;

(−)-4-(3,4-Difluorophenyl)-3,6-dimethyl-2-oxo-1,2,3,4-tetrahydro-pyirnidine-5-carboxylic acid {3-[4-(4-fluorophenyl)-piperidin-1-yl]-propyl}-amide;

(−)-4-(3,4-Difluorophenyl)-1,6-dimethyl-2-oxo-1,2,3,4-tetrahydro-pyrimidine-5-carboxylic acid {3-[4-(2-cyano-4-fluorophenyl)-piperidin-1-yl]-propyl}-amide;

(+)-4-(3,4-Difluorophenyl)-1,3,6-trimethyl-2-oxo-1,2,3,4-tetrahydro-pyrimidine-5-carboxylic acid {3-[4-(2-cyano-4-fluorophenyl)-piperidin-1-yl]-propyl}-amide;

(−)-4-(3,4-Difluorophenyl)-1,3,6-trimethyl-2-oxo-1,2,3,4-tetrahydro-pyrimidine-5-carboxylic acid {3-[4-(2-cyano-4-fluorophenyl)-piperidin-1-yl]-propyl}-amide;

(+)-4-(3,4-Difluorophenyl)-1,3,6-trimethyl-2-oxo-1,2,3,4-tetrahydro-pyrimidine-5-carboxylic acid {3-[4-(2-cyano-4-fluorophenyl)-piperidin-1-yl]-propyl}-amide;

(4R)-4-(3,4-Difluoropbenyl)-6-methoxymethyl-2-oxo-1,2,3,4-tetrahydro-pyriimidine-5-carboxylic acid {3-[4-cyano-4-(4-fluorophenyl)-piperidin-1-yl]-propyl}-amide;

(4R)-4-(3,4-Difluorophenyl)-6-methoxymethyl-2-oxo-1,2,3,4-tetrahydro-pyrnidine-5-carboxylic acid {3-[4-cyano-4-(2,4-difluorophenyl)-piperidin-1-yl]-propyl}-amide;

(4R)-4-(3,4-Difluorophenyl)-6-methoxymethyl-1-methyl-2-oxo-1,2,3,4-tetrahydro-pyrimidine-5-carboxylic acid {3-[4-cyano-4-(4-fluorophenyl)-piperidin-1-yl]-propyl}-amide; and 4-(3,4-Difluorophenyl)-6-methoxymethyl-1-methyl-2-oxo-1,2,3,4-tetrahydro-pyriridine-5-carboxylic acid {3-[4-(4-fluorophenyl)-piperidin-1-yl]-propyl}-amide;

and pharmaceutically acceptable salts thereof.

17. The compound according to claim 9, which is

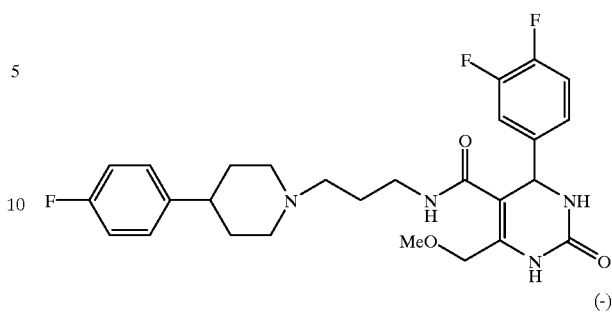

or a pharmaceutically acceptable salt thereof.

18. A pharmaceutical composition comprising the compound according to claim 1 and a pharmaceutically acceptable carrier.

19. A method of treating benign prostatic hyperplasia in a subject in need thereof which comprises administering to the subject a therapeutically effective amount of the compound according to claim 1.

20. The method according to claim 19, wherein the compound additonally does not cause a fall in blood pressure at dosages effective to alleviate benign prostatic hyperlasia.

21. A method of treating benign prostatic hyperplasia in a subject in need thereof which comprises administering a therapeutically effective amount of the composition according to claim 12.

22. A method of relaxing lower urinary tract tissue in a subject in need thereof which comprises administering to the subject a therapeutically effective amount of the compound according to claim 1.

* * * * *